US011414423B1

(12) United States Patent
Olson et al.

(10) Patent No.: US 11,414,423 B1
(45) Date of Patent: Aug. 16, 2022

(54) SUBSTITUTED 1,2,3,4,5,6- HEXAHYDRO-AZEPINO[4,5-B]INDOLES FOR TREATING BRAIN DISORDERS

(71) Applicant: The Regents of the University of California, Oakland, CA (US)

(72) Inventors: David E. Olson, Davis, CA (US); Florence Wagner, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/345,745

(22) Filed: Jun. 11, 2021

Related U.S. Application Data

(63) Continuation of application No. PCT/US2020/019858, filed on Feb. 26, 2020.

(60) Provisional application No. 62/811,208, filed on Feb. 27, 2019.

(51) Int. Cl.
  *A61K 31/407* (2006.01)
  *C07D 487/04* (2006.01)
  *A61P 25/28* (2006.01)
  *A61P 25/32* (2006.01)

(52) U.S. Cl.
  CPC ............ *C07D 487/04* (2013.01); *A61P 25/28* (2018.01); *A61P 25/32* (2018.01)

(58) Field of Classification Search
  CPC .......................... A61K 313/407; C07D 487/04
  USPC ........................................... 514/411; 548/429
  See application file for complete search history.

(56) References Cited

U.S. PATENT DOCUMENTS

| | | | |
|---|---|---|---|
| 3,525,750 A | 8/1970 | Renner |
| 3,553,232 A | 1/1971 | Hester, Jr. |
| 3,652,588 A | 3/1972 | Hester, Jr. |
| 4,478,750 A | 10/1984 | Gadient |
| 4,581,354 A | 4/1986 | Bell |
| 4,841,056 A | 6/1989 | Hunter |
| 5,219,859 A | 6/1993 | Festal et al. |
| 5,494,928 A | 2/1996 | Bos |
| 5,627,077 A | 5/1997 | Dyllick-Brenzinger et al. |
| 5,852,046 A | 12/1998 | Lang et al. |
| 6,017,945 A | 1/2000 | Rawson et al. |
| 6,380,238 B1 | 4/2002 | Adams et al. |
| 6,380,242 B1 | 4/2002 | Arora et al. |
| 6,407,092 B1 | 6/2002 | Hester et al. |
| 6,468,999 B1 | 10/2002 | Jacobsen et al. |
| 6,548,493 B1 | 4/2003 | Robichaud et al. |
| 6,552,017 B1 | 4/2003 | Robichaud et al. |
| 6,635,639 B2 | 10/2003 | Arora et al. |
| 6,828,314 B2 | 12/2004 | Frank et al. |
| 6,903,090 B2 | 6/2005 | Frank et al. |
| 8,338,447 B2 | 12/2012 | Hung et al. |
| 8,367,655 B2 | 2/2013 | Rajagopalan |
| 2002/0022616 A1 | 2/2002 | Fu |
| 2002/0169322 A1 | 11/2002 | Arora et al. |
| 2002/0173503 A1 | 11/2002 | Robichaud et al. |
| 2003/0199491 A1 | 10/2003 | Hennequin |
| 2003/0212055 A1 | 11/2003 | Hennequin |
| 2003/0220321 A1 | 11/2003 | Frank et al. |
| 2003/0225058 A1 | 12/2003 | Frank et al. |
| 2003/0232828 A1 | 12/2003 | Bernotas et al. |
| 2003/0236278 A1 | 12/2003 | Bernotas et al. |
| 2004/0023947 A1 | 2/2004 | Martin et al. |
| 2004/0242884 A1 | 12/2004 | Larsen et al. |
| 2005/0070558 A1 | 3/2005 | Vidal et al. |
| 2005/0250767 A1 | 11/2005 | Weiner et al. |
| 2006/0105030 A1 | 5/2006 | Windt-Hanke et al. |
| 2006/0148808 A1 | 7/2006 | Robichaud et al. |
| 2006/0199829 A1 | 9/2006 | Anandan et al. |
| 2006/0247228 A1 | 11/2006 | Umeda et al. |
| 2007/0197603 A1 | 8/2007 | Consonni et al. |
| 2007/0213359 A1 | 9/2007 | Burstein et al. |
| 2007/0254875 A1 | 11/2007 | Zhi et al. |
| 2009/0318446 A1 | 12/2009 | Fischer et al. |
| 2010/0152163 A1 | 6/2010 | Hung et al. |
| 2010/0317863 A1 | 12/2010 | Kuzmich et al. |
| 2011/0003793 A1 | 1/2011 | Guzzo et al. |
| 2011/0003836 A1 | 1/2011 | McKnight et al. |
| 2011/0003840 A1 | 1/2011 | Rajagopalan |
| 2011/0229555 A1 | 9/2011 | Helson et al. |
| 2011/0245222 A1 | 10/2011 | Payan et al. |
| 2012/0296569 A1 | 11/2012 | Shahaf et al. |
| 2013/0040977 A1 | 2/2013 | McKnight et al. |
| 2013/0178618 A1 | 7/2013 | Boulanger |
| 2013/0190293 A1 | 7/2013 | Chakravarty et al. |
| 2013/0195866 A1 | 8/2013 | Bacskai et al. |
| 2013/0217675 A1 | 8/2013 | Chakravarty et al. |
| 2014/0155384 A1 | 6/2014 | Protter et al. |
| 2014/0206711 A1 | 7/2014 | Chakravarty et al. |
| 2014/0228353 A1 | 8/2014 | Protter et al. |
| 2014/0275531 A1 | 9/2014 | Bollu et al. |

(Continued)

FOREIGN PATENT DOCUMENTS

| | | |
|---|---|---|
| AU | 614343 B2 | 8/1991 |
| CN | 102977091 A | 3/2013 |

(Continued)

OTHER PUBLICATIONS (2018) Depression The National Institute of Mental Health: www.nimh.nih.gov, 13 pages.

European Search Report for EP Application 17857489.3, dated Apr. 8, 2020, 6 pages.

International Search Report and Written Opinion received for International Application No. PCT/US2020/019858, dated Jul. 15, 2020, 12 pages.

International Search Report and Written Opinion received for International Application No. PCT/US2020/055507, dated Mar. 1, 2021, 12 pages.

International Search Report and Written Opinion received for PCT Application No. PCT/US2017/054277, dated Dec. 14, 2017, 10 pages.

(Continued)

*Primary Examiner* — Douglas M Willis
(74) *Attorney, Agent, or Firm* — Mintz, Levin, Cohn, Ferris, Glovsky and Popeo, P.C.

(57) ABSTRACT

The present invention provides substituted 1,2,3,4,5,6-hexahydroazepino[4,5-b]indoles and methods of using the compounds for treating brain disorders.

28 Claims, 22 Drawing Sheets

(56) References Cited

U.S. PATENT DOCUMENTS

| | | |
|---|---|---|
| 2014/0275548 A1 | 9/2014 | Basinger et al. |
| 2014/0296209 A1 | 10/2014 | Protter et al. |
| 2014/0303144 A1 | 10/2014 | Protter et al. |
| 2014/0343018 A1 | 11/2014 | McKnight et al. |
| 2015/0057301 A1 | 2/2015 | McKnight et al. |
| 2015/0141345 A1 | 5/2015 | Gozes et al. |
| 2015/0266884 A1 | 9/2015 | Protter et al. |
| 2016/0002237 A1 | 1/2016 | Rajagopalan |
| 2018/0263964 A1 | 9/2018 | Bamdad et al. |
| 2020/0030309 A1 | 1/2020 | Olson |
| 2020/0087305 A1 | 3/2020 | Tomesch et al. |

FOREIGN PATENT DOCUMENTS

| | | |
|---|---|---|
| CN | 102977092 A | 3/2013 |
| GB | 2550110 A | 11/2017 |
| NL | 6515701 A | 6/1966 |
| WO | 9840102 A1 | 9/1998 |
| WO | 2000038677 | 7/2000 |
| WO | 0064899 A1 | 11/2000 |
| WO | 2001070223 | 9/2001 |
| WO | 2004005389 A1 | 1/2004 |
| WO | 2004064738 A2 | 8/2004 |
| WO | 2008117935 A1 | 10/2008 |
| WO | 2008157845 A1 | 12/2008 |
| WO | 2009035473 A2 | 3/2009 |
| WO | 2009103022 A1 | 8/2009 |
| WO | 2013007698 A1 | 1/2013 |
| WO | 2017216279 A1 | 12/2017 |
| WO | 2018045178 A1 | 3/2018 |
| WO | 2018064465 A1 | 4/2018 |
| WO | 2018209341 A1 | 11/2018 |
| WO | 2019099402 A1 | 5/2019 |
| WO | 2020169851 A1 | 8/2020 |
| WO | 2020176597 A1 | 9/2020 |
| WO | 2020176599 A1 | 9/2020 |
| WO | 2020181050 A1 | 9/2020 |
| WO | 2020181194 A1 | 9/2020 |
| WO | 2020186027 A1 | 9/2020 |
| WO | 2021076572 A1 | 4/2021 |

OTHER PUBLICATIONS

International Search Report and Written Opinion received for PCT Application No. PCT/US2020/019856, dated Jun. 26, 2020, 11 pages.

U.S. Appl. No. 17/345,471, filed Jun. 11, 2021, "N-Substituted Indoles And Other Heterocycles For Treating", 157 pages.

Anderson Amy C. (Sep. 2003) "The Process of Structure-based Drug Design", Chemistry and Biology, 10(9):787-797.

Antonaci et al. (May 17, 2016) "Recent Advances in Migraine Therapy", SpringerPlus 5:1-14.

Borovac Josip A. (Mar. 24, 2016) "Side Effects of a Dopamine Agonist Therapy for Parkinson's Disease: A Mini-review of Clinical Pharmacology", Yale Journal of Biology and Medicine, 89:37-47.

Cameron et al. (Jan. 21, 2021) "A Non-hallucinogenic Psychedelic Analogue With Therapuetic Potential", Nature, 589:474-479(24 pages).

Cameron et al. (Jul. 2019) "Chronic, Intermittent Microdoses of the Psychedelic N,N-Dimethyltryptamine (DMT) Produce Positive Effects on Mood and Anxiety in Rodents", ACS Chemical Neuroscience, 10(7):3261-3270.

Cameron et al. (Oct. 2018) "Dark Classics in Chemical Neuroscience: N,N-Dimethyltryptamine (DMT)", ACS Chemical Neuroscience, 9(10):2344-2357.

Cameron et al. (Jul. 2018) "Effects of N,N-Dimethyltryptamine on Rat Behaviors Relevant to Anxiety and Depression", ACS Chemical Neuroscience, 9(7):1582-1590(22 pages).

Cameron et al. (Apr.-Jun. 2020) "Psychedelic Microdosing: Prevalence and Subjective Effects", Jounal of Psychoactive Drugs, 52(2):113-122.

Chiba et al. (May 23, 2010) "Cabergoline, a Dopamine Receptor Agaonist, has an Antidepressant-like Property and Enhances Brain-derived Neurotrophic Factor Signaling", Psychpharmacology 211(3):291-301 (23 pages).

Dunlap et al. (Jan. 2020) "Identification of Psychoplastogenic N,N-Dimethylaminoisotryptamine (isoDMT) Analogues through Structure—Activity Relationship Studies", Journal of Medicinal Chemistry, 63(3):1142-1155(36 pages).

Glennon et al. (2000) "Binding of Beta-Carbolines and Related Agents at Serotonin (5-HT(2) and 5-HT(1A)), Dopamine (D(2)) and Benzodiazepine Receptors", Drug & Alcohol Dependence, 60(2):121-132.

Glennon et al. (1983) "DOM-stimulus Generalization to LSD and other Hallucinogenic Indolealkylamines", European Journal of Pharmacology, 86:453-459.

Goadsby et al. (2005) Comparative Efficacy of Eletriptan and Sumatriptan in Reducing Headache Recurrence in High-Risk Migraine Patients, Journal of the Neurological Sciences, 238(Suppl. 1):S940.

Golda et al. (Jun. 1987) "Animal Model of Depression: Drug Induced Changes Independent of Changes in Exploratory Activity", Activitas Nervosa Superior, 29(2):114-115.

Golda et al. (1986) "Animal Model of Depression: Imipramine, Bromocriptine and Lisuride Alleviate Motor Depression", Activitas Nervosa Superior, 28(1):26-27(4 pages).

Golda et al. (1984) "Reactivity to the Electric Shocks and Motor Depression as a Consequence of Inescapable Shocking: the Effect of Acute Lisuride Treatment", 27(4):377-392.

Halford Bethany (Dec. 2020) "Ibogaine Inspires Potential Neuropsychiatric Treatment", C&E News, 3 pages.

Harris et al. (2012) "Cabergoline Associated with First Episode Mania", Psychosomatics, 53(6):595-600(10 pages).

Hougaku et al. (Jan. 1994) "Therapeutic Effect of Lisuride Maleate on Post-stroke Depression", Journal of Geriatrics, 31:52-59.

Izumi et al. (2000) "Open Pergolide Treatment of Tricyclic and Heterocyclic Antidepressant-resistant Depression", Journal of Affective Disorders, 61:127-132.

Konopaske et al. (Dec. 2014) "Prefrontal Cortical Dendritic Spine Pathology in Schizophrenia and Bipolar disorder", JAMA Psychiatry, 71(12):1323-1331.

Lieberman et al. (Nov. 1981) "Use of Lisuride in Advanced Parkinson's Disease. Potent Dopamine and Serotonin Agonist", New York State Journal of Medicine, 81(12):1751-1755.

Luquin et al. (1987) "Parenteral Administration of Lisuride In Parkinson's Disease", Advances in Neurology, 45:561-568.

Ly et al. (Jun. 12, 2018) "Psychedelics Promote Structural and Functional Neural Plasticity", Cell Reports, 23(11):3170-3182.

Meintzschel et al. (Oct. 12, 2005) "Modification of Practice-dependent Plasticity in Human Motor Cortex by Neuromodulators", Cerebral Cortex, 16(8):1106-1115.

Meyer et al. (Jan. 2001) "The Effect of Paroxetine on 5-HT 2A Receptors in Depression: An [18F]Setoperone PET Imaging Study", The American Journal of Psychiatry, 158(1)78-85.

Moyer et al. (2015) "Dendritic Spine Alterations in Schizophrenia", Neuroscience Letters, 601:46-53(18 pages).

Nakamura et al. (1989) "Effects in Animal Models of Depression of Lisuride Along and Upon Co-administration with antidepressants", Folia pharmacol.japon, 94(1):81-89.

Odaka et al. (Jun. 2014) "Cabergoline, Dopamine D2 REceptor Agonist, Prevents Neuronal Cell Death under Oxidative Stress via Reducing Excitotoxicity", PLoS One, 9(6):12 pages.

Penzes et al. (Mar. 2011) "Dendritic Spine Pathology in Neuropsychiatric Disorders", Nature Neuroscience Review, 14(3):285-293(22 pages).

Pfizer Canana, Inc. (Jul. 23, 2013) "Product Monograph", Pfizer Cananda Inc., pp. 1-2.

PUBCHEM (Oct. 20, 2014) "1,2,3,4-Tetrahydropyrrolo[2,3-b]lndole", PubChem CID 82415753, 8 pages.

PUBCHEM (Jun. 16, 2016) "3,4-Trimethylen-inden", PubChem SID 314981250, 5 pages.

PUBCHEM (Aug. 8, 2005) "Carbazole, 9-(1-methyl-2-piperidyl)methyl-", PubChem CID 43403, 10 pages.

Sharma Gitanjali (Nov. 6, 2019) "Intranasal Cabergoline: Pharmacokinetic and Pharmacodynamic Studies", AAPS PHarSciTech, 10(4):1321-1330.

(56) References Cited

OTHER PUBLICATIONS

Thiel Karl A. (May 2004) "Structure-Aided Drug Design's Next Generation", Nature Biology, 22(5):513-519.
Tittarelli et al. (2015) "Recreational Use, Analysis and Toxicity of Tryptamines", Current Neuropharmacology, 13(1):26-46.
Zetler et al. (1972) "Refractory Period and Strophanthin Actions, as Influenced by Four Indole Alkaloids and Two Synthetic Azepinoindoles", Pharmacology, 8:235-243.
Chang-Fong et al., "Evaluation of Isotryptamine Derivatives at 5-HT2 Serotonin Receptors", Bioorg. Med. Chem. Lett. 2002, 12, 155-158.
Glennon et al., "Synthesis and Evaluation of a Novel Series of N,N-Dimethylisotryptamines", J. Med. Chem. 1984, 27, 41-45.
Vargas, "Psychedelics and Other Psychoplastogens for Treating Mental Illness" Frontiers in Psychiatry 2021, p. 1-19.
Third Party Observations received for European Application No. 17857489.3, dated Feb. 15, 2022, 2 pages.
Hester et al. (Jan. 1, 1968) "Azepinoindoles. I. Hexahydroazepino[4,5-b]indoles", Journal of Medicinal Chemistry, 11:101-106.
Pumphrey et al. (Jun. 11, 2012) "RhII2-Catalyzed Synthesis of α-, β-, or σ-Carbolines from Aryl Azides", Angewandte Chemie International Edition, 51(24):5920-5923 (10 pages).
Zetler et al. (Jan. 1968) "Die Wirkung von 11 Indol-Alkaloiden auf das Meerschweinchen—Herz in vivo und in vitro, verglichen mit 2 synthetischen Azepinoindolen, Chinidin und Quindonium", Naunyn-Schmiedebergs Archiv für Pharmakologie und experimentelle Pathologie 260:26-49.
Zetler et al. (1970) "Inhibition of Cardiac Effects of Noradrenaline by Eleven Indole Alkaloids, Two Azepinoindoles, Quinidine, Quindonium, and Propranolol", Pharmacology, 4:129-142.

FIG. 1A
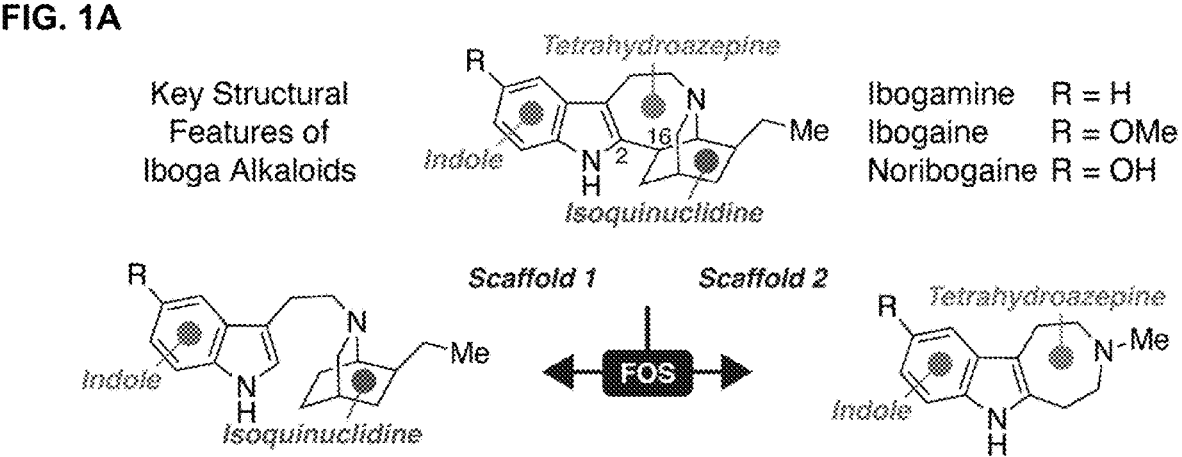
FIG. 1B
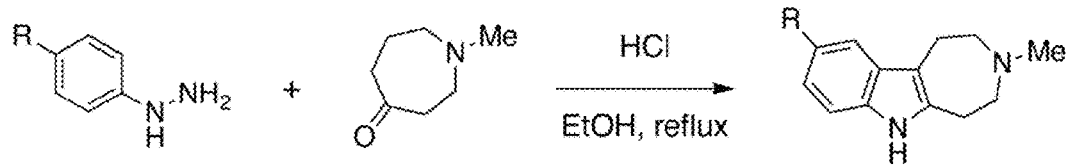
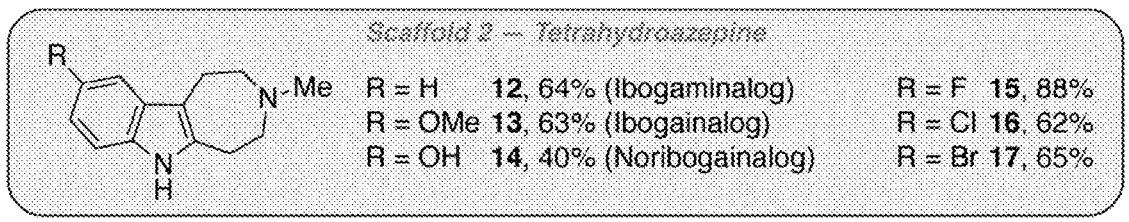

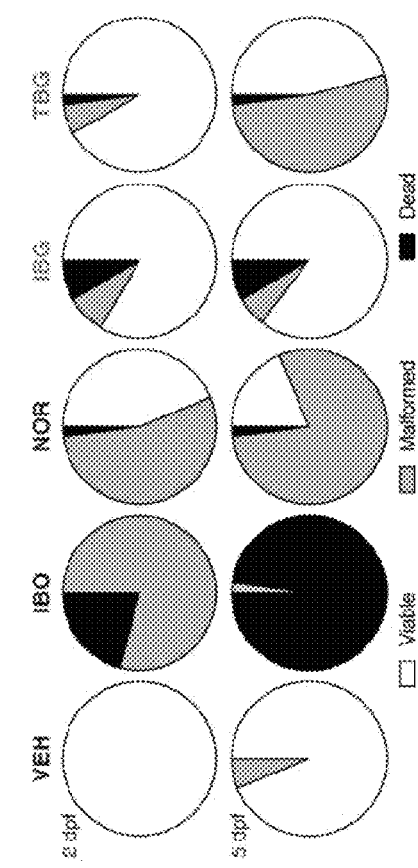
FIG 2G
FIG 2H
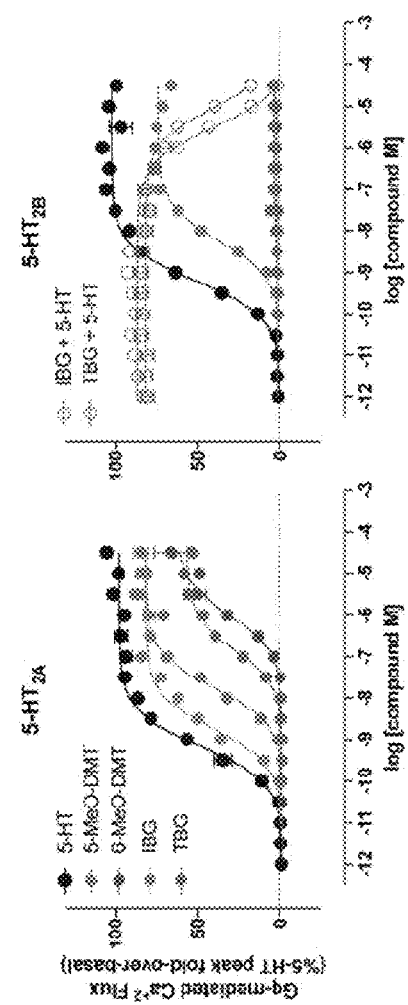
FIG 2I
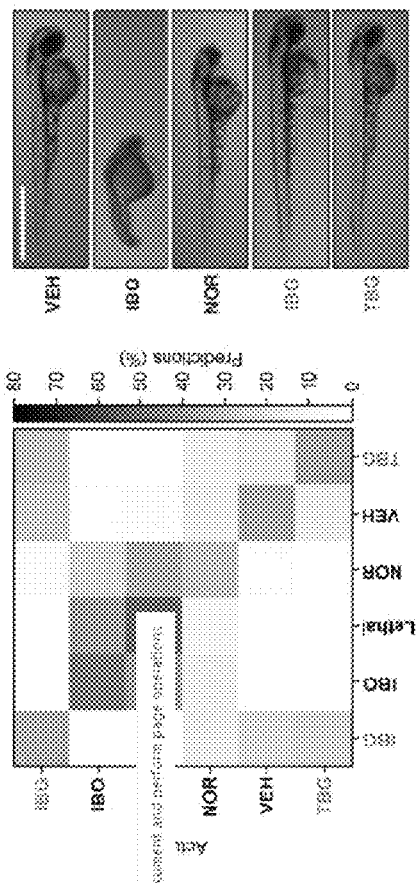
FIG 2J
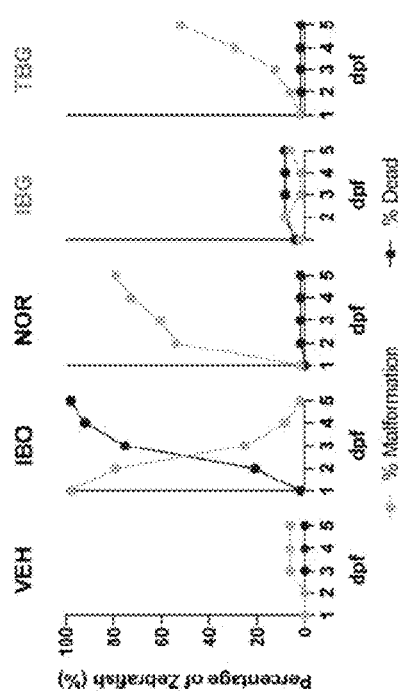
FIG 2K

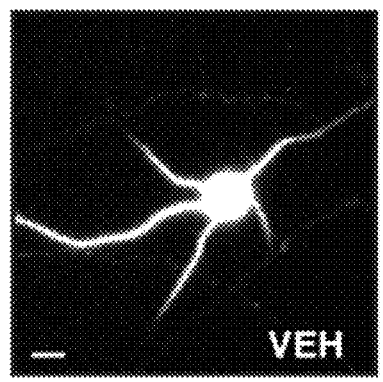
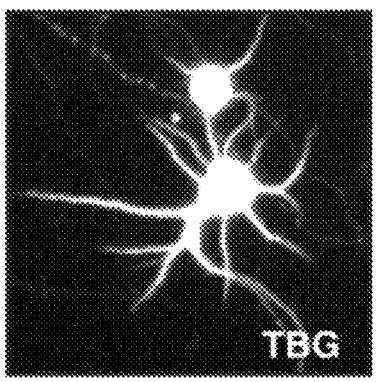
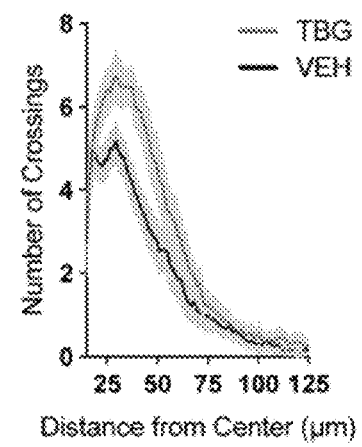
FIG. 3A
FIG. 3B
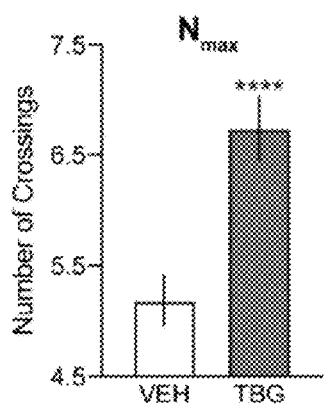
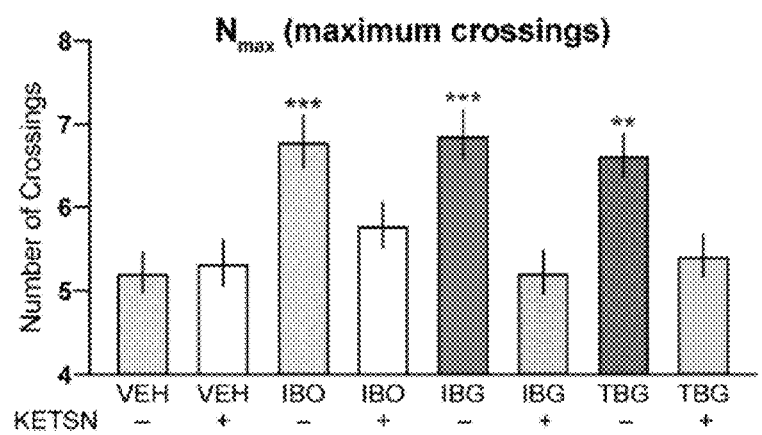
FIG. 3C
FIG. 3D
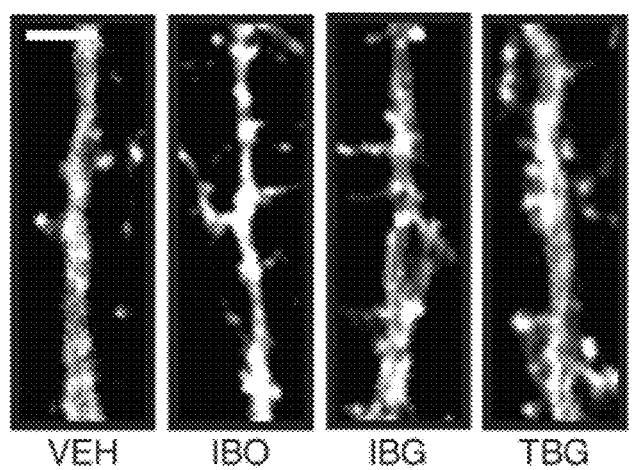
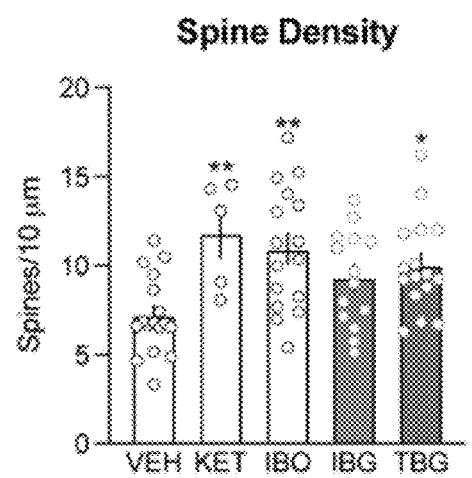
FIG. 3E
FIG. 3F

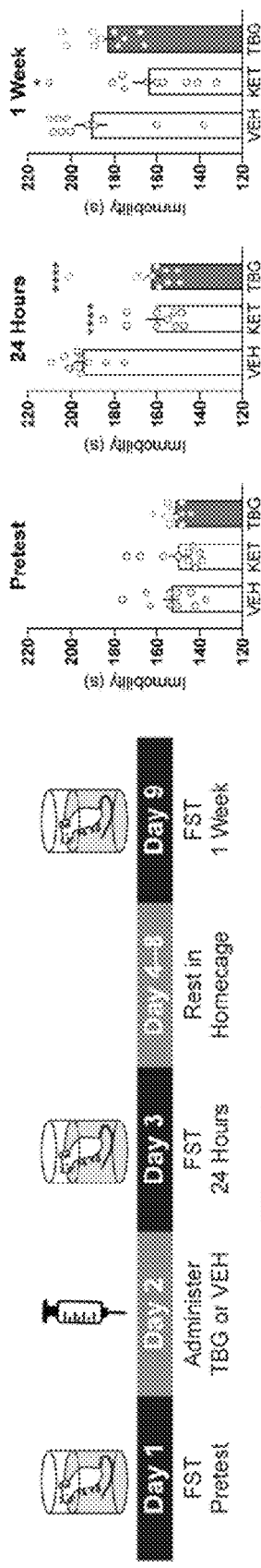
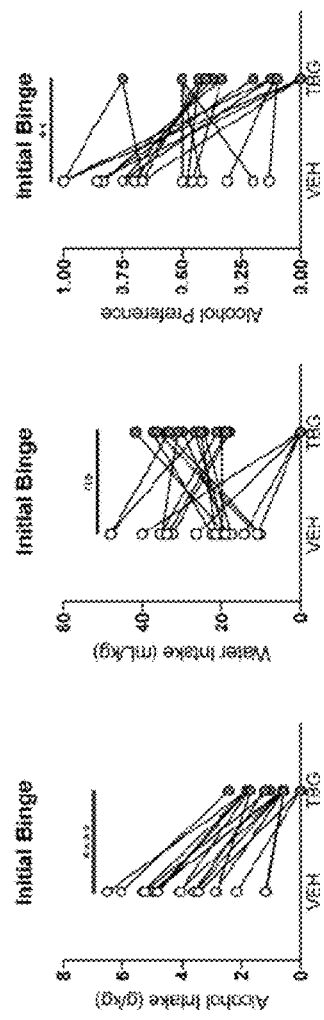
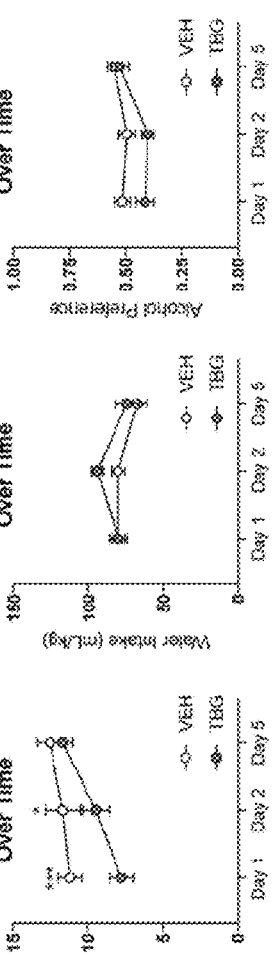
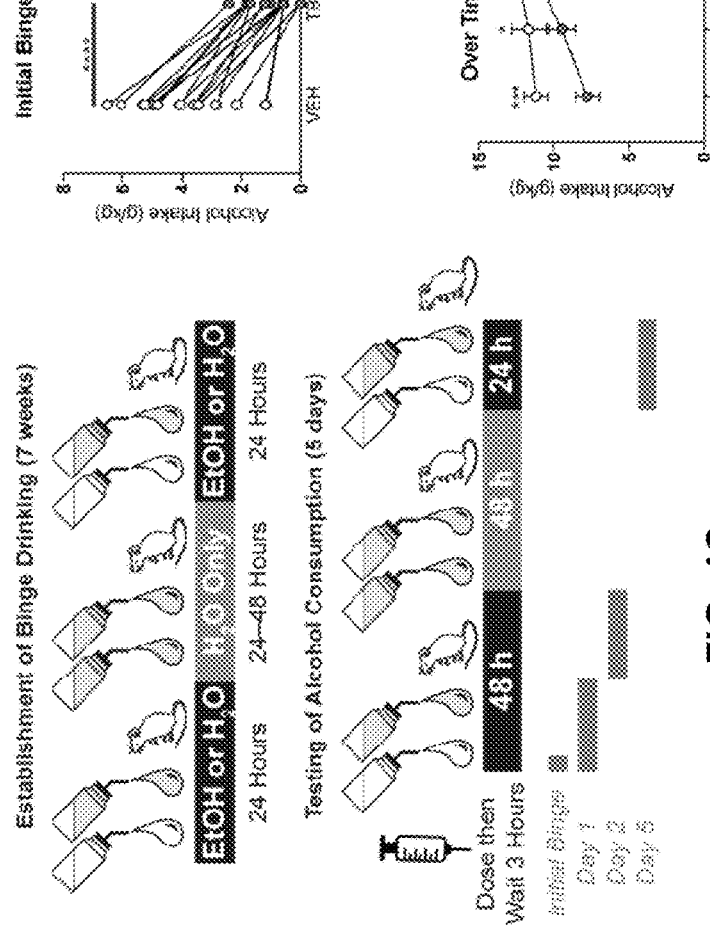
FIG. 4A
FIG. 4B
FIG. 4C
FIG. 4D
FIG. 4E

FIG. 7

| Vehicle Conditions | Concentration | Soluble? |
|---|---|---|
| Saline + 10% EtOH + 10% DMSO | 40 mg/ml | NO |
| Saline + 10% EtOH | 8 mg/ml | NO |
| Saline + 10% DMSO | 8 mg/ml | NO |
| Saline + 10% EtOH + 10% DMSO | 8 mg/ml | NO |
| Saline + 10% EtOH + 10% Kolliphor | 8 mg/ml | NO |
| Saline + 10% EtOH + 20% Kolliphor | 8 mg/ml | NO |
| Saline + 10% EtOH + 25% Kolliphor | 8 mg/ml | NO |
| Saline + 10% EtOH + 30% Kolliphor | 8 mg/ml | NO |
| Saline + 10% EtOH + 40% Kolliphor | 8 mg/ml | NO |
| Saline + 10% DMSO + 10% Kolliphor | 8 mg/ml | NO |
| Saline + 10% DMSO + 25% Kolliphor | 8 mg/ml | NO |
| Saline + 10% DMSO + 15% Glycerol | 8 mg/ml | NO |
| Saline + 10 mM ATP | 8 mg/ml | NO |
| Saline + 10% DMSO | 4 mg/ml | NO |
| Saline + 10% DMSO + 25% Kolliphor | 4 mg/ml | NO |
| Saline + 10% DMSO | 1 mg/ml | YES |

FIG. 13

| Target Receptor | 5-MeO-DMT | | | 6-MeO-DMT | | | IBG | | | TBG | | | IBO | | | NOR | | |
|---|---|---|---|---|---|---|---|---|---|---|---|---|---|---|---|---|---|---|
| | EC50, nM | Emax % Control | log(Emax /EC50) | EC50, nM | Emax % Control | log(Emax /EC50) | EC50, nM | Emax % Control | log(Emax /EC50) | EC50, nM | Emax % Control | log(Emax /EC50) | EC50, nM | Emax % Control | log(Emax /EC50) | EC50, nM | Emax % Control | log(Emax /EC50) |
| 5-HT1A | 3.92 | 96 | 8.40 | 725.40 | 91 | 6.10 | 6691.20 | 91 | 5.12 | 14860.00 | 96 | 3.81 | | | | | | |
| 5-HT1B | 1.53 | 78 | 8.71 | 37.06 | 65 | 7.36 | 170.40 | 76 | 6.66 | 53.96 | 87 | 7.41 | | | | | | |
| 5-HT1D | 37.61 | 98 | 7.42 | 3036.60 | 120 | 5.57 | 6043.95 | 82 | 5.13 | 2180.00 | 79 | 5.54 | | | | | | |
| 5-HT1e | 160.20 | 119 | 6.87 | 2363.00 | 131 | 5.74 | 9306.20 | 129 | 5.13 | 7784.00 | 117 | 5.62 | | | | | | |
| 5-HT1F | 14.00 | 93 | 7.82 | 44.50 | 88 | 7.30 | 35.10 | 85 | 7.38 | 40.40 | 64 | 7.20 | | | | | | |
| 5-HT2A | 1.85 | 82 | 8.65 | 1000.00 | 83 | 5.85 | 19.10 | 82 | 7.56 | 147.00 | 57 | 6.59 | | | | | | |
| 5-HT2B | 5.97 | 73 | 8.01 | | | | | | | | | | | | | | | |
| 5-HT2C | 30.70 | 84 | 7.44 | | | | | | | | | | | | | | | |
| 5-HT3 | >10,000 | N.D. | <5.00 | >10,000 | N.D. | <5.00 | >10,000 | N.D. | <5.00 | >10,000 | N.D. | <5.00 | | | | | | |
| 5-HT5a | 116.60 | 107 | 6.91 | 4543.00 | 112 | 5.41 | >10,000 | N.D. | <5.00 | >10,000 | N.D. | <5.00 | | | | | | |
| 5-HT6 | 0.24 | 125 | 9.72 | 162.00 | 113 | 6.84 | 6.85 | 83 | 7.07 | 214.00 | 87.5 | 6.61 | | | | | | |
| 5-HT7 | 66.70 | 107 | 7.21 | 5053.00 | 75 | 5.12 | 335.00 | 77 | | >10,000 | N.D. | <5.00 | | | | | | |
| MOR | | | | >10,000 | N.D. | | >10,000 | N.D. | | >10,000 | N.D. | | >10,000 | N.D. | | 1402 | 85 | 6.78 |
| KOR | | | | | | | | | | | | | | | | | | |
| DOR | | | | | | | | | | | | | | | | | | |

SUBSTITUTED 1,2,3,4,5,6-HEXAHYDROAZEPINO[4,5-B]INDOLES FOR TREATING BRAIN DISORDERS

CROSS-REFERENCES TO RELATED APPLICATIONS

This application is a continuation of International PCT Patent Application No. PCT/US2020/019858, filed Feb. 26, 2020, which claims priority to U.S. Provisional Application No. 62/811,208, filed Feb. 27, 2019, which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. R01GM128997 awarded by the National Institutes of Health. The Government has certain rights in this invention.

BACKGROUND OF THE INVENTION

The psychedelic alkaloid ibogaine has robust anti-addictive properties in the clinic and in animal models. Ibogaine possesses the potential to treat patients addicted to a variety of substances, for example, including opiates, psychostimulants, alcohol, and nicotine. Moreover, its therapeutic effects are long lasting, which has been attributed to its ability to modify addiction-related neural circuitry through activation of neurotrophic factor signaling. Ibogaine reduces symptoms of drug withdrawal, reduces drug cravings, and prevents relapse. In rodents, ibogaine reduces drug self-administration and prevents drug-induced dopamine release in several brain regions. However, several safety concerns have hindered the clinical development of ibogaine, including, for example, its toxicity, hallucinogenic potential, and proclivity for inducing cardiac arrhythmias via hERG channel inhibition.

Ibogaine increases glial cell line-derived neurotrophic factor (GDNF) expression in the ventral tegmental area (VTA), and intra-VTA infusion of ibogaine reduces alcohol-seeking behavior in rodents. Ibogaine impacts brain-derived neurotrophic factor (BDNF) and GDNF signaling in multiple brain regions implicated in the pathophysiology of addiction. Noribogaine, an active metabolite of ibogaine, is a potent psychoplastogen capable of increasing cortical neuron dendritic arbor complexity. Other psychoplastogens, such as lysergic acid diethylamide (LSD) and psilocin (the active metabolite of psilocybin) have anti-addictive properties in the clinic similar to ibogaine. The ability of psychoplastogens to promote structural and functional neural plasticity in addiction-related circuitry can explain their abilities to reduce drug-seeking behavior for weeks to months following a single administration. Moreover, by modifying neural circuitry rather than simply blocking the targets of a particular addictive substance (e.g., opioid receptors, nicotinic receptors, etc.), psychoplastogens like ibogaine have the potential to be broadly applicable anti-addictive agents.

What is needed are new compounds lacking ibogaine's toxicity and hallucinogenic effects but maintain therapeutic efficacy. Surprisingly, the present invention meets this and other needs.

BRIEF SUMMARY OF THE INVENTION

In one embodiment, the present invention provides a compound of Formula I:

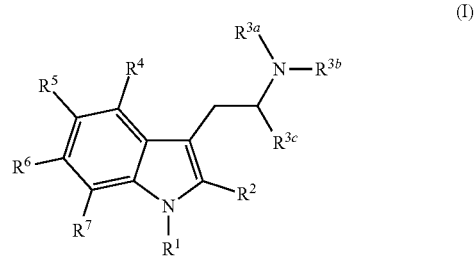

(I)

wherein: $R^1$ is hydrogen or $C_{1-6}$ alkyl; $R^{3a}$ and $R^{3b}$ are each independently hydrogen, $C_{1-6}$ alkyl, $C_{3-8}$ cycloalkyl, or $C_{4-14}$ alkyl-cycloalkyl; $R^{3c}$ is hydrogen or $C_{1-6}$ alkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O; alternatively, $R^2$ and $R^{3c}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O; $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —C(O)$R^{8b}$, —C(O)O$R^{8b}$, —OC(O)$R^{8b}$, —OC(O)O$R^{8b}$, —N($R^{8b}R^{8c}$), —N($R^{8b}$)C(O)$R^{8c}$, —C(O)N($R^{8b}R^{8c}$), —N($R^{8b}$)C(O)O$R^{8c}$, —OC(O)N($R^{8b}R^{8c}$), —N($R^{8b}$)C(O)N($R^{8c}R^{8d}$), —C(O)C(O)N($R^{8b}R^{8c}$), —S($O_2$)$R^{8b}$, —S(O)$_2$N($R^{8b}R^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl or $C_{5-10}$ heteroaryl; $R^{8a}$, $R^{8b}$, $R^{8c}$ and $R^{8d}$ are each independently H, $C_{1-6}$ alkyl; wherein when $R^2$ and $R^{3b}$ are combined with the atoms to which they are attached to form a $C_7$ heterocycloalkyl, and $R^{3a}$ is methyl, then $R^5$ is not OMe, OH, or Cl; wherein when $R^2$ and $R^{3b}$ are combined with the atoms to which they are attached to form a $C_7$ heterocycloalkyl, and $R^{3a}$ is ethyl, then $R^6$ is not OMe; wherein when $R^2$ and $R^{3b}$ are combined with the atoms to which they are attached to form a $C_7$ heterocycloalkyl, and $R^6$ is methyl, Cl, F, or —OMe, then at least one of $R^4$, $R^5$, and $R^7$ is not hydrogen; wherein when $R^2$ and $R^{3b}$ are combined with the atoms to which they are attached to form a $C_6$ heterocycloalkyl, and $R^6$ is $C_{1-6}$ alkyl, halogen, $C_{1-6}$ alkyoxy, —C(O)H, —$NH_2$, then at least one of $R^4$, $R^5$, and $R^7$ is not hydrogen; and wherein when $R^2$ and $R^{3b}$ are combined with the atoms to which they are attached to form a $C_6$ heterocycloalkyl, and $R^6$ is methyl, halogen, or —C(O)H, then at least one of $R^4$, $R^5$, and $R^7$ is not methyl or Cl, or pharmaceutically acceptable salts and isomers thereof.

In another embodiment, the present invention provides a compound, or a pharmaceutically acceptable salt thereof, wherein the compound is

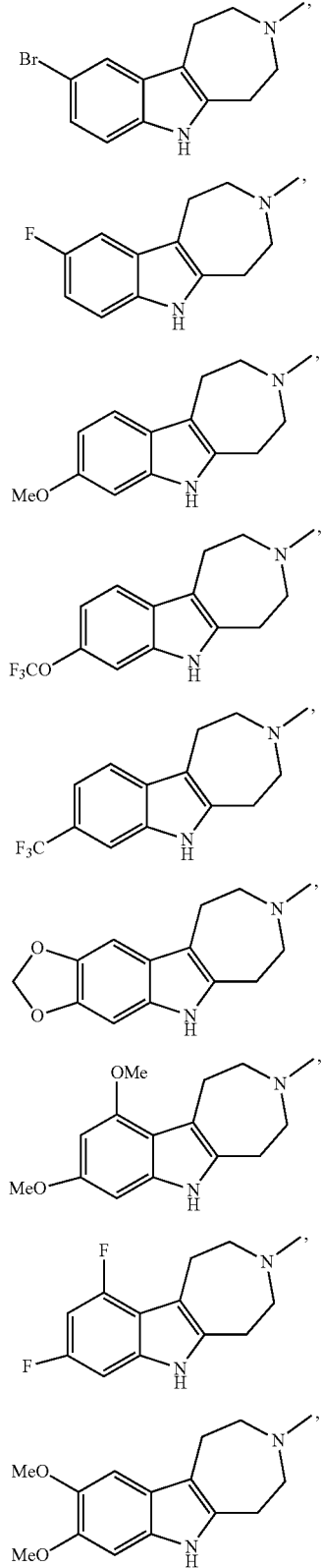

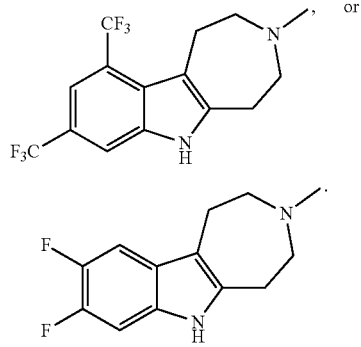

In another embodiment, the present invention provides a pharmaceutical composition comprising a compound of the present invention, or a pharmaceutically acceptable salt thereof, and a pharmaceutically acceptable excipient.

In another embodiment, the present invention provides a method for increasing neuronal plasticity, comprising contacting a neuronal cell with a compound of Formula I:

$$\text{(I)}$$

or a pharmaceutically acceptable salt thereof, in an amount sufficient to increase neuronal plasticity of the neuronal cell, wherein: $R^1$ is hydrogen or $C_{1-6}$ alkyl; $R^{3a}$ and $R^{3b}$ are each independently hydrogen, $C_{1-6}$ alkyl, $C_{3-8}$ cycloalkyl, or $C_{4-14}$ alkyl-cycloalkyl; $R^{3c}$ is hydrogen or $C_{1-6}$ alkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O; alternatively, $R^2$ and $R^{3c}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O; $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, $—OR^{8a}$, $—NO_2$, $—CN$, $—C(O)R^{8b}$, $—C(O)OR^{8b}$, $—OC(O)R^{8b}$, $—OC(O)OR^{8b}$, $—N(R^{8b}R^{8c})$, $—N(R^{8b})C(O)R^{8c}$, $—C(O)N(R^{8b}R^{8c})$, $—N(R^{8b})C(O)OR^{8c}$, $—OC(O)N(R^{8b}R^{8c})$, $—N(R^{8b})C(O)N(R^{8c}R^{8d})$, $—C(O)C(O)N(R^{8b}R^{8c})$, $—S(O_2)R^{8b}$, $—S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H;

alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl or $C_{5-10}$ heteroaryl; and $R^{8a}$, $R^{8b}$, $R^{8c}$ and $R^{8d}$ are each independently H, $C_{1-6}$ alkyl.

In another embodiment, the present invention provides a method of treating a brain disorder, comprising administering to a subject in need thereof a therapeutically effective amount of a compound of Formula I:

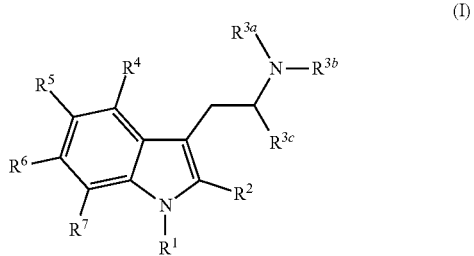
(I)

or a pharmaceutically acceptable salt thereof, thereby treating the brain disorder, wherein: $R^1$ is hydrogen or $C_{1-6}$ alkyl; $R^{3a}$ and $R^{3b}$ are each independently hydrogen, $C_{1-6}$ alkyl, $C_{3-8}$ cycloalkyl, or $C_{4-14}$ alkyl-cycloalkyl; $R^{3c}$ is hydrogen or $C_{1-6}$ alkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O; alternatively, $R^2$ and $R^{3c}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O; $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —C(O)$R^{8b}$, —C(O)O$R^{8b}$, —OC(O)$R^{8b}$, —OC(O)O$R^{8b}$, —N($R^{8b}R^{8c}$), —N($R^{8b}$)C(O)$R^{8c}$, —C(O)N($R^{8b}R^{8c}$), —N($R^{8b}$)C(O)O$R^{8c}$, —OC(O)N($R^{8b}R^{8c}$), —N($R^{8b}$)C(O)N($R^{8c}R^{8d}$), —C(O)C(O)N($R^{8b}R^{8c}$), —S($O_2$)$R^{8b}$, —S(O)$_2$N($R^{8b}R^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl or $C_{5-10}$ heteroaryl; and $R^{8a}$, $R^{8b}$, $R^{8c}$ and $R^{8d}$ are each independently H, $C_{1-6}$ alkyl.

In another embodiment, the present invention provides a method for increasing at least one of translation, transcription or secretion of neurotrophic factors, comprising contacting a neuronal cell with a compound of Formula I:

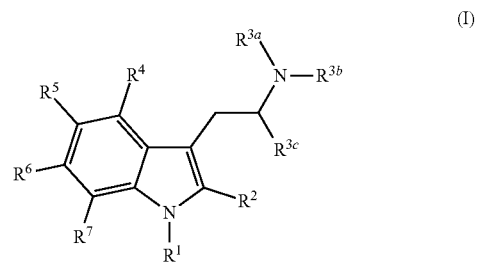
(I)

or a pharmaceutically acceptable salt thereof, in an amount sufficient to increase neuronal plasticity of the neuronal cell, wherein: $R^1$ is hydrogen or $C_{1-6}$ alkyl; $R^{3a}$ and $R^{3b}$ are each independently hydrogen, $C_{1-6}$ alkyl, $C_{3-8}$ cycloalkyl, or $C_{4-14}$ alkyl-cycloalkyl; $R^{3c}$ is hydrogen or $C_{1-6}$ alkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O; alternatively, $R^2$ and $R^{3c}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O; $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —C(O)$R^{8b}$, —C(O)O$R^{8b}$, —OC(O)$R^{8b}$, —OC(O)O$R^{8b}$, —N($R^{8b}R^{8c}$), —N($R^{8b}$)C(O)$R^{8c}$, —C(O)N($R^{8b}R^{8c}$), —N($R^{8b}$)C(O)O$R^{8c}$, —OC(O)N($R^{8b}R^{8c}$), —N($R^{8b}$)C(O)N($R^{8c}R^{8d}$), —C(O)C(O)N($R^{8b}R^{8c}$), —S($O_2$)$R^{8b}$, —S(O)$_2$N($R^{8b}R^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl or $C_{5-10}$ heteroaryl; and $R^{8a}$, $R^{8b}$, $R^{8c}$ and $R^{8d}$ are each independently H, $C_{1-6}$ alkyl.

BRIEF DESCRIPTION OF THE DRAWINGS

FIG. 1A to FIG. 1B show function-oriented synthesis of ibogalogs. FIG. 1A shows key structural features of ibogaine and related alkaloids. Deletion of either the isoquinuclidine or tetrahydroazepine leads to simplified ibogaine analogs. FIG. 1B shows synthesis of tetrahydroazepine-containing ibogalogs.

FIG. 2A to FIG. 2K show tabernanthalog (TBG) is a safer analog of iboga alkaloids. FIG. 2A shows the design of ibogainalog (IBG) and TBG, simplified analogs of ibogaine and tabernanthine, respectively. FIG. 2B shows mouse HTR assays demonstrate that TBG is not hallucinogenic. The doses (mg/kg) of IBG and TBG are indicated. +Ctrl=5-MeO-DMT (10 mg/kg). FIG. 2C shows solubility of various drugs in a 0.9% saline solution. FIG. 2D shows inhibition of hERG channels expressed in HEK293 cells. FIG. 2E shows that unlike ibogaine, IBG and TBG do not induce bradycardia in larval zebrafish. FIG. 2F shows ratio of atrium to ventricle beats per minute (BPM). Deviations from 1 indicate an increased risk of arrhythmias. Sertindole (SI) was used as a positive control. FIG. 2G shows confusion matrix for classification of D30, NOR, IBG, and TBG (200 µM), plus VEH and lethal controls. Cells show the proportion of classification between true labels (Y-axis) and predicted labels (X-axis). FIG. 2H shows representative images of zebrafish treated with compounds (100 µM) for 2 dpf. Scale bar=1 mm. FIG. 2I shows proportion of viable and non-viable (malformed or dead) zebrafish following treatment with compounds (100 µM). FIG. 2J shows the effects of compound treatment on malformation and death over time. FIG. 2K shows agonist and antagonist activities at the 5-HT$_{2A}$ and 5-HT2B receptors as measured by Gq-mediated calcium flux. Data represent percent 5-HT fold-over-basal response performed from at least three independent experiments performed in duplicate. D30=ibogaine, NOR= noribogaine.

FIG. 3A to FIG. 3I show TBG promotes neural plasticity. FIG. 3A shows representative images of rat embryonic cortical neurons (DIV6) treated with TBG or VEH. Scale bar=10 µm. FIG. 3B shows Sholl analysis of TBG and VEH treated neurons. The light shadings represent 95% confidence intervals. FIG. 3C shows maximum numbers of crossings ($N_{max}$) of the Sholl plot in b demonstrate that TBG increases dendritic arbor complexity. FIG. 3D shows the effects of TBG on dendritic growth are blocked by the 5-HT2A antagonist ketanserin (KETSN). FIG. 3E shows representative images of secondary branches of rat embryonic cortical neurons (DIV20) after treatment with ibogalogs for 24 h. Scale bar=2 µm. FIG. 3F shows TBG increases dendritic spine density on rat embryonic cortical neurons (DIV20) after treatment for 24 h. KET=ketamine. FIG. 3G shows schematic illustrating the design of in vivo spine dynamics experiments using transcranial 2-photon imaging. FIG. 3H shows representative images of the same dendritic segments from mouse primary sensory cortex before (Day 0) and after (Day 1) treatment with VEH, DOI, or TBG. Blue, red, and white arrowheads represent newly formed spines, eliminated spines, and filopodia, respectively. Scale bar=2 µm. FIG. 3I shows quantification of spine dynamics reveals that DOI and TBG increase spine formation but have no effect on spine elimination.

FIG. 4A to FIG. 4E show TBG has antidepressant and anti-addictive properties. FIG. 4A shows schematic illustrating the design of FST experiments. Mice were subjected to a pretest, dosed with compounds, and then retested at 24 h and 7 days following drug administration. FIG. 4B shows quantification of immobility reveals that TBG has antidepressant-like effects. FIG. 4C shows timeline of binge-drinking experiment. Bottles of 20% EtOH (white droplets) and H$_2$O (blue droplets) were available for 24 h periods every 1-2 days for 7 weeks. Between drinking sessions, two bottles of H$_2$O were provided. FIG. 4D shows TBG reduces EtOH consumption and preference during a binge drinking session without impacting H$_2$O intake. FIG. 4E TBG administration results in long-lasting decreases in EtOH consumption.

FIG. 5A shows representative images of rat embryonic cortical neurons (DIV6) treated with compounds. Scale bar=10 µm. FIG. 5B shows maximum numbers of crossings ($N_{max}$) of the Sholl plots demonstrate that tetrahydroazepine-containing ibogalogs are more effective at increasing dendritic arbor complexity than are isoquinuclicine-containing ibogalogs.

FIG. 7 shows ibogaine hydrochloride exhibits limited solubility in various saline-based vehicles. Solutions of saline (0.9%) containing various percentages of co-solvents/additives were added to finely crushed ibogaine hydrochloride. All attempts to improve its solubility through pulverizing, sonication, and mild heating (<50° C.) were unsuccessful. Moreover, the addition of co-solvents (ethanol, dimethyl sulfoxide, glycerol), surfactants (Kolliphor), or hydrotropes (ATP) to the vehicle did not substantially improve its solubility. It was confirmed the purity and identity of the ibogaine hydrochloride used in these studies through a combination of NMR, LC-MS, and X-ray crystallography experiments.

FIG. 11A shows proportion of viable and non-viable (malformed+dead) zebrafish following treatment with VEH and TBG (66 µM) for 5 dpf (Fisher's exact test: p=0.3864) FIG. 11B shows representative images of zebrafish treated with VEH and TBG (66 µM) for 2 and 5 dpf. Scale bar=2 mm.

FIG. 13 shows pharmacological profiles of ibogalogs and related compounds. Table showing $EC_{50}$ and E max estimates from at least two independent concentration-response curves performed in duplicate or triplicate. Log(E max/ $EC_{50}$) activity is included as an estimate of system agonist activity; Inactive=inactive in agonist mode; N.D.=not determined; blue boxes=exhibits antagonist activity; dark grey boxes=inactive in agonist mode but not tested in antagonist mode; orange boxes indicate inverse agonist.

DETAILED DESCRIPTION OF THE INVENTION

I. General

Figure 2A:
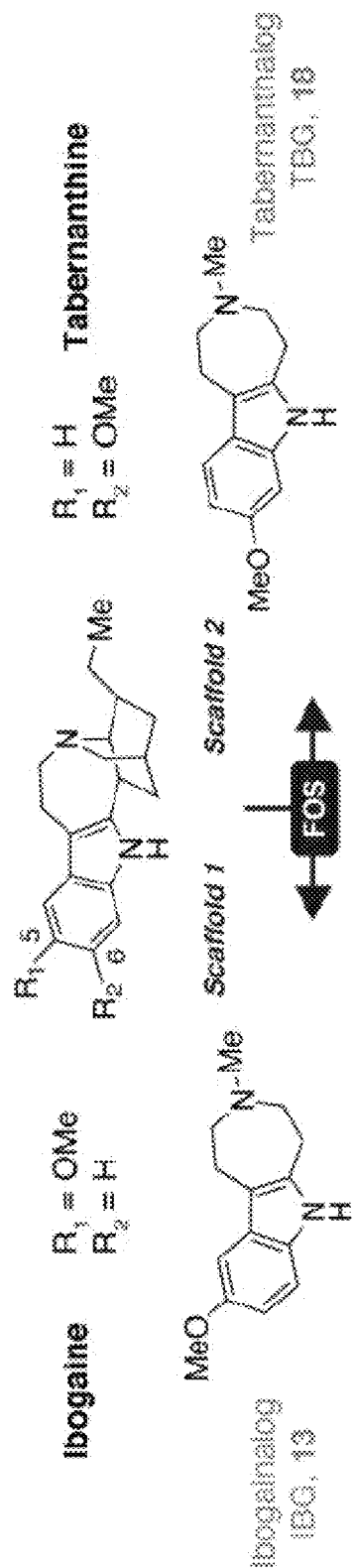

Ibogaine has garnered attention as a potential plasticity-promoting anti-addictive agent; a single dose of this hallucinogenic compound has demonstrated sustained efficacy for treating addiction to alcohol, opiates, nicotine, and psychostimulants. An analog of ibogaine capable of promoting fibroblast growth factor 2 (FGF2)-induced GDNF release in C6 glioma cells was developed; however, the effects of this compound on neural plasticity are not known.

Ibogaine is highly plasticity-promoting. However, ibogaine's hallucinogenic effects present barriers to regulatory approval and severely limits its therapeutic potential. It is possible to decouple the hallucinogenic effects of a drug from its ability to promote neural plasticity. Compounds described herein, lacking the isoquinuclidine of ibogaine and transposing the methoxy group from the 5- to the 6-position of the indole, are non-hallucinogenic ibogaine derivatives that, for example promote neuronal growth.

Compounds capable of modifying neural circuits that control motivation, anxiety, and drug-seeking behavior have potential for treating depression, post-traumatic stress disorder (PTSD), and substance abuse disorder (SUD). In some instances, such psychoplastogenic medicines produce sustained therapeutic effects because the medicines treat the underlying pathological changes in circuitry. Psychedelic compounds have distinguished themselves in this regard because, for example, they promote structural and functional neural plasticity in key circuits, elicit therapeutic responses in multiple neuropsychiatric disorders, and produce beneficial effects that last for months following a single administration.

Described herein are water soluble, non-hallucinogenic, analogs of ibogaine. Despite lacking hallucinogenic properties, compounds described herein promote structural neural plasticity, reduce alcohol consumption, and produce antidepressant-like effects in mice.

In some instances, hallucinogenic $5\text{-}HT_{2A}$ agonists (e.g., DMT, LSD, DOI, etc.) are useful for treating neurological diseases, such as neuropsychiatric diseases. (Ly et al., 2018.) However, the hallucinogenic and dissociative potential of such compounds has limited the use of these compounds in the clinic. $5\text{-}HT_{2A}$ antagonists abrogate the neuritogenesis and spinogenesis effects of hallucinogenic compounds with $5\text{-}HT_{2A}$ agonist activity, e.g., DMT, LSD, and DOI, demonstrating the correlation of $5\text{-}HT_{2A}$ agonism and the promotion of neural plasticity (Ly et al., 2018; Dunlap et al., 2020).

Provided herein in some embodiments are non-hallucinogenic psychoplastogens. In some embodiments, the non-hallucinogenic ibogaine analogs described herein have improved physiochemical properties as a result of, for example, decreasing total polar surface area. Described herein in some embodiments are non-hallucinogenic compounds that demonstrate similar therapeutic potential as hallucinogenic $5\text{-}HT_{2A}$ agonists. In some embodiments, the non-hallucinogenic compounds described herein provide better therapeutic potential than hallucinogenic $5\text{-}HT_{2A}$ modulators for neurological diseases.

The present invention provides azepino-indoles and other heterocyclic non-hallucinogenic compounds useful for the treatment of a variety of brain disorders and other conditions, as well as increasing neuronal plasticity, or increasing at least one of translation, transcription, or secretion of neurotrophic factors.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

"A," "an," or "the" not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

Abbreviations. VEH=vehicle; KET=ketamine; IBO=ibogaine; NOR=noribogaine; IBG=ibogainalog; TBG=tabernanthalog; KETSN=ketanserin; SI=sertindole; DOI=2,5-dimethoxy-4-iodoamphetamine; FST=forced swim test; EtOH=ethanol, DMSO=dimethyl sulfoxide, ATP=adenosine triphosphate.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Cycloalkyl" refers to a saturated or partially unsaturated, monocyclic, bicyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Bicyclic compounds include spirocyclic compounds, fused bicyclic compounds and bridged bicyclic compounds. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Heterocycloalkyl" refers to a cycloalkyl as defined above, having from 3 to 12 ring members and from 1 to 4 heteroatoms of N, O and S. Heterocycloalkyl includes bicyclic compounds which include a heteroatom. Bicyclic compounds includes spirocyclic compounds, fused bicyclic compounds, and bridged bicyclic compounds The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (═O), among many others.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heterocycloalkyl component is as defined above. Alkyl-heterocycloalkyl groups can be substituted or unsubstituted.

"Halogen" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. In some instances, the term "perfluoro" can be used to define a compound or radical where all the hydrogens are replaced with fluorine. For example, perfluoromethyl refers to 1,1,1-tri fluorom ethyl. Alkyl amine "Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Haloalkoxy" refers to an alkoxy group where some or all of the hydrogen atoms are substituted with halogen atoms.

As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Amine" refers to an —N(R)$_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen).

"Alkyl amine" refers to an alkyl group as defined within, having one or more amino groups. The amino groups can be primary, secondary or tertiary. The alkyl amine can be further substituted with a hydroxy group to form an aminohydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The aryl component is as defined above. Examples of alkyl-aryl groups include, but are not limited to, benzyl and ethyl-benzene. Alkyl-aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Heteroaryl groups can include any number of ring atoms, such as, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heteroaryl component is as defined within. Alkyl-heteroaryl groups can be substituted or unsubstituted.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (fumaric acid, acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Pharmaceutically acceptable salt" refers to a compound in salt form, wherein the compound are suitable for administration to a subject. Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like "Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

"Composition" refers to a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation.

"Isomers" refers to compounds with same chemical formula but different connectivity between the atoms in the molecule, leading to distinct chemical structures. Isomers include structural isomers and stereoisomers. Examples of structural isomers include, but are not limited to tautomers and regioisomers. Examples of stereoisomers include but are not limited to diastereomers and enantiomers.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Subject" refers to animals such as mammals, including, but not limited to, primates (e.g., humans), cows, sheep, goats, horses, dogs, cats, rabbits, rats, mice and the like. In certain embodiments, the subject is a human.

"Therapeutically effective amount" or "therapeutically sufficient amount" or "effective or sufficient amount" refers to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

"Neuronal plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses.

"Brain disorder" refers to a neurological disorder which affects the brain's structure and function. Brain disorders can include, but are not limited to, Alzheimer's, Parkinson's disease, psychological disorder, depression, treatment resistant depression, addiction, anxiety, post-traumatic stress disorder, suicidal ideation, major depressive disorder, bipolar disorder, schizophrenia, stroke, traumatic brain injury, and substance use disorder.

"Combination therapy" refers to a method of treating a disease or disorder, wherein two or more different pharmaceutical agents are administered in overlapping regimens so that the subject is simultaneously exposed to both agents. For example, the compounds of the invention can be used in combination with other pharmaceutically active compounds. The compounds of the invention can be administered simultaneously (as a single preparation or separate preparation) or sequentially to the other drug therapy. In general, a combination therapy envisions administration of two or more drugs during a single cycle or course of therapy.

"Neurotrophic factors" refers to a family of soluble peptides or proteins which support the survival, growth, and differentiation of developing and mature neurons.

"Modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT_{2A}$) are modulators of the receptor.

"Agonism" refers to the activation of a receptor or enzyme by a modulator, or agonist, to produce a biological response.

"Agonist" refers to a modulator that binds to a receptor or enzyme and activates the receptor to produce a biological response. By way of example only, "$5HT_{2A}$ agonist" can be used to refer to a compound that exhibits an $EC_{50}$ with respect to $5HT_{2A}$ activity of no more than about 100 µM. In some embodiments, "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

"Positive allosteric modulator" refers to a modulator that binds to a site distinct from the orthosteric binding site and enhances or amplifies the effect of an agonist.

"Antagonism" refers to the inactivation of a receptor or enzyme by a modulator, or antagonist. Antagonism of a receptor, for example, is when a molecule binds to the receptor and does not allow activity to occur.

"Antagonist" or "neutral antagonist" refers to a modulator that binds to a receptor or enzyme and blocks a biological response. An antagonist has no activity in the absence of an agonist or inverse agonist but can block the activity of either, causing no change in the biological response.

"$IC_{50}$" refers to the concentration of a substance (e.g., a compound or a drug) that is required for 50% inhibition of a biological process. For example, $IC_{50}$ refers to the half maximal (50%) inhibitory concentration (IC) of a substance as determined in a suitable assay. In some instances, an $IC_{50}$ is determined in an in vitro assay system. In some embodiments as used herein, $IC_{50}$ refers to the concentration of a modulator (e.g., an antagonist or inhibitor) that is required for 50% inhibition of a receptor, for example, $5HT_{2A}$.

III. Compounds

The present invention provides azepino-indoles and other heterocyclic non-hallucinogenic compounds (e.g., Formula (I) or Formula (Ia)) useful for the treatment of a variety of brain disorders and other conditions. In some embodiments, azepino-indoles and other heterocyclic compounds provided herein are $5-HT_{2A}$ modulators and promote neural plasticity (e.g., cortical structural plasticity).

In some embodiments, the present invention provides a compound of Formula I:

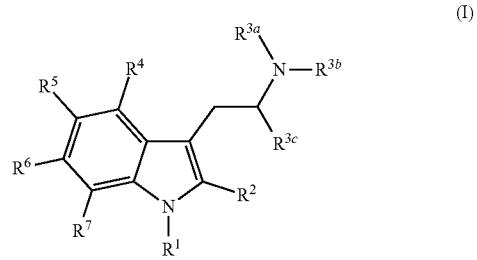

wherein: $R^1$ is hydrogen or $C_{1-6}$ alkyl; $R^{3a}$ and $R^{3b}$ are each independently hydrogen, $C_{1-6}$ alkyl, $C_{3-8}$ cycloalkyl, or $C_{4-14}$ alkyl-cycloalkyl; $R^{3c}$ is hydrogen or $C_{1-6}$ alkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O; alternatively, $R^2$ and $R^{3c}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O; $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —C(O)$R^{8b}$, —C(O)$OR^{8b}$, —OC(O)$R^{8b}$, —OC(O)$OR^{8b}$, —N($R^{8b}R^{8c}$), —N($R^{8b}$)C(O)$R^{8c}$, —C(O)N($R^{8b}R^{8c}$), —N($R^{8b}$)C(O)$OR^{8c}$, —OC(O)N($R^{8b}R^{8c}$), —N($R^{8b}$)C(O)N($R^{8c}R^{8d}$), —C(O)C(O)N($R^{8b}R^{8c}$), —S($O_2$)$R^{8b}$, —S(O)$_2$N($R^{8b}R^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl or $C_{5-10}$ heteroaryl; $R^{8a}$, $R^{8b}$, $R^{8c}$ and $R^{8d}$ are each independently H, $C_{1-6}$ alkyl; wherein when $R^2$ and $R^{3b}$ are combined with the atoms to which they are attached to form a $C_7$ heterocycloalkyl, and $R^{3a}$ is methyl, then $R^5$ is not OMe, OH, or Cl; wherein when $R^2$ and $R^{3b}$ are combined with the atoms to which they are attached to form a $C_7$ heterocycloalkyl, and $R^{3a}$ is ethyl, then $R^6$ is not OMe; wherein when $R^2$ and $R^{3b}$ are combined with the atoms to which they are attached to form a $C_7$ heterocycloalkyl, and $R^6$ is F, then at least one of $R^4$, $R^5$, and $R^7$ is not hydrogen; wherein when $R^2$ and $R^{3b}$ are combined with the atoms to which they are attached to form a $C_7$ heterocycloalkyl, and $R^6$ is F, Cl, -Me, or —OMe, then $R^{3a}$ is-Me; wherein when $R^2$ and $R^{3b}$ are combined with the atoms to which they are attached to form a $C_6$ heterocycloalkyl, and $R^6$ is $C_{1-6}$ alkyl, halogen, $C_{1-6}$ alkyoxy, —C(O)H, —$NH_2$, then at least one of $R^4$, $R^5$, and $R^7$ is not hydrogen; and wherein when $R^2$ and $R^{3b}$ are combined with the atoms to which they are attached to form a $C_6$ heterocycloalkyl, and $R^6$ is methyl, halogen, or —C(O)H, then at least one of $R^4$, $R^5$, and $R^7$ is not methyl or Cl, or pharmaceutically acceptable salts and isomers thereof.

In some embodiments, the present invention provides a compound of Formula I

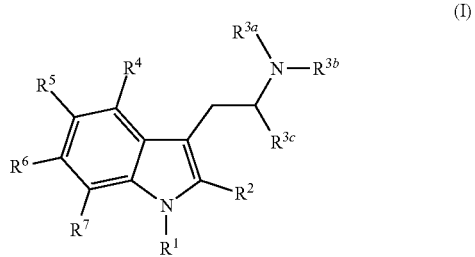

(I)

wherein $R^1$ is hydrogen or $C_{1-6}$ alkyl; $R^{3a}$ and $R^{3b}$ are each independently hydrogen, $C_{1-6}$ alkyl, $C_{3-8}$ cycloalkyl, or $C_{4-14}$ alkyl-cycloalkyl; $R^{3c}$ is hydrogen or $C_{1-6}$ alkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O; alternatively, $R^2$ and $R^{3b}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O; $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —C(O)$R^{8b}$, —C(O)$OR^{8b}$, —OC(O)$R^{8b}$, —OC(O)$OR^{8b}$, —N($R^{8b}R^{8c}$), —N($R^{8b}$)C(O)$R^{8c}$, —C(O)N($R^{8b}R^{8c}$), —N($R^{8b}$)C(O)$OR^{8c}$, —OC(O)N($R^{8b}R^{8c}$), —N($R^{8b}$)C(O)N($R^{8c}R^{8d}$), —C(O)C(O)N($R^{8b}R^{8c}$), —S($O_2$)$R^{8b}$, —S(O)$_2$N($R^{8b}R^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H; $R^{8b}$, $R^{8c}$ and $R^{8d}$ are each independently H or $C_{1-6}$ alkyl; or pharmaceutically acceptable salts and isomers thereof.

In some embodiments, $R^1$ is hydrogen or $C_{1-6}$ alkyl. In some embodiments, $R^1$ is hydrogen, methyl, ethyl, or propyl. In some embodiments, $R^1$ is hydrogen or methyl. In some embodiments, $R^1$ is hydrogen. In some embodiments, $R^1$ is methyl. In some embodiments, the present invention provides a compound, or a pharmaceutically acceptable salt thereof, wherein $R^1$ is hydrogen or methyl. In some embodiments, the present invention provides a compound, or a pharmaceutically acceptable salt thereof, wherein $R^1$ is hydrogen.

In some embodiments, $R^{3a}$ is hydrogen, $C_{1-6}$ alkyl, $C_{3-8}$ cycloalkyl, or $C_{4-14}$ alkyl-cycloalkyl. In some embodiments, $R^{3a}$ is hydrogen or $C_{1-6}$ alkyl. In some embodiments, $R^{3a}$ is hydrogen, methyl, ethyl, or propyl. In some embodiments, $R^{3a}$ is hydrogen or methyl. In some embodiments $R^{3a}$ is methyl. In some embodiments, $R^{3a}$ is hydrogen. In some embodiments, the present invention provides a compound, or a pharmaceutically acceptable salt thereof, wherein $R^{3a}$ is hydrogen or $C_{1-6}$ alkyl. In some embodiments, the present invention provides a compound, or a pharmaceutically acceptable salt thereof, wherein $R^{3a}$ is hydrogen or methyl.

In some embodiments, $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —C(O)$R^{8b}$, —C(O)$OR^{8b}$, —OC(O)$R^{8b}$, —OC(O)$OR^{8b}$, —N($R^{8b}R^{8c}$), —N($R^{8b}$)C(O)$R^{8c}$, —C(O)N($R^{8b}R^{8c}$), —N($R^{8b}$)C(O)$OR^{8c}$, —OC(O)N($R^{8b}R^{8c}$), —N($R^{8b}$)C(O)N($R^{8c}R^{8d}$), —C(O)C(O)N($R^{8b}R^{8c}$), —S($O_2$)$R^{8b}$, —S(O)$_2$N($R^{8b}R^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl or $C_{5-10}$ heteroaryl; and $R^{8a}$, $R^{8b}$, $R^{8c}$ and $R^{8d}$ are each independently H, $C_{1-6}$ alkyl.

In some embodiments, the present invention provides a compound, or a pharmaceutically acceptable salt thereof, wherein: $R^4$, $R^5$, $R^6$ and $R^7$ are each independently hydrogen, $C_{1-6}$ alkyl, halogen, $C_{1-6}$ haloalkyl, $C_{1-6}$ alkoxy, $C_{1-6}$ haloalkoxy, —$OR^{8a}$, —$NO_2$, —CN, —$N(R^{8b}R^{8c})$, —$N(R^{8b})C(O)R^{8c}$, —$C(O)N(R^{8b}R^{8c})$, $C_{3-8}$ cycloalkyl, $C_{3-14}$ alkyl-cycloalkyl, $C_{4-10}$ heterocycloalkyl, or $C_{4-16}$ alkyl-heterocycloalkyl, wherein at least one of $R^4$, $R^5$, $R^6$ and $R^7$ is not H; alternatively, $R^4$ and $R^5$, $R^5$ and $R^6$, or $R^6$ and $R^7$ are combined with the atoms to which they are each attached to form a $C_{3-6}$ heterocycloalkyl; and $R^{8a}$, $R^{8b}$ or $R^{8c}$ are each independently H, $C_{1-6}$ alkyl, or $C_{3-6}$ cycloalkyl.

In some embodiments, the present invention provides a compound, or a pharmaceutically acceptable salt thereof, wherein $R^6$ is $C_{1-6}$ alkyl, halogen, $C_{1-6}$ haloalkyl, $C_{1-6}$ alkoxy, $C_{1-6}$ haloalkoxy, —$OR^{8a}$, —$NO_2$, —CN, —$N(R^{8b}R^{8c})$, —$N(R^{8b})C(O)R^{8c}$, —$C(O)N(R^{8b}R^{8c})$, $C_{3-8}$ cycloalkyl, $C_{3-14}$ alkyl-cycloalkyl, $C_{4-10}$ heterocycloalkyl, or $C_{4-16}$ alkyl-heterocycloalkyl; alternatively, $R^5$ and $R^6$ are combined with the atoms to which they are each attached to form a $C_{3-6}$ heterocycloalkyl; and $R^{8a}$, $R^{8b}$ and $R^{8c}$ are each independently H, $C_{1-6}$ alkyl, or $C_{3-6}$ cycloalkyl.

In some embodiments, the present invention provides a compound, or a pharmaceutically acceptable salt thereof, wherein $R^4$, $R^5$, $R^6$ and $R^7$ are each independently hydrogen, $C_{1-6}$ alkyl, halogen, $C_{1-6}$ haloalkyl, $C_{1-6}$ alkoxy, $C_{1-6}$ haloalkoxy, —$OR^{8a}$, —$N(R^{8b}R^{8c})$, —$N(R^{8b})C(O)R^{8c}$, $C_{4-10}$ heterocycloalkyl, or $C_{4-16}$ alkyl-heterocycloalkyl, wherein at least one of $R^4$, $R^5$, $R^6$ and $R^7$ is not H; alternatively, $R^5$ and $R^6$ are combined with the atoms to which they are each attached to form a $C_{3-6}$ heterocycloalkyl; and $R^{8a}$, $R^{8b}$ and $R^{8c}$ are each independently H, $C_{1-6}$ alkyl, or $C_{3-6}$ cycloalkyl.

In some embodiments, the present invention provides a compound, or a pharmaceutically acceptable salt thereof, wherein: $R^6$ is $C_{1-6}$ alkyl, halogen, $C_{1-6}$ haloalkyl, $C_{1-6}$ alkoxy, $C_{1-6}$ haloalkoxy, —$OR^{8a}$, —$N(R^{8b}R^{8c})$, —$N(R^{8b})C(O)R^{8c}$, $C_{4-10}$ heterocycloalkyl, or $C_{4-16}$ alkyl-heterocycloalkyl; alternatively, $R^5$ and $R^6$ are combined with the atoms to which they are each attached to form a $C_{3-6}$ heterocycloalkyl; and $R^{8a}$, $R^{8b}$ and $R^{8c}$ are each independently H, $C_{1-6}$ alkyl, or $C_{3-6}$ cycloalkyl.

In some embodiments, the present invention provides a compound, or a pharmaceutically acceptable salt thereof, wherein: $R^4$, $R^5$, $R^6$ and $R^7$ are each independently hydrogen, $C_{1-6}$ alkyl, halogen, $C_{1-6}$ haloalkyl, $C_{1-6}$ alkoxy, $C_{1-6}$ haloalkoxy, —$OR^{8a}$, —$N(R^{8b}R^{8c})$, or —$N(R^{8b})C(O)R^{8c}$ wherein at least one of $R^4$, $R^5$, $R^6$ and $R^7$ is not H; $R^{8a}$ is H; and $R^{8b}$ and $R^{8c}$ are each independently H or -Me; alternatively, $R^5$ and $R^6$ are combined with the atoms to which they are each attached to form a $C_{3-6}$ heterocycloalkyl.

In some embodiments, the present invention provides a compound, wherein $R^4$, $R^5$, $R^6$ and $R^7$ are each independently hydrogen, $C_{1-6}$ alkyl, halogen, $C_{1-6}$ haloalkyl, $C_{1-6}$ alkoxy, $C_{1-6}$ haloalkoxy, or —$OR^{8a}$, wherein at least one of $R^4$, $R^5$, $R^6$ and $R^7$ is not H; and $R^{8a}$ is H; alternatively, $R^5$ and $R^6$ can be combined with the atoms to which they are each attached to form a $C_{3-6}$ heterocycloalkyl.

In some embodiments, the present invention provides a compound, or a pharmaceutically acceptable salt thereof, wherein: $R^4$, $R^5$, $R^6$ and $R^7$ are each independently H, F, Cl, Br, —OH, —OMe, —$CF_3$—$OCF_3$, -Me, —$NMe_2$, —NHC(O)Me, or —N(Me)C(O)Me, wherein at least one of $R^4$, $R^5$, $R^6$ and $R^7$ is not H; alternatively, $R^5$ and $R^6$ are combined to form a 1,3-dioxole ring, or 1,4-dioxane ring.

In some embodiments, the present invention provides a compound, or a pharmaceutically acceptable salt thereof, wherein: $R^4$ is H, F, -Me, —$CF_3$, —$OCF_3$, or —OMe; $R^5$ is H, F, Cl, Br, -Me, —$CF_3$, —$OCF_3$, —OH or —OMe; $R^6$ is H, F, —OH, —OMe, -OiPr, -Me, —$CF_3$, —$OCF_3$, —$NMe_2$, —NHC(O)Me, or —N(Me)C(O)Me; alternatively, $R^5$ and $R^6$ are combined to form a 1,3-dioxole ring or 1,4-dioxane ring; and $R^7$ is H, wherein at least one of $R^4$, $R^5$ and $R^6$ is not H.

In some embodiments, the present invention provides a compound, wherein $R^4$, $R^5$, $R^6$ and $R^7$ are each independently H, F, Cl, Br, —OH, —OMe, —$CF_3$ or —$OCF_3$, wherein at least one of $R^4$, $R^5$, $R^6$ and $R^7$ is not H; alternatively, $R^5$ and $R^6$ are combined to form a 1,3-dioxole ring.

In some embodiments, the present invention provides a compound, wherein $R^4$ is H, F, or —OMe; $R^5$ is H, F, Cl, Br, —OH or —OMe; $R^6$ is H, F, —OMe, —$CF_3$ or —$OCF_3$; alternatively, $R^5$ and $R^6$ are combined to form a 1,3-dioxole ring; and $R^7$ is H, wherein at least one of $R^4$, $R^5$, $R^6$ and $R^7$ is not H.

In some embodiments, the present invention provides a compound, or a pharmaceutically acceptable salt thereof, wherein $R^6$ is F, —OH, —OMe, -OiPr, -Me, —$CF_3$, —$OCF_3$, —$NMe_2$, —NHC(O)Me, or —N(Me)C(O)Me; alternatively, $R^5$ and $R^6$ are combined to form a 1,3-dioxole ring or 1,4-dioxane ring.

In some embodiments, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl or $C_{5-10}$ heteroaryl. In some embodiments, $R^4$ and $R^5$, $R^5$ and $R^6$, or $R^6$ and $R^7$ are combined with the atoms to which they are each attached to form a $C_{3-6}$ cycloalkyl or $C_{3-6}$ heterocycloalkyl. In some embodiments, $R^4$ and $R^5$ are combined with the atoms to which they are each attached to form a $C_{3-6}$ heterocycloalkyl. In some embodiments, $R^5$ and $R^6$ are combined with the atoms to which they are each attached to form a $C_{3-6}$ heterocycloalkyl. In some embodiments, $R^6$ and $R^7$ are combined with the atoms to which they are each attached to form a $C_{3-6}$ heterocycloalkyl. In some embodiments, $R^5$ and $R^6$ are combined to form a 1,3-dioxole ring or 1,4-dioxane ring.

In some embodiments, $R^{3a}$ and $R^{3b}$ are each independently hydrogen, $C_{1-6}$ alkyl, $C_{3-8}$ cycloalkyl, or $C_{4-14}$ alkyl-cycloalkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O; alternatively, $R^2$ and $R^{3c}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O.

In some embodiments, the present invention provides a compound of the present invention, or a pharmaceutically acceptable salt thereof, wherein $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O. In some embodiments, the present invention provides a compound, or a pharmaceutically acceptable salt thereof, wherein $R^2$ and $R^{3b}$ are combined with the atoms to which they are attached to form a $C_{5-8}$ heterocycloalkyl. In some embodiments, the present invention provides a compound, or a pharmaceutically acceptable salt thereof, wherein $R^2$ and $R^{3b}$ are combined with the atoms to which they are attached to form a $C_{7-8}$ heterocycloalkyl.

In some embodiments, the present invention provides a compound, or a pharmaceutically acceptable salt thereof, wherein the compound of Formula I has the following structure:

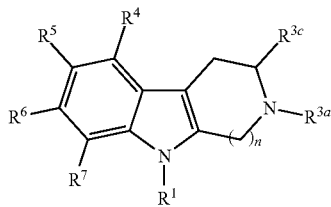

wherein: $R^6$ is $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl or $C_{5-10}$ heteroaryl; $R^{8a}$, $R^{8b}$, $R^{8c}$ and $R^{8d}$ are each independently H, $C_{1-6}$ alkyl; and n is 1, 2, or 3; wherein when n is 2, and $R^6$ is F, then at least one of $R^4$, $R^5$, and $R^7$ is not hydrogen; wherein when n is 2 and $R^6$ is F, Cl, methyl, or OMe, then $R^{3a}$ is methyl; wherein when n is 1, and $R^6$ is $C_{1-6}$ alkyl, halogen, $C_{1-6}$ alkyoxy, —C(O)H, —$NH_2$, then at least one of $R^4$, $R^5$, and $R^7$ is not hydrogen; and wherein when n is 1, and $R^6$ is methyl, halogen, or —C(O)H, then at least one of $R^4$, $R^5$, and $R^7$ is not methyl or Cl.

In some embodiments, the present invention provides a compound of Formula (Ia), or a pharmaceutically acceptable salt or isomer thereof, wherein the compound has the following structure:

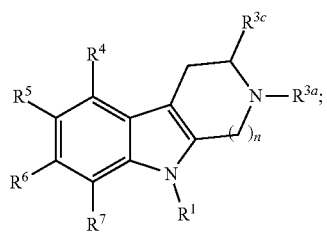

wherein: $R^1$ is hydrogen or $C_{1-6}$ alkyl; $R^{3a}$ is hydrogen, $C_{1-6}$ alkyl, $C_{3-8}$ cycloalkyl, or $C_{4-14}$ alkyl-cycloalkyl $R^{3c}$ is hydrogen or $C_{1-6}$ alkyl; $R^4$, $R^5$, and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^6$ is $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; alternatively, $R^4$ and $R^5$, $R^5$ and $R^6$, or $R^6$ and $R^7$, can be combined with the atoms to which they are each attached to form a $C_{3-8}$ cycloalkyl or a $C_{3-6}$ heterocycloalkyl; $R^{8a}$, $R^{8b}$, $R^{8c}$, and $R^{8d}$ are each independently hydrogen, $C_{1-6}$ alkyl, or $C_{3-6}$ cycloalkyl; n is 1, 2, or 3; or salts and isomers thereof; and wherein when n is 1 and $R^6$ is $C_{1-6}$ alkyl, halo, C(O)H, $NH_2$, or $C_{1-6}$ alkoxy, then at least one of $R^4$, $R^5$, and $R^7$ is not hydrogen; wherein when n is 1 and $R^6$ is methyl, halogen, or C(O)H, then at least one of $R^4$, $R^5$, or $R^7$ is not methyl or Cl; wherein when n is 2 and $R^6$ is F, Cl, methyl, or OMe, then $R^{3a}$ is methyl; and wherein when n is 2 and $R^6$ is F, then at least one of $R^4$, $R^5$, and $R^7$ is not hydrogen.

In some embodiments, the present invention provides a compound, or a pharmaceutically acceptable salt thereof, wherein the compound of Formula I or Ia has the following structure:

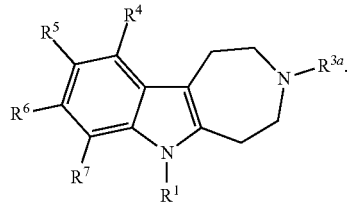

In some embodiments, $R^{3a}$ is methyl, and $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O. In some embodiments, $R^{3a}$ is methyl, and $R^2$ and $R^{3b}$ are combined with the atoms to which they are attached to form a $C_{6-7}$ heterocycloalkyl.

In some embodiments, the present invention provides a compound, or a pharmaceutically acceptable salt thereof, wherein $R^{3a}$ is methyl. In some embodiments, the present invention provides a compound, or a pharmaceutically acceptable salt thereof, wherein the compound of Formula I or Ia has the following structure:

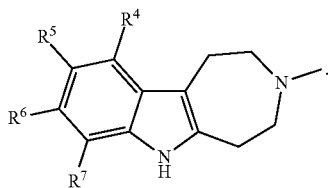

In some embodiments, the present invention provides a compound, or a pharmaceutically acceptable salt thereof, wherein the compound of Formula I or Ia has the following structure:

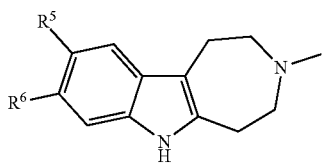

wherein: $R^5$ and $R^6$ are each independently H, F, Cl, Br, I, —OH, —OMe, -OiPr, -Me, —CF$_3$, —OCF$_3$, —NMe$_2$, —NHC(O)Me, or —N(Me)C(O)Me, wherein at least one of $R^5$ and $R^6$ is not H; alternatively, $R^5$ and $R^6$ are combined to form a 1,3-dioxole ring or 1,4-dioxane ring.

In some embodiments, the present invention provides a compound, or a pharmaceutically acceptable salt thereof, wherein the compound of Formula I or Ia has the following structure:

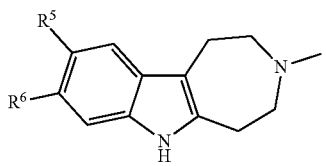

wherein: $R^5$ and $R^6$ are each independently F, Cl, Br, I, —OH, —OMe, -OiPr, -Me, —CF$_3$, —OCF$_3$, —NMe$_2$, —NHC(O)Me, or —N(Me)C(O)Me; alternatively, $R^5$ and $R^6$ are combined to form a 1,3-dioxole ring or 1,4-dioxane ring.

In some embodiments, the present invention provides a compound, wherein the compound of Formula I or Ia has the following structure:

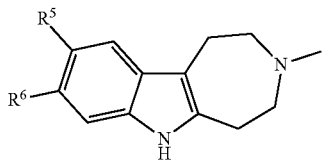

wherein $R^5$ is H, F, Cl, Br, —OH or —OMe; and $R^6$ is H, F, —OMe, —CF$_3$ or —OCF$_3$, wherein at least one of $R^5$ and $R^6$ is not H.

In some embodiments, the present invention provides a compound, or a pharmaceutically acceptable salt thereof, wherein the compound of Formula I or Ia has the following structure:

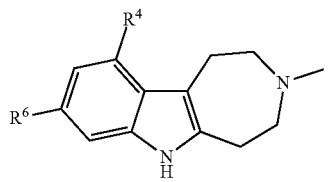

wherein: $R^4$ and $R^6$ are each independently H, F, Cl, Br, I, —OH, —OMe, -OiPr, -Me, —CF$_3$, —OCF$_3$, —NMe$_2$, —NHC(O)Me, or —N(Me)C(O)Me, wherein at least one of $R^4$ and $R^6$ is not H.

In some embodiments, the present invention provides a compound, or a pharmaceutically acceptable salt thereof, wherein the compound of Formula I or Ia has the following structure:

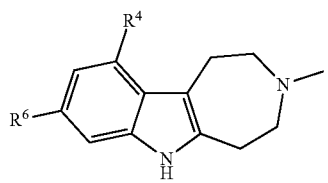

wherein: $R^4$ and $R^6$ are each independently F, Cl, Br, I, —OH, —OMe, -OiPr, -Me, —CF$_3$, —OCF$_3$, —NMe$_2$, —NHC(O)Me, or —N(Me)C(O)Me.

In some embodiments, the present invention provides a compound, wherein the compound is:

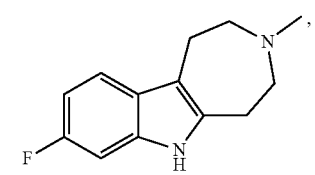

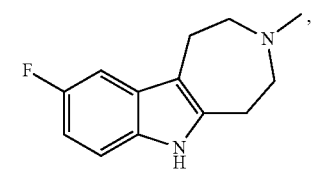

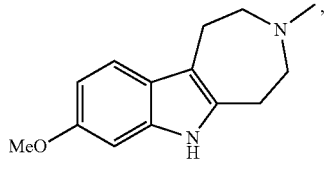

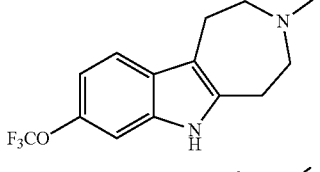

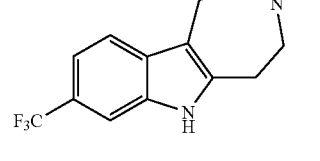

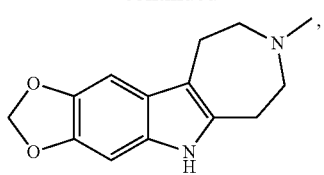
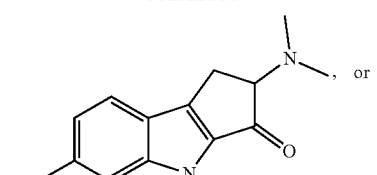
or a pharmaceutically acceptable salt thereof.
In some embodiments, the present invention provides a compound, or a pharmaceutically acceptable salt thereof, wherein the compound is

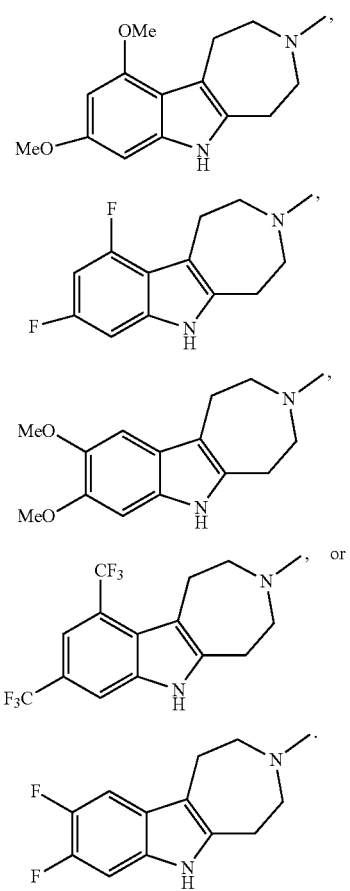
In some embodiments, the present invention provides a compound, or a pharmaceutically acceptable salt thereof, wherein the compound is
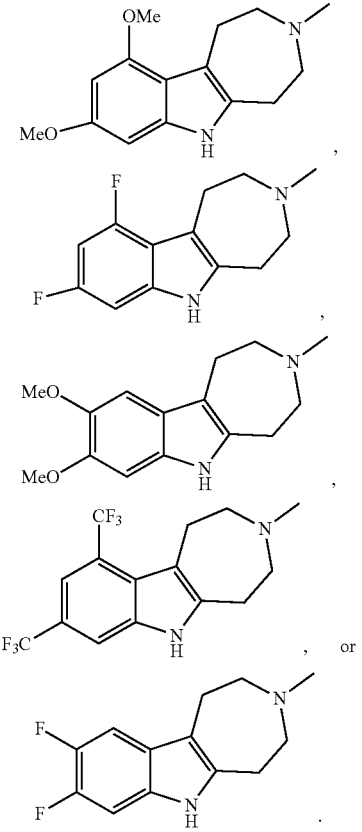
In some embodiments, the present invention provides a compound, or a pharmaceutically acceptable salt thereof, wherein the compound is
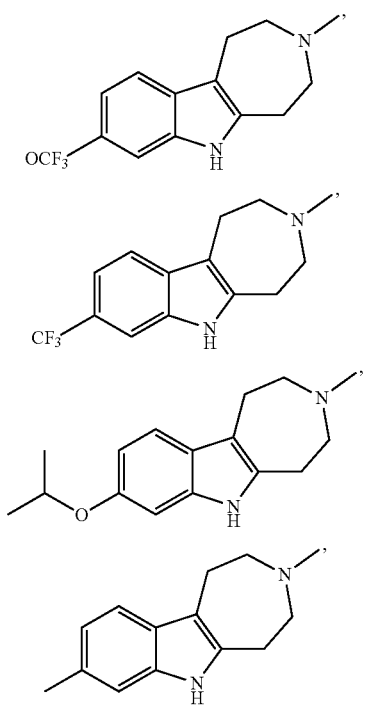

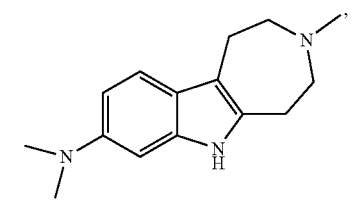
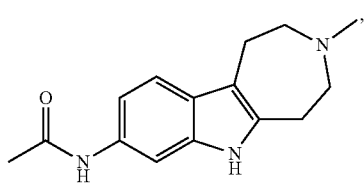
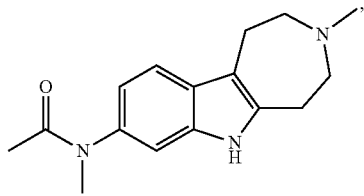
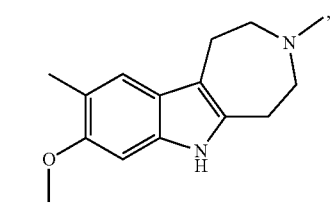
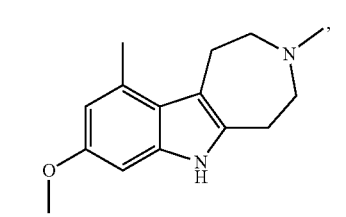
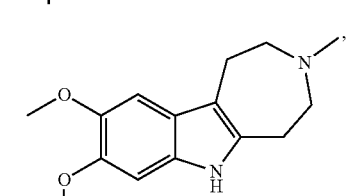
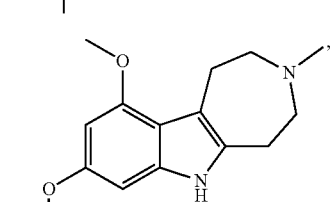
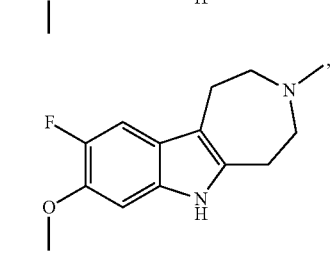
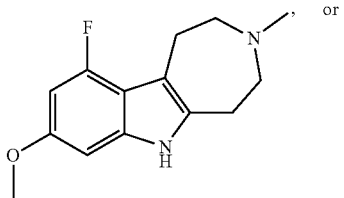
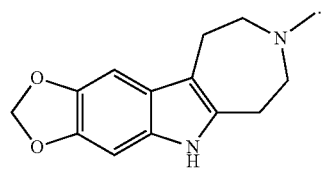
In some embodiments, the present invention provides a compound, or a pharmaceutically acceptable salt thereof, wherein the compound is
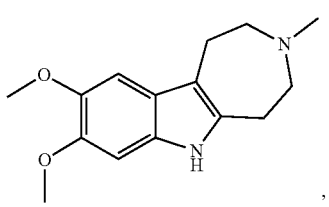
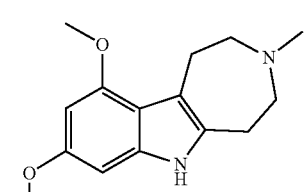
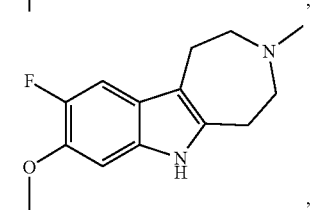
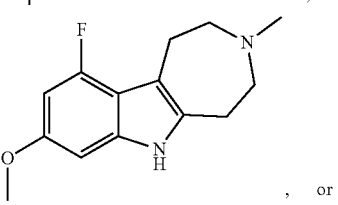
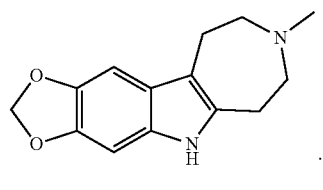
In some embodiments, the present invention provides a compound, or a pharmaceutically acceptable salt thereof, wherein the compound is

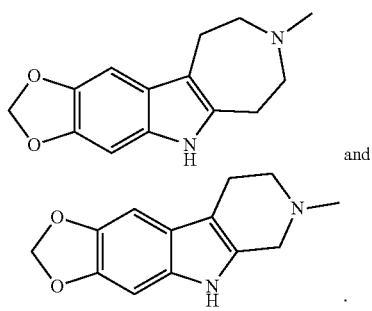

and

In some embodiments, $R^{3a}$ is hydrogen, and $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O. In some embodiments, $R^{3a}$ is hydrogen, and $R^2$ and $R^{3b}$ are combined with the atoms to which they are attached to form a $C_{6-7}$ heterocycloalkyl.

In some embodiments, the present invention provides a compound, or a pharmaceutically acceptable salt thereof, wherein the compound of Formula I or Ia has the following structure:

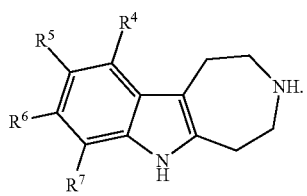

In some embodiments, the present invention provides a compound, or a pharmaceutically acceptable salt thereof, wherein the compound is

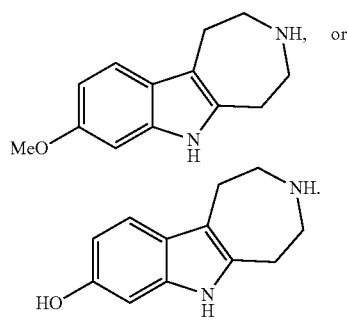

In some embodiments, $R^{3c}$ is hydrogen or $C_{1-6}$ alkyl. In some embodiments, $R^{3c}$ is hydrogen, methyl, ethyl, or propyl. In some embodiments $R^{3c}$ is hydrogen.

In some embodiments, $R^1$ is $C_{1-6}$ alkyl. In some embodiments, $R^1$ is methyl, ethyl, or propyl. In some embodiments, the present invention provides a compound, or a pharmaceutically acceptable salt thereof, wherein the compound of Formula I or Ia has the following structure:

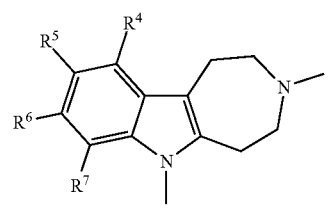

In some embodiments, the present invention provides a compound, or a pharmaceutically acceptable salt thereof, wherein the compound is

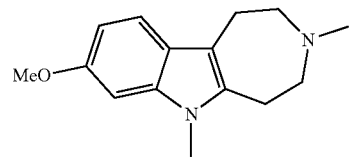

In some embodiments, the present invention provides a compound, or a pharmaceutically acceptable salt thereof, wherein $R^2$ and $R^{3c}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O.

In some embodiments, the present invention provides a compound, or a pharmaceutically acceptable salt thereof, wherein $R^2$ and $R^{3c}$ are combined with the atoms to which they are attached to form a $C_{5-6}$ cycloalkyl, substituted with 1 to 2 $R^{10}$ groups which are each hydrogen, or two $R^{10}$ groups attached to the same atom are combined to form =O.

In some embodiments, the present invention provides a compound, or a pharmaceutically acceptable salt thereof, wherein the compound is

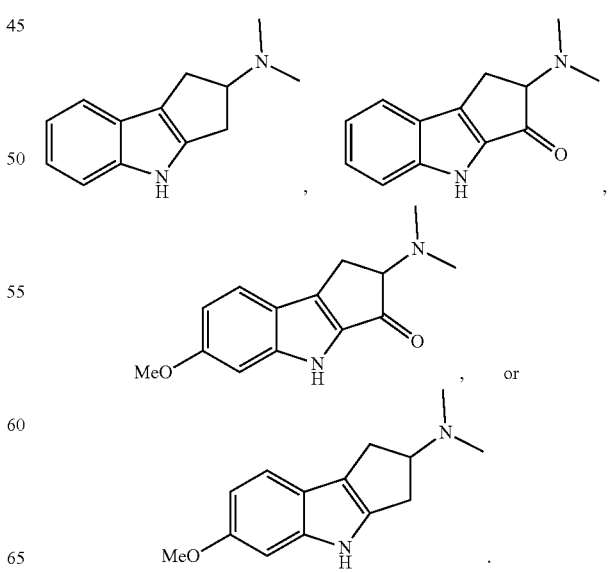

The compounds of the present invention can also be in the salt forms, such as acid or base salts of the compounds of the present invention. Illustrative examples of pharmaceutically acceptable salts are mineral acid (hydrochloric acid, hydrobromic acid, phosphoric acid, and the like) salts, organic acid (fumaric acid, acetic acid, propionic acid, glutamic acid, citric acid and the like) salts, quaternary ammonium (methyl iodide, ethyl iodide, and the like) salts. It is understood that the pharmaceutically acceptable salts are nontoxic. Additional information on suitable pharmaceutically acceptable salts can be found in Remington's Pharmaceutical Sciences, 17th ed., Mack Publishing Company, Easton, Pa., 1985, which is incorporated herein by reference.

The present invention also includes isotopically-labeled compounds of the present invention, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2$H, $^3$H, $^{13}$C, $^{14}$C, $^{15}$N, $^{18}$O, $^{17}$O, $^{18}$F, $^{35}$S and $^{36}$Cl).

Isotopically-labeled compounds of the present invention are useful in assays of the tissue distribution of the compounds and their prodrugs and metabolites; preferred isotopes for such assays include $^3$H and $^{14}$C. In addition, in certain circumstances substitution with heavier isotopes, such as deuterium ($^2$H), can provide increased metabolic stability, which offers therapeutic advantages such as increased in vivo half-life or reduced dosage requirements. Isotopically-labeled compounds of this invention can generally be prepared according to the methods known by one of skill in the art by substituting an isotopically-labeled reagent for a non-isotopically labeled reagent. Compounds of the present invention can be isotopically labeled at positions adjacent to the basic amine, in aromatic rings, and the methyl groups of methoxy substituents.

The present invention includes all tautomers and stereoisomers of compounds of the present invention, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

IV. Pharmaceutical Compositions and Formulations

In some embodiments, the present invention provides a pharmaceutical composition comprising a compound of the present invention, or a pharmaceutically acceptable salt thereof, and a pharmaceutically acceptable excipient.

The pharmaceutical compositions of the present invention can be prepared in a wide variety of oral, parenteral and topical dosage forms. Oral preparations include tablets, pills, powder, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Alter Asthma Immunol.* 75:107-111, 1995). Accordingly, the present invention also provides pharmaceutical compositions including a pharmaceutically acceptable carrier or excipient and the compounds of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% to 70% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In some embodiments, the pharmaceutical compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

V. Administration

The compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present invention can be present in any suitable amount, and can depend on various factors including, but not limited to, weight and age of the subject, state of the disease, etc. Suitable dosage ranges for the compound of the present invention include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

The compounds of the present invention can be co-administered with another active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present invention and the active agent can each be administered once a day, or two, three, or more times per day so as to provide the preferred dosage level per day.

In some embodiments, co-administration can be accomplished by co-formulation, i.e., preparing a single pharmaceutical composition including both the compound of the present invention and the active agent. In other embodiments, the compound of the present invention and the active agent can be formulated separately.

The compound of the present invention and the active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present invention and the other active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present invention and the active agent are suitable in the compositions and methods of the present invention.

VI. Methods of Treatment

The compounds of the present invention can be used for increasing neuronal plasticity. The compounds of the present invention can also be used to treat any brain disease. The compounds of the present invention can also be used for increasing at least one of translation, transcription or secretion of neurotrophic factors.

In some embodiments, a compound of the present invention is used to treat neurological diseases. In some embodiments, the compounds have, for example, anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder). In some embodiments, the neurological disease is a migraine or cluster headache. In some embodiments, the neurological disease is a neurodegenerative disorder, Alzheimer's disease, or Parkinson's disease. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, a compound of the present invention is used for increasing neuronal plasticity. In some embodiments, the compounds described herein are used for treating a brain disorder. In some embodiments, the compounds described herein are used for increasing at least one of translation, transcription, or secretion of neurotrophic factors.

Figure 15:
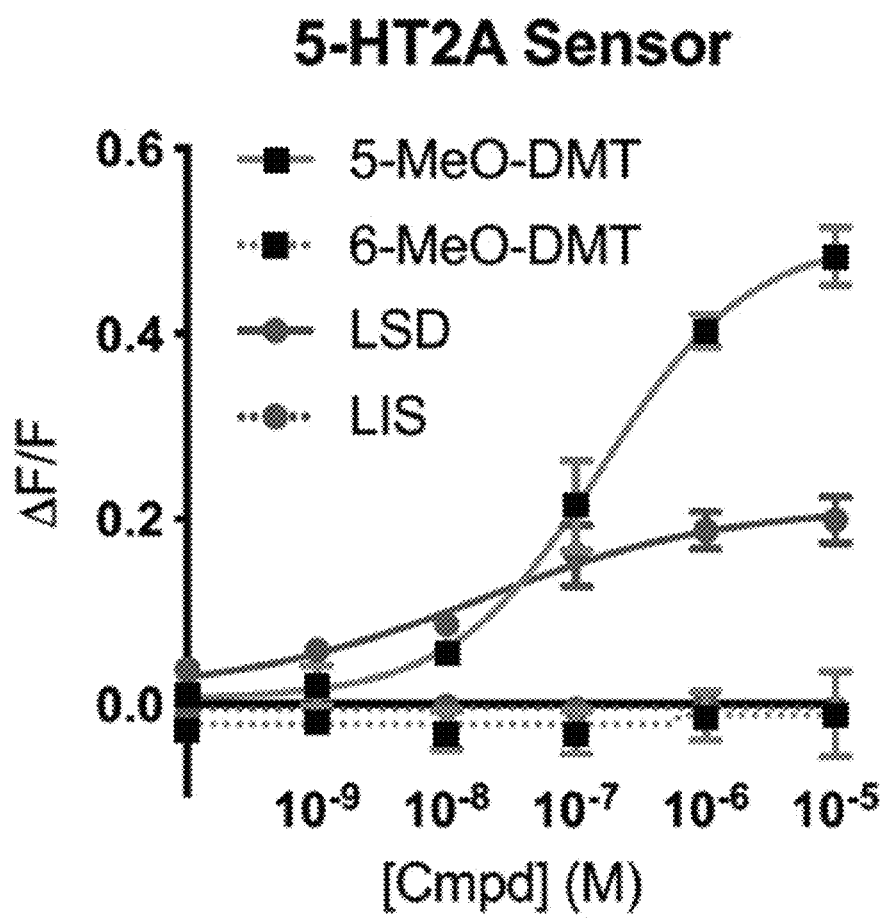
FIG. 15 shows the dose response profile of hallucinogenic and non-hallucinogenic compounds to a $5HT_{2A}$ sensor assay in agonist mode.
Figure 16:
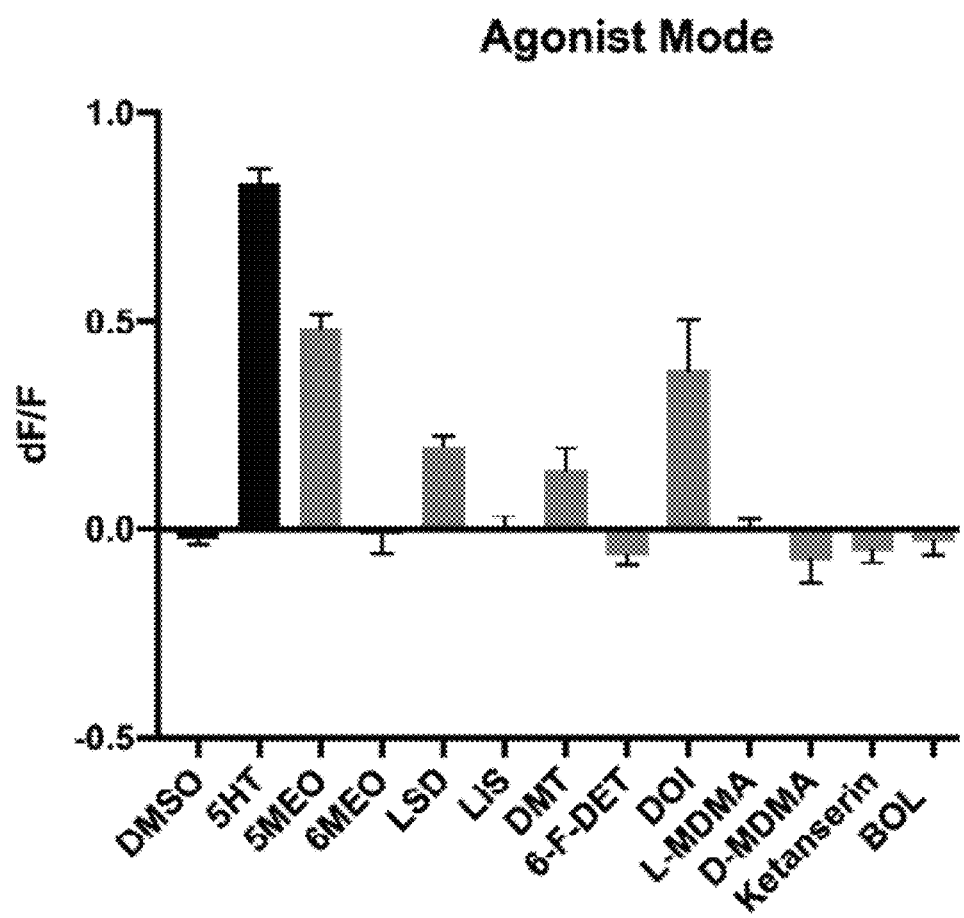
FIG. 16 shows the response profile of hallucinogenic and non-hallucinogenic compounds to a $5HT_{2A}$ sensor assay in agonist mode.

In some embodiments, the compounds of the present invention have activity as $5\text{-HT}_{2A}$ modulators. In some embodiments, the compounds of the present invention have activity as $5\text{-HT}_{2A}$ modulators. In some embodiments, the compounds of the present invention elicit a biological response by activating the $5\text{-HT}_{2A}$ receptor (e.g., allosteric modulation or modulation of a biological target that activates the $5\text{-HT}_{2A}$ receptor). $5\text{-HT}_{2A}$ agonism has been correlated with the promotion of neural plasticity (Ly et al., 2018). Hallucinogens (e.g., LSD and 5-MeO-DMT) activate a $5\text{HT}_{2A}$ sensor assay in agonist mode, but their non-hallucinogenic congeners (lisuride (LIS) and 6-MeO-DMT) do not (FIG. 15). Moreover, compounds, such as, for example, 5-MeO-DMT, LSD, DMT, DOI, which are hallucinogenic in animals (e.g., humans), activate the $5\text{HT}_{2A}$ sensor assay in agonist mode, whereas compounds, such as, for example, 6-MeO-DMT, LIS, 6-F-DET, L-MDMA, R-MDMA, Ketanserin, BOL148, which are non-hallucinogenic in animals (e.g., humans), do not activate the $5\text{HT}_{2A}$ sensor assay in agonist mode (FIG. 16, at 10 µM of compound). In some embodiments, hallucinogenic potential of a compound of the present invention is determined in vitro. In some embodiments, hallucinogenic potential of a compound of the present invention is determined using a $5HT_{2A}$ sensor assay. In some embodiments, the $5HT_{2A}$ sensor assay is in an agonist mode or an antagonist mode. In some embodiments, the $5HT_{2A}$ sensor assay is in an agonist mode. In some embodiments, a compound of the present invention that does not activate the sensor in agonist mode has non-hallucinogenic potential. In some embodiments, a compound of the present invention that does not activate the sensor in agonist mode is a non-hallucinogenic compound.

Figure 17A:
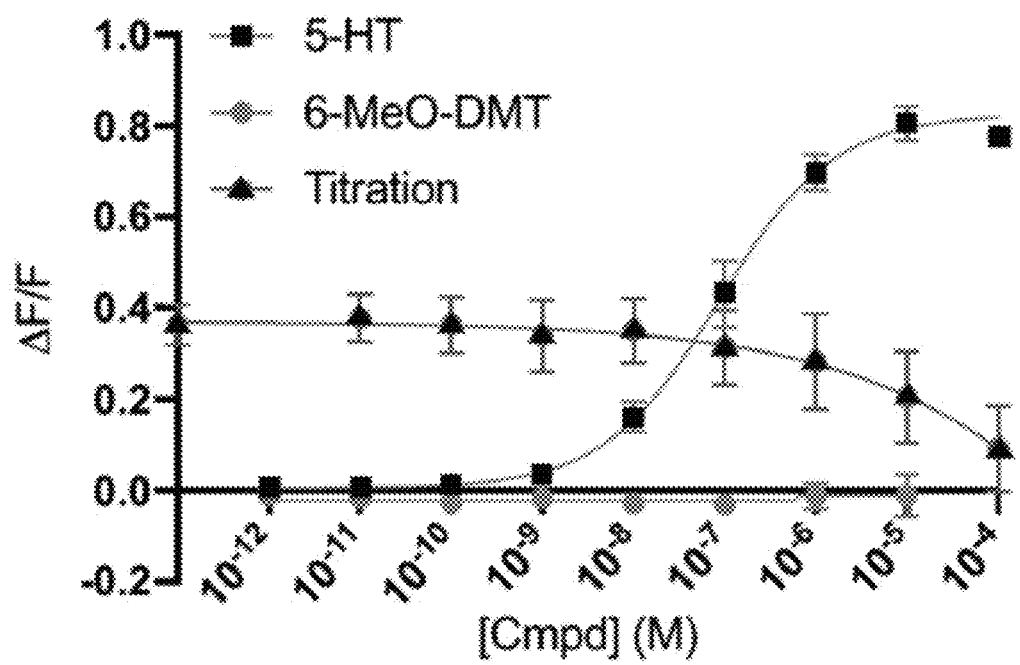
FIG. 17 shows the dose response profile of 5HT, 6-MeO-DMT (FIG. 17A), and lisuride (FIG. 17B) to a $5HT_{2A}$ sensor assay in antagonist mode.
Figure 17B:
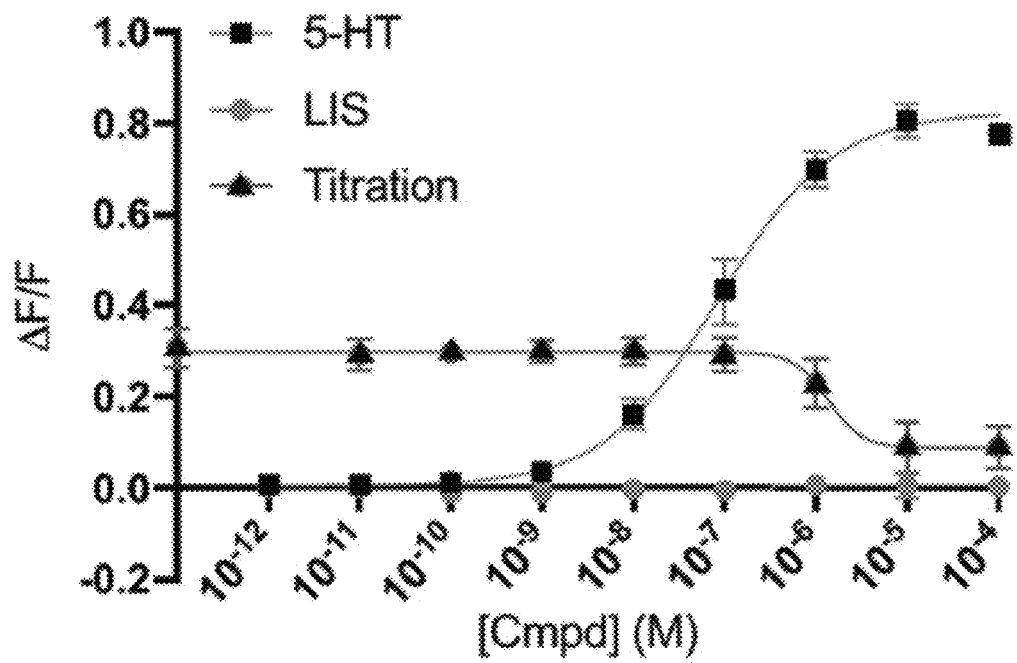
Figure 18:
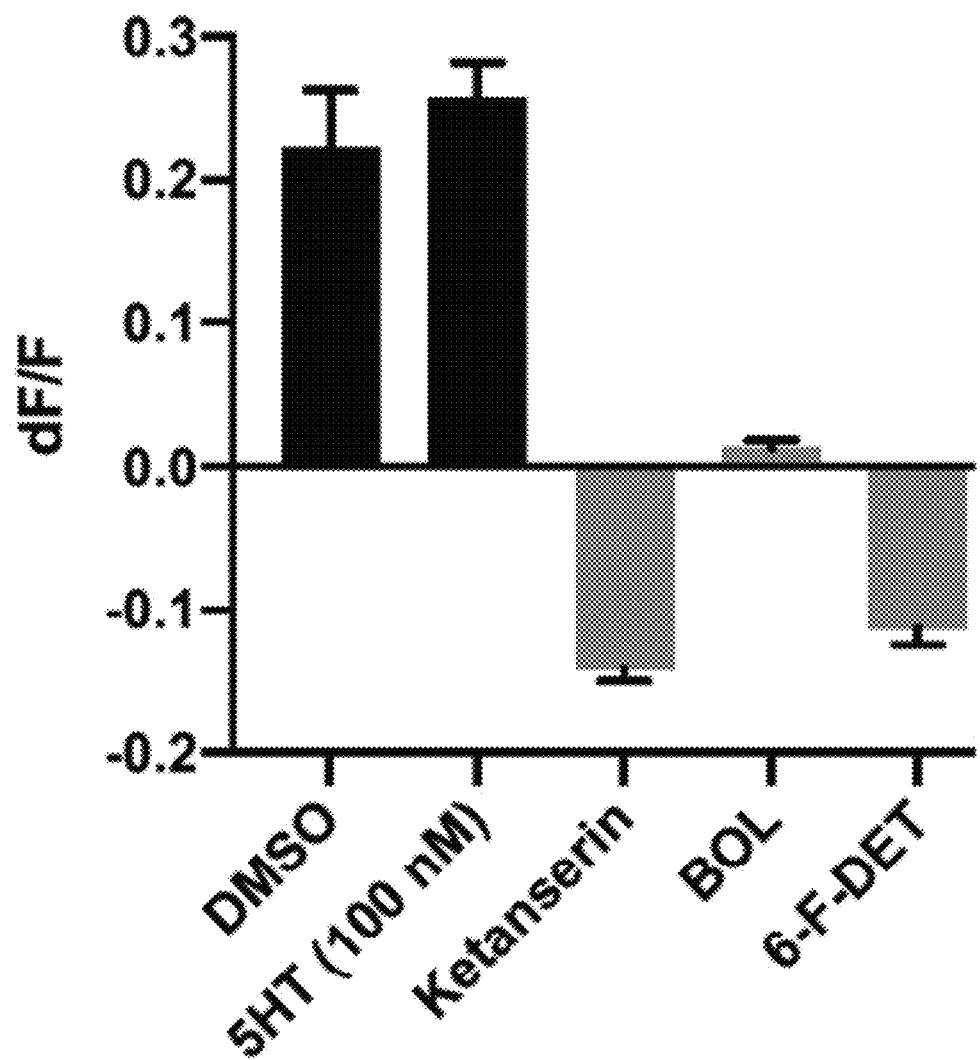
FIG. 18 shows the response profile of hallucinogenic and non-hallucinogenic compounds to a $5HT_{2A}$ sensor assay in antagonist mode.

Furthermore, non-hallucinogenic compounds (e.g., lisuride and 6-MeO-DMT) compete off 5-HT when the $5HT_{2A}$ sensor assay is run in antagonist mode (FIG. 17A and FIG. 17B). Additionally, compounds, such as, for example, 6-F-DET, Ketanserin, BOL148, which are non-hallucinogenic in animals (e.g., humans), compete with 5HT binding to $5HT_{2A}$ in the antagonist mode sensor assay (FIG. 18, at 10 µM of compound). In some embodiments, a compound of the present invention that prevents binding of 5-HT to $5HT_{2A}$. In some embodiments, the $5HT_{2A}$ sensor assay is in an antagonist mode. In some embodiments, a compound of the present invention that prevents binding of 5-HT to $5HT_{2A}$ and has non-hallucinogenic potential. In some embodiments, a compound of the present invention that prevents binding of 5-HT to $5HT_{2A}$ and is non-hallucinogenic. In some embodiments, a compound of the present invention that prevents binding of 5-HT to $5HT_{2A}$ in antagonist mode has non-hallucinogenic potential. In some embodiments, a compound of the present invention that prevents binding of 5-HT in antagonist mode is a non-hallucinogenic compound. In some embodiments, a compound of the present invention that inhibits the response of the sensor assay in antagonist mode has non-hallucinogenic potential. In some embodiments, a compound of the present invention that inhibits the response of the sensor assay in antagonist mode is a non-hallucinogenic compound.

In some embodiments, the results for the agonist mode sensor assay suggests a compound of the present invention is a non-hallucinogenic ligand of the $5\text{-HT}_{2A}$ receptor. In some embodiments, the results for the antagonist mode sensor assay suggests a compound of the present invention is a non-hallucinogenic ligand of the $5\text{-HT}_{2A}$ receptor. In some embodiments, the results for the agonist mode and antagonist mode sensor assay together suggest a compound of the present invention is a non-hallucinogenic ligand of the $5\text{-HT}_{2A}$ receptor.

In some embodiments, the compounds described herein are selective $5\text{-HT}_{2A}$ modulators. In some embodiments, the compounds described herein are $5\text{-HT}_{2A}$ modulators and promote neural plasticity (e.g., cortical structural plasticity). In some embodiments, the compounds described herein are selective $5\text{-HT}_{2A}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, the $5\text{-HT}_{2A}$ modulators (e.g., $5\text{-HT}_{2A}$ agonists) are non-hallucinogenic. In some embodiments, non-hallucinogenic $5\text{-HT}_{2A}$ modulators (e.g., $5\text{-HT}_{2A}$ agonists) are used to treat neurological diseases, which modulators do not elicit dissociative side-effects. In some embodiments, the hallucinogenic potential of the compounds described herein is assessed in vitro. In some embodiments, the hallucinogenic potential assessed in vitro of the compounds described herein is compared to the hallucinogenic potential assessed in vitro of hallucinogenic homologs. In some embodiments, the compounds described herein elicit less hallucinogenic potential in vitro than the hallucinogenic homologs.

In some embodiments, non-hallucinogenic $5\text{-HT}_{2A}$ modulators (e.g., $5\text{-HT}_{2A}$ agonists) are used to treat neurological diseases. In some embodiments, the neurological diseases comprise decreased neural plasticity, decreased cortical structural plasticity, decreased $5\text{-HT}_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, non-hallucinogenic $5\text{-HT}_{2A}$ modulators (e.g., $5\text{-HT}_{2A}$ agonists) are used for increasing neuronal plasticity. In some embodiments, non-hallucinogenic $5\text{-HT}_{2A}$ modulators (e.g., $5\text{-HT}_{2A}$ agonists) are used for treating a brain disorder. In some embodiments, non-hallucinogenic $5\text{-HT}_{2A}$ modulators (e.g., $5\text{-HT}_{2A}$ agonists) are used for increasing at least one of translation, transcription, or secretion of neurotrophic factors.

A. Methods for Increasing Neuronal Plasticity

Neuronal plasticity refers to the ability of the brain to change structure and/or function throughout a subject's life. New neurons can be produced and integrated into the central nervous system throughout the subject's life. Increasing neuronal plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neuronal plasticity comprises promoting neuronal growth, promoting neuritogenesis, promoting synaptogenesis, promoting dendritogenesis, increasing dendritic arbor complexity, and increasing dendritic spine density.

In some embodiments, increasing neuronal plasticity can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the present invention provides methods for increasing neuronal plasticity, comprising contacting a neuronal cell with any of the compounds of the present invention. In some embodiments, increasing neuronal plasticity improves a brain disorder described herein.

In some embodiments, a compound of the present invention is used to increase neuronal plasticity. In some embodiments, the compounds used to increase neuronal plasticity have, for example, anti-addictive properties, antidepressant properties, anxiolytic properties, or a combination thereof. In some embodiments, decreased neuronal plasticity is associated with a neuropsychiatric disease. In some embodiments, the neuropsychiatric disease is a mood or anxiety disorder. In some embodiments, the neuropsychiatric disease includes, for example, migraine, cluster headache, post-traumatic stress disorder (PTSD), schizophrenia, anxiety, depression, and addiction (e.g., substance abuse disorder). In some embodiments, brain disorders include, for example, migraines, addiction (e.g., substance use disorder), depression, and anxiety.

In some embodiments, the experiment or assay to determine increased neuronal plasticity of any compound of the present invention is a phenotypic assay, a dendritogenesis assay, a spinogenesis assay, a synaptogenesis assay, a Sholl analysis, a concentration-response experiment, a 5-$HT_{2A}$ agonist assay, a 5-$HT_{2A}$ antagonist assay, a 5-$HT_{2A}$ binding assay, or a 5-$HT_{2A}$ blocking experiment (e.g., ketanserin blocking experiments). In some embodiments, the experiment or assay to determine the hallucinogenic potential of any compound of Formula I or Formula (Ia) is a mouse head-twitch response (HTR) assay.

In some embodiments, the present invention provides a method for increasing neuronal plasticity, comprising contacting a neuronal cell with a compound of Formula I:

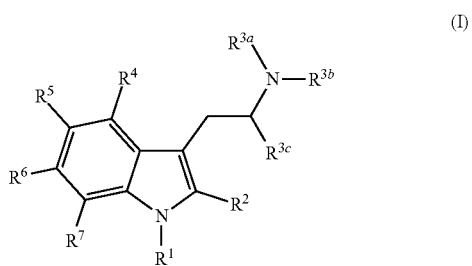

or a pharmaceutically acceptable salt thereof, in an amount sufficient to increase neuronal plasticity of the neuronal cell, wherein: $R^1$ is hydrogen or $C_{1-6}$ alkyl; $R^{3a}$ and $R^{3b}$ are each independently hydrogen, $C_{1-6}$ alkyl, $C_{3-8}$ cycloalkyl, or $C_{4-14}$ alkyl-cycloalkyl; $R^{3c}$ is hydrogen or $C_{1-6}$ alkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O; alternatively, $R^2$ and $R^{3c}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O; $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —C(O)$R^{8b}$, —C(O)O$R^{8b}$, —OC(O)$R^{8b}$, —OC(O)O$R^{8b}$, —N($R^{8b}R^{8c}$), —N($R^{8b}$)C(O)$R^{8c}$, —C(O)N($R^{8b}R^{8c}$), —N($R^{8b}$)C(O)O$R^{8c}$, —OC(O)N($R^{8b}R^{8c}$), —N($R^{8b}$)C(O)N($R^{8c}R^{8d}$), —C(O)C(O)N($R^{8b}R^{8c}$), —S($O_2$)$R^{8b}$, —S(O)$_2$N($R^{8b}R^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl or $C_{5-10}$ heteroaryl; and $R^{8a}$, $R^{8b}$, $R^{8c}$ and $R^{8d}$ are each independently H, $C_{1-6}$ alkyl.

In some embodiments, the present invention provides a method for increasing neuronal plasticity, comprising contacting a neuronal cell with a compound of Formula I, wherein: $R^1$ is hydrogen or $C_{1-6}$ alkyl; $R^{3a}$ and $R^{3b}$ are each independently hydrogen, $C_{1-6}$ alkyl, $C_{3-8}$ cycloalkyl, or $C_{4-14}$ alkyl-cycloalkyl; $R^{3c}$ is hydrogen or $C_{1-6}$ alkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O; alternatively, $R^2$ and $R^{3b}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O; $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —C(O)$R^{8b}$, —C(O)O$R^{8b}$, —OC(O)$R^{8b}$, —OC(O)O$R^{8b}$, —N($R^{8b}R^{8c}$), —N($R^{8b}$)C(O)$R^{8c}$, —C(O)N($R^{8b}R^{8c}$), —N($R^{8b}$)C(O)O$R^{8c}$, —OC(O)N($R^{8b}R^{8c}$), —N($R^{8b}$)C(O)N($R^{8c}R^{8d}$), —C(O)C(O)N($R^{8b}R^{8c}$), —S($O_2$)$R^{8b}$, —S(O)$_2$N($R^{8b}R^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H; $R^{8b}$, $R^{8c}$ and $R^{8d}$ are each independently H or $C_{1-6}$ alkyl; or pharmaceutically acceptable salts and isomers thereof, in an amount sufficient to increase neuronal plasticity of the neuronal cell.

B. Methods of Treating a Brain Disorder

In some embodiments, the present invention provides a method of treating a disease, including administering to a subject in need thereof, a therapeutically effective amount of a compound of the present invention. In some embodiments, the present invention provides a method of treating a brain disorder, including administering to a subject in need thereof, a therapeutically effective amount of a compound of the present invention. In some embodiments, the present invention provides a method of treating a brain disorder with combination therapy, including administering to a subject in need thereof, a therapeutically effective amount of a compound of the present invention and at least one additional therapeutic agent.

In some embodiments, 5-$HT_{2A}$ modulators (e.g., 5-$HT_{2A}$ agonists) are used to treat a brain disorder. In some embodiments, the brain disorders comprise decreased neural plasticity, decreased cortical structural plasticity, decreased 5-$HT_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, a compound of the present invention is used to treat brain disorders. In some embodiments, the compounds have, for example, anti-addictive properties, antidepressant properties, anxiolytic properties, or a combination thereof. In some embodiments, the brain disorder is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, schizophrenia, and addiction (e.g., substance abuse disorder). In some embodiments, brain disorders include, for example, migraines, addiction (e.g., substance use disorder), depression, and anxiety.

In some embodiments, the present invention provides a method of treating a brain disorder, comprising administering to a subject in need thereof a therapeutically effective amount of a compound of Formula I:

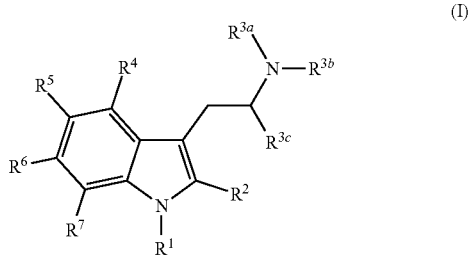

(I)

or a pharmaceutically acceptable salt thereof, thereby treating the brain disorder, wherein: $R^1$ is hydrogen or $C_{1-6}$ alkyl; $R^{3a}$ and $R^{3b}$ are each independently hydrogen, $C_{1-6}$ alkyl, $C_{3-8}$ cycloalkyl, or $C_{4-14}$ alkyl-cycloalkyl; $R^{3c}$ is hydrogen or $C_{1-6}$ alkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O; alternatively, $R^2$ and $R^{3c}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O; $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, $-OR^{8a}$, $-NO_2$, $-CN$, $-C(O)R^{8b}$, $-C(O)OR^{8b}$, $-OC(O)R^{8b}$, $-OC(O)OR^{8b}$, $-N(R^{8b}R^{8c})$, $-N(R^{8b})C(O)R^{8c}$, $-C(O)N(R^{8b}R^{8c})$, $-N(R^{8b})C(O)OR^{8c}$, $-OC(O)N(R^{8b}R^{8c})$, $-N(R^{8b})C(O)N(R^{8c}R^{8d})$, $-C(O)C(O)N(R^{8b}R^{8c})$, $-S(O)_2R^{8b}$, $-S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl or $C_{5-10}$ heteroaryl; and $R^{8a}$, $R^{8b}$, $R^{8c}$ and $R^{8d}$ are each independently H, $C_{1-6}$ alkyl.

In some embodiments, the present invention provides a method of treating a brain disorder, comprising administering to a subject in need thereof a therapeutically effective amount of a compound of Formula I, wherein: $R^1$ is hydrogen or $C_{1-6}$ alkyl; $R^{3a}$ and $R^{3b}$ are each independently hydrogen, $C_{1-6}$ alkyl, $C_{3-8}$ cycloalkyl, or $C_{4-14}$ alkyl-cycloalkyl; $R^{3c}$ is hydrogen or $C_{1-6}$ alkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O; alternatively, $R^2$ and $R^{3b}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O; $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, $-OR^{8a}$, $-NO_2$, $-CN$, $-C(O)R^{8b}$, $-C(O)OR^{8b}$, $-OC(O)R^{8b}$, $-OC(O)OR^{8b}$, $-N(R^{8b}R^{8c})$, $-N(R^{8b})C(O)R^{8c}$, $-C(O)N(R^{8b}R^{8c})$, $-N(R^{8b})C(O)OR^{8c}$, $-OC(O)N(R^{8b}R^{8c})$, $-N(R^{8b})C(O)N(R^{8c}R^{8d})$, $-C(O)C(O)N(R^{8b}R^{8c})$, $-S(O)_2R^{8b}$, $-S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H; $R^{8b}$, $R^{8c}$ and $R^{8d}$ are each independently H or $C_{1-6}$ alkyl; or pharmaceutically acceptable salts and isomers thereof, thereby treating the brain disorder In some embodiments, the brain disorder is a neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the brain disorder is a neurodegenerative disorder, Alzheimer's, or Parkinson's disease. In some embodiments, the brain disorder is a psychological disorder, depression, addiction, anxiety, or a post-traumatic stress disorder. In some embodiments, the brain disorder is depression. In some embodiments, the brain disorder is addiction. In some embodiments, the brain disorder is treatment resistant depression, suicidal ideation, major depressive disorder, bipolar disorder, schizophrenia, stroke, traumatic brain injury or substance use disorder. In some embodiments, the brain disorder is treatment resistant depression, suicidal ideation, major depressive disorder, bipolar disorder, schizophrenia, or substance use disorder. In some embodiments, the brain disorder is treatment resistant depression, suicidal ideation, major depressive disorder, bipolar disorder, or substance use disorder. In some embodiments, the brain disorder is stroke or traumatic brain injury. In some embodiments, the brain disorder is schizophrenia. In some embodiments, the brain disorder is alcohol use disorder.

In some embodiments, the method further comprises administering one or more additional therapeutic agent that is lithium, Olanzapine (Zyprexa), Quetiapine (Seroquel), Risperidone (Risperdal), Ariprazole (Abilify), Ziprasidone (Geodon), Clozapine (Clozaril), divalproex sodium (Depakote), lamotrigine (Lamictal), valproic acid (Depakene), carbamazepine (Equetro), topiramate (Topamax), levomilnacipran (Fetzima), duloxetine (Cymbalta, Yentreve), venlafaxine (Effexor), citalopram (Celexa), fluvoxamine (Luvox), escitalopram (Lexapro), fluoxetine (Prozac), paroxetine (Paxil), sertraline (Zoloft), clomipramine (Anafranil), amitriptyline (Elavil), desipramine (Norpramin), imipramine (Tofranil), nortriptyline (Pamelor), phenelzine (Nardil), tranylcypromine (Parnate), diazepam (Valium), alprazolam (Xanax), or clonazepam (Klonopin).

In some embodiments, the compounds of the present invention are used in combination with the standard of care therapy for a neurological disease described herein. Non-limiting examples of the standard of care therapies, may include, for example, lithium, olanzapine, quetiapine, risperidone, ariprazole, ziprasidone, clozapine, divalproex sodium, lamotrigine, valproic acid, carbamazepine, topiramate, levomilnacipran, duloxetine, venlafaxine, citalopram, fluvoxamine, escitalopram, fluoxetine, paroxetine, sertraline, clomipramine, amitriptyline, desipramine, imipramine, nortriptyline, phenelzine, tranylcypromine, diazepam, alprazolam, clonazepam, or any combination thereof. Non-limiting examples of standard of care therapy for depression are sertraline, fluoxetine, escitalopram, venlafaxine, or aripiprazole. Non-limiting examples of standard of care therapy for depression are citralopram, escitalopram, fluoxetine, paroxetine, diazepam, or sertraline.

C. Methods of Increasing at Least One of Translation, Transcription, or Secretion of Neurotrophic Factors Neurotrophic factors refers to a family of soluble peptides or proteins which support the survival, growth, and differentiation of developing and mature neurons. Increasing at least one of translation, transcription, or secretion of neurotrophic factors can be useful for, but not limited to, increasing neuronal plasticity, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing at least one of translation, transcription, or secretion of neurotrophic factors can increasing neuronal plasticity. In some embodiments, increasing at least one of translation, transcription, or secretion of neurotrophic factors can promoting neuronal growth, promoting neuritogenesis, promoting synaptogenesis, promoting dendritogenesis, increasing dendritic arbor complexity, and/or increasing dendritic spine density.

In some embodiments, 5-HT$_{2A}$ modulators (e.g., 5-HT$_{2A}$ agonists) are used to increase at least one of translation, transcription, or secretion of neurotrophic factors. In some embodiments, a compound of Formula I or Formula (Ia) described herein is used increase at least one of translation, transcription, or secretion of neurotrophic factors. In some embodiments, increasing at least one of translation, transcription or secretion of neurotrophic factors treats a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder).

In some embodiments, the experiment or assay used to determine increase translation of neurotrophic factors includes ELISA, western blot, immunofluorescence assays, proteomic experiments, and mass spectrometry. In some embodiments, the experiment or assay used to determine increase transcription of neurotrophic factors includes gene expression assays, PCR, and microarrays. In some embodiments, the experiment or assay used to determine increase secretion of neurotrophic factors includes ELISA, western blot, immunofluorescence assays, proteomic experiments, and mass spectrometry.

In some embodiments, the present invention provides a method for increasing at least one of translation, transcription or secretion of neurotrophic factors, comprising contacting a neuronal cell with a compound of Formula I:

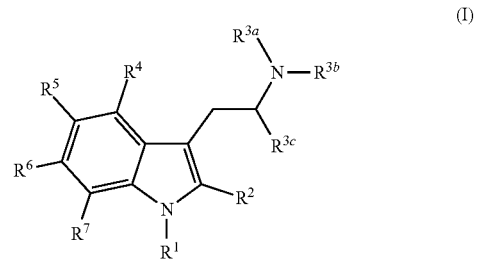

or a pharmaceutically acceptable salt thereof, in an amount sufficient to increase neuronal plasticity of the neuronal cell, wherein: $R^1$ is hydrogen or $C_{1-6}$ alkyl; $R^{3a}$ and $R^{3b}$ are each independently hydrogen, $C_{1-6}$ alkyl, $C_{3-8}$ cycloalkyl, or $C_{4-14}$ alkyl-cycloalkyl; $R^{3c}$ is hydrogen or $C_{1-6}$ alkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form =O; alternatively, $R^2$ and $R^{3c}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form =O; $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —OR$^{8a}$, —NO$_2$, —CN, —C(O)R$^{8b}$, —C(O)OR$^{8b}$, —OC(O)R$^{8b}$, —OC(O)OR$^{8b}$, —N(R$^{8b}$R$^{8c}$), —N(R$^{8b}$)C(O)R$^{8c}$, —C(O)N(R$^{8b}$R$^{8c}$), —N(R$^{8b}$)C(O)OR$^{8c}$, —OC(O)N(R$^{8b}$R$^{8c}$), —N(R$^{8b}$)C(O)N(R$^{8c}$R$^{8d}$), —C(O)C(O)N(R$^{8b}$R$^{8c}$), —S(O$_2$)R$^{8b}$, —S(O)$_2$N(R$^{8b}$R$^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl or $C_{5-10}$ heteroaryl; and $R^{8a}$, $R^{8b}$, $R^{8c}$ and $R^{8d}$ are each independently H, $C_{1-6}$ alkyl.

In some embodiments, the present invention provides a method for increasing at least one of translation, transcription or secretion of neurotrophic factors, comprising contacting a neuronal cell with a compound of Formula I, wherein: $R^1$ is hydrogen or $C_{1-6}$ alkyl; $R^{3a}$ and $R^{3b}$ are each independently hydrogen, $C_{1-6}$ alkyl, $C_{3-8}$ cycloalkyl, or $C_{4-14}$ alkyl-cycloalkyl; $R^{3c}$ is hydrogen or $C_{1-6}$ alkyl; alternatively, $R^2$ and $R^{3b}$ are combined with the atoms to which they are attached to form a $C_{5-8}$ heterocycloalkyl substituted with 1 to 3 $R^9$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^9$ groups attached to the same atom are combined to form=O; alternatively, $R^2$ and $R^{3b}$ are combined with the atoms to which they are attached to form a $C_{5-8}$ cycloalkyl, substituted with 1 to 3 $R^{10}$ groups which are each independently hydrogen, $C_{1-6}$ alkyl, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, or two $R^{10}$ groups attached to the same atom are combined to form=O; $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —OR$^{8a}$, —NO$_2$, —CN, —C(O)R$^{8b}$, —C(O)OR$^{8b}$, —OC(O)R$^{8b}$, —OC(O)OR$^{8b}$, —N(R$^{8b}$R$^{8c}$), —N(R$^{8b}$)C(O)R$^{8c}$, —C(O)N(R$^{8b}$R$^{8c}$), —N(R$^{8b}$)C(O)OR$^{8c}$, —OC(O)N(R$^{8b}$R$^{8c}$), —N(R$^{8b}$)C(O)N(R$^{8c}$R$^{8d}$), —C(O)C(O)N(R$^{8b}$R$^{8c}$), —S(O$_2$)R$^{8b}$, —S(O)$_2$N(R$^{8b}$R$^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl, wherein at least one of $R^4$, $R^5$, $R^6$ and $R^7$ is not H; $R^{8b}$, $R^{8c}$ and $R^{8d}$ are each independently H or $C_{1-6}$ alkyl; or pharmaceutically acceptable salts and isomers thereof, in an amount sufficient to increase neuronal plasticity of the neuronal cell.

VII. Examples

Chemistry (General). All reagents were obtained commercially unless otherwise noted. Reactions were performed using glassware that was oven dried (120° C.) unless otherwise stated. Air- and moisture-sensitive liquids and solutions were transferred via syringe or stainless-steel cannula. Organic solutions were concentrated under reduced pressure (~5 Torr) by rotary evaporation. Solvents were purified by passage under 12 psi $N_2$ through activated alumina columns. Chromatography was performed using Fisher Chemical™ Silica Gel Sorbent (230-400 Mesh, Grade 60). Compounds purified by chromatography were typically applied to the adsorbent bed using the indicated solvent conditions with a minimum amount of added dichloromethane as needed for solubility. Thin layer chromatography (TLC) was performed on Merck silica gel 60 F254 plates (250 µm). Visualization of the developed chromatogram was accomplished by fluorescence quenching or by staining with butanolic ninhydrin, aqueous potassium permanganate, ethanolic vanillin, or aqueous ceric ammonium molybdate (CAM).

Nuclear magnetic resonance (NMR) spectra were acquired on either a Bruker 400 operating at 400 and 100 MHz or a Varian-600 operating at 600 and 150 MHz for $^1$H and $^{13}$C, respectively, and are referenced internally according to residual solvent signals. Data for 1H NMR are recorded as follows: chemical shift (δ, ppm), multiplicity (s, singlet; br s, broad singlet; d, doublet; t, triplet; q, quartet; quint, quintet; sext, sextet; m, multiplet), integration, and coupling constant (Hz). Data for $^{13}$C NMR are reported in terms of chemical shift (δ, ppm). Infrared spectra were recorded using a Thermo Scientific Nicolet iS10 spectrometer with Smart iTX Accessory (diamond ATR) and are reported in frequency of absorption. Low-resolution mass spectra were obtained using a Waters Acuity Arc LC-MS.

The specific procedures used to synthesize the compounds reported in this manuscript are detailed below along with characterization data. Spectral data (41 and $^{13}$C NMR spectra) for each compound tested in biological assays is included.

Example 1. Synthesis and Biological Activity of Ibogalogs

The pharmacophore of ibogaine is depicted in FIG. 1A. A series of tetrahydroazepine-containing compounds that lacked the isoquinuclidine characteristic of ibogaine (FIG. 1B) was synthesized.

Embryonic rat cortical neurons were treated for a short period of time (1 h) followed by a suitable growth period (71 h) to measure the psychoplastogenic effects of the compounds described herein. Using this short treatment protocol (Dunlap, et al. Identification of Psychoplastogenic N,N-Dimethylaminoisotryptamine (isoDMT) Analogs Through Structure-Activity Relationship Studies. *J. Med. Chem.*, 2019), ibogaine demonstrates psychoplastogenic effects as measured via Sholl analysis. Therefore, the effects of ibogalogs 8-17 on dendritic growth was assessed.

Figure 5A:
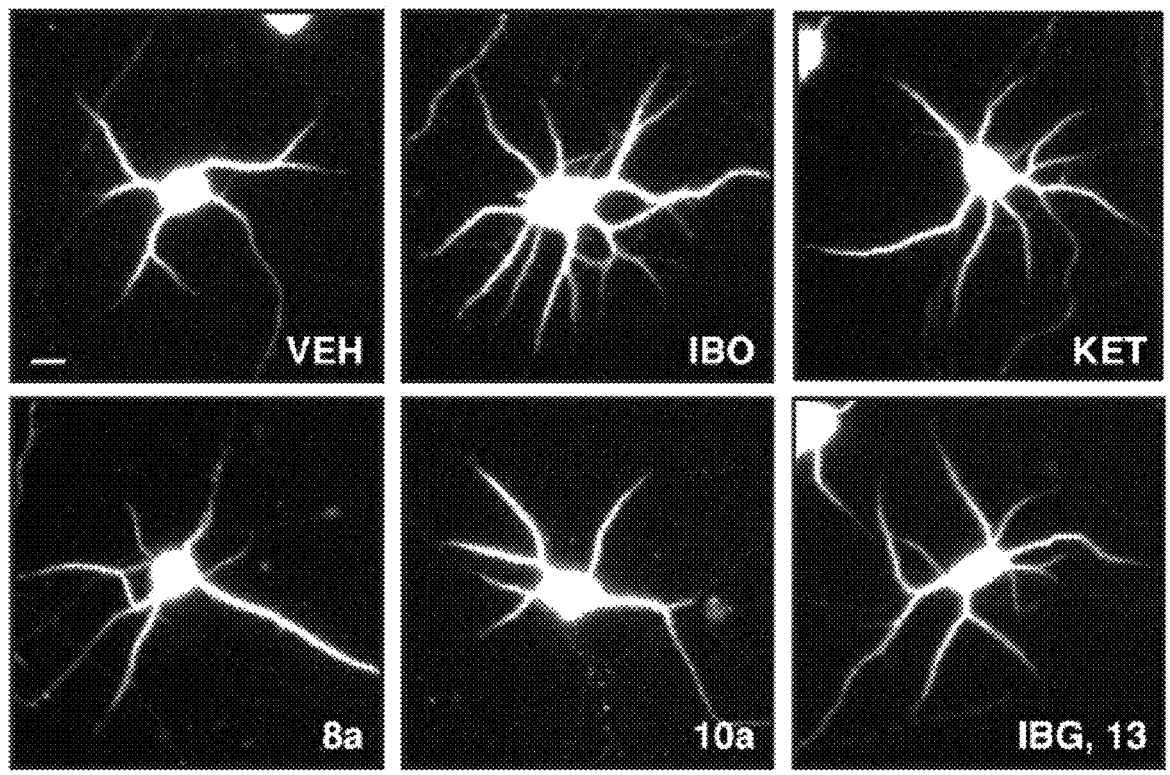
FIG. 5A to FIG. 5B show the effects of ibogalogs on dendritogenesis.
Figure 5B:
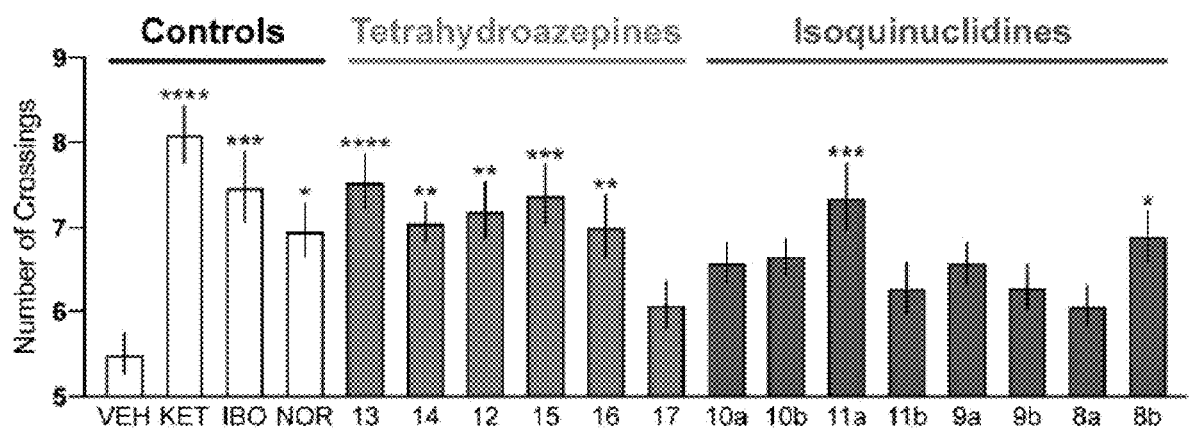
Figure 6:
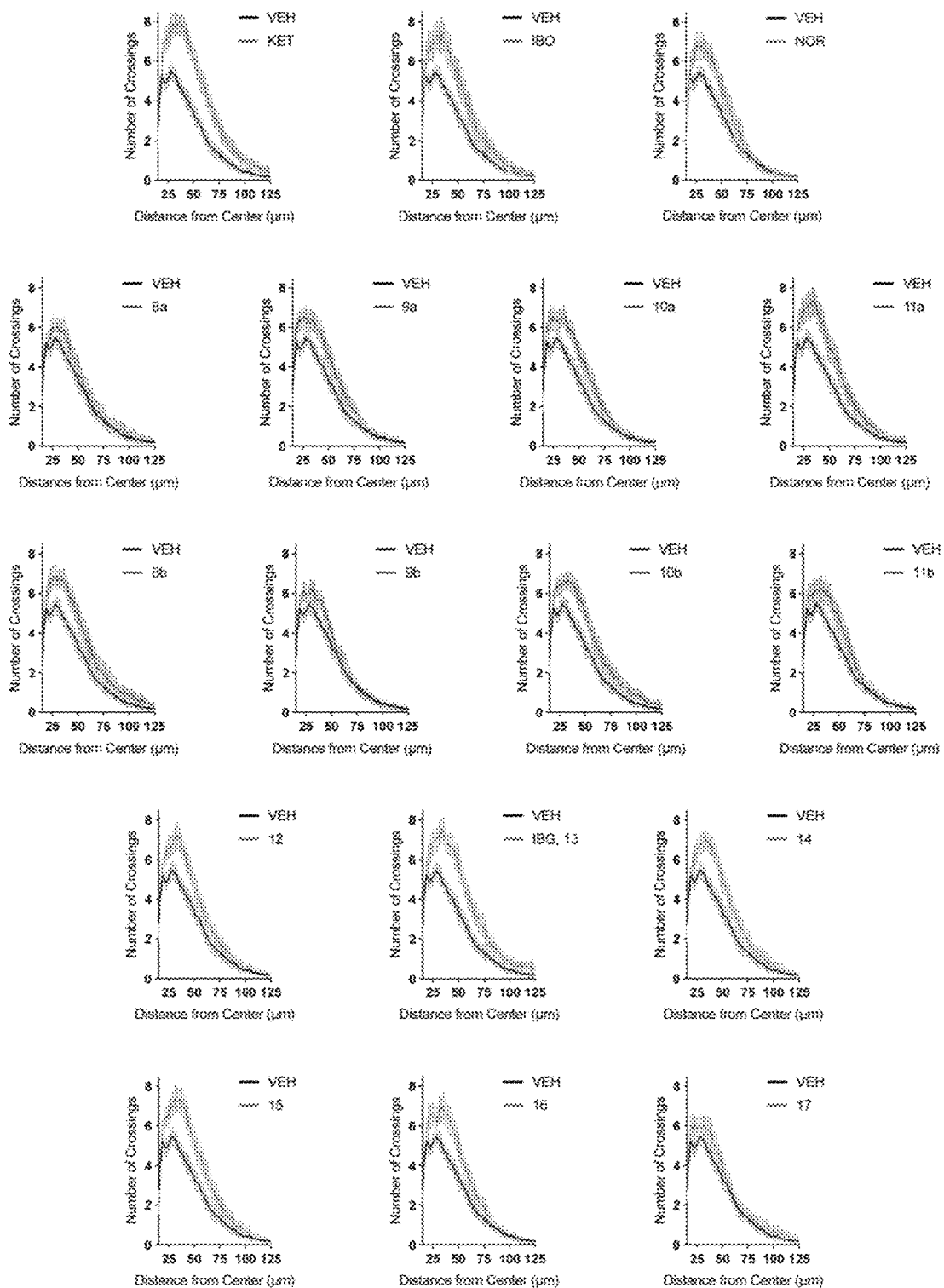
FIG. 6 shows several ibogalogs promote dendritogenesis. Sholl analysis (circle radii=1.34 µm increments) demonstrates that cultured cortical neurons treated with several ibogalogs have more complex dendritic arbors as compared to vehicle control (n=52-83 neurons per treatment). The shaded area surrounding each line represents 95% confidence intervals. Control compounds, isoquinuclidines, and tetrahydroazepines are shown in blue, purple, and red, respectively.

Except for 11a, ibogalogs containing the isoquinuclidine but lacking the tetrahydroazepine ring (8-10 and 11b) were weak psychoplastogens or did not promote neuronal growth compared to the vehicle (VEH) control (FIG. 5 and FIG. 6). Ibogalogs lacking the isoquinuclidine but retaining the tetrahydroazepine (13-16) were efficacious (FIG. 5 and FIG. 6). Indole substitution at C5 with fluorine or chlorine was tolerated, but a more sterically demanding bromine substituent was not. IBG (13) performed comparably to ibogaine despite having a drastically simplified chemical structure.

Figure 2D:
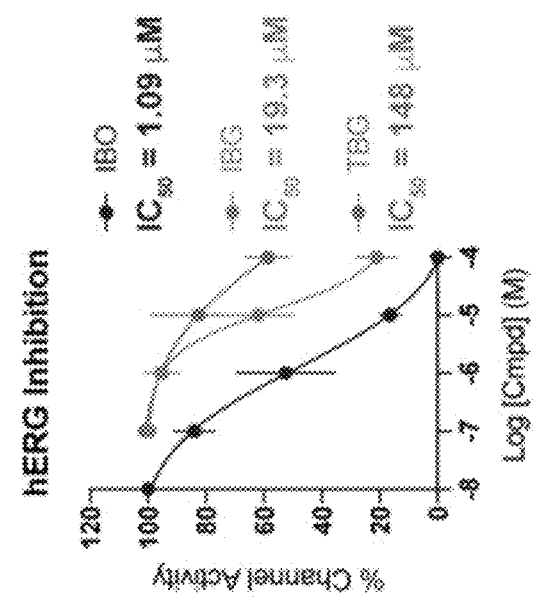
Figure 2C:
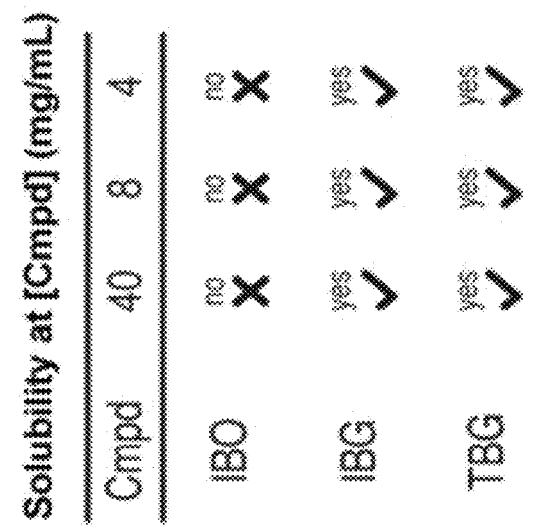
Figure 2B:
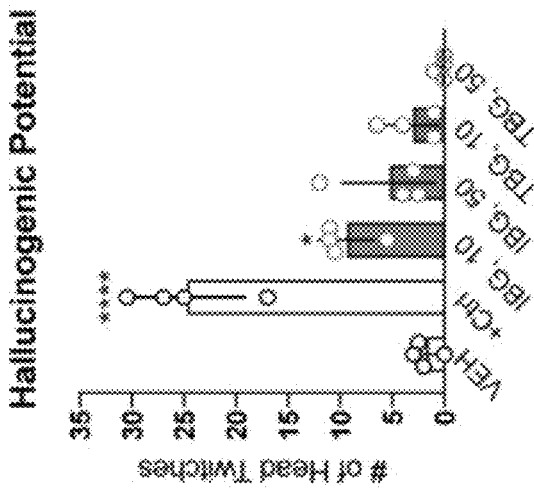

A HTR assay using 5-MeO-DMT (10 mg/kg) as a positive control (FIG. 2B) was used to evaluate the hallucinogenic potential of IBG and tabernanthalog (TBG). While 5-MeO-DMT produces a robust HTR, its conformationally restricted analog IBG exhibits significantly reduced hallucinogenic potential. The 6-methoxy substituent of TBG did not display hallucinogenic potential as measured by the HTR assay. For these in vivo studies, the fumarate salts of IBG and TBG were utilized. Unlike ibogaine hydrochloride, they are readily soluble in 0.9% saline up to 40 mg/mL (FIG. 2C). Ibogaine's lack of water solubility (FIG. 7) is a potential issue not only for clinical formulation, but also for administration to animals during preclinical testing.

Figures 2E, 2F:
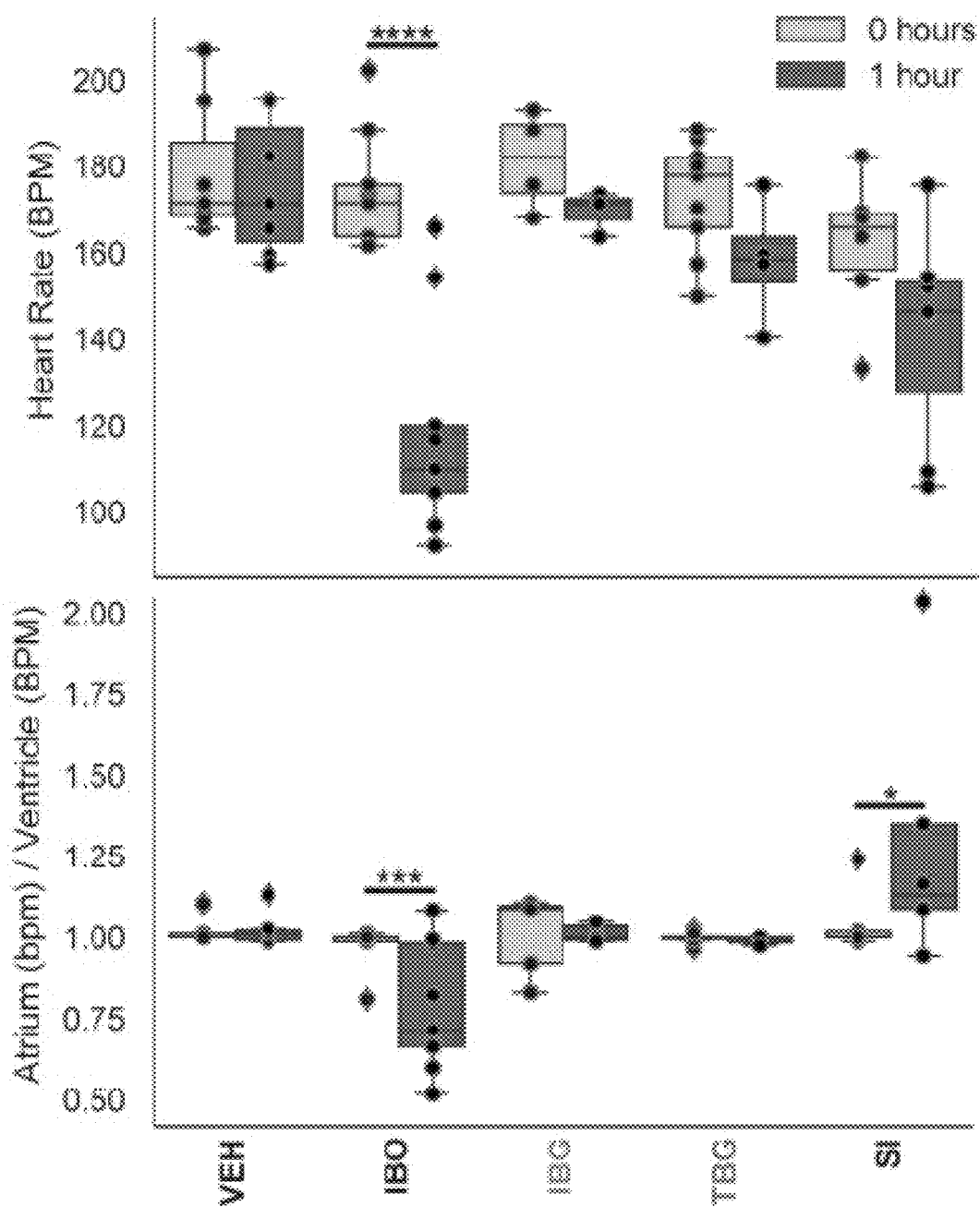

The lipophilicity of ibogaine not only poses practical issues for its administration, it is likely a major factor contributing to its toxicity and adverse cardiac effects. Ibogaine inhibits hERG channels with an $IC_{50}$ of approximately 1 µM (FIG. 2D). In contrast, IBG and TBG are approximately 10- and 100-fold less potent than ibogaine, respectively (IBG $IC_{50}$=19.3 µM; TBG $IC_{50}$=148 µM), indicating a lower potential for cardiotoxicity. Administration of ibogaine to immobilized larval zebrafish resulted in a visually noticeable decrease in heart rate (FIG. 2E) and an increased likelihood for inducing arrhythmias as measured by the ratio of atrium to ventricle beats per minute (BPM) (FIG. 2F). Neither IBG nor TBG induced these undesirable phenotypes.

Figure 8:
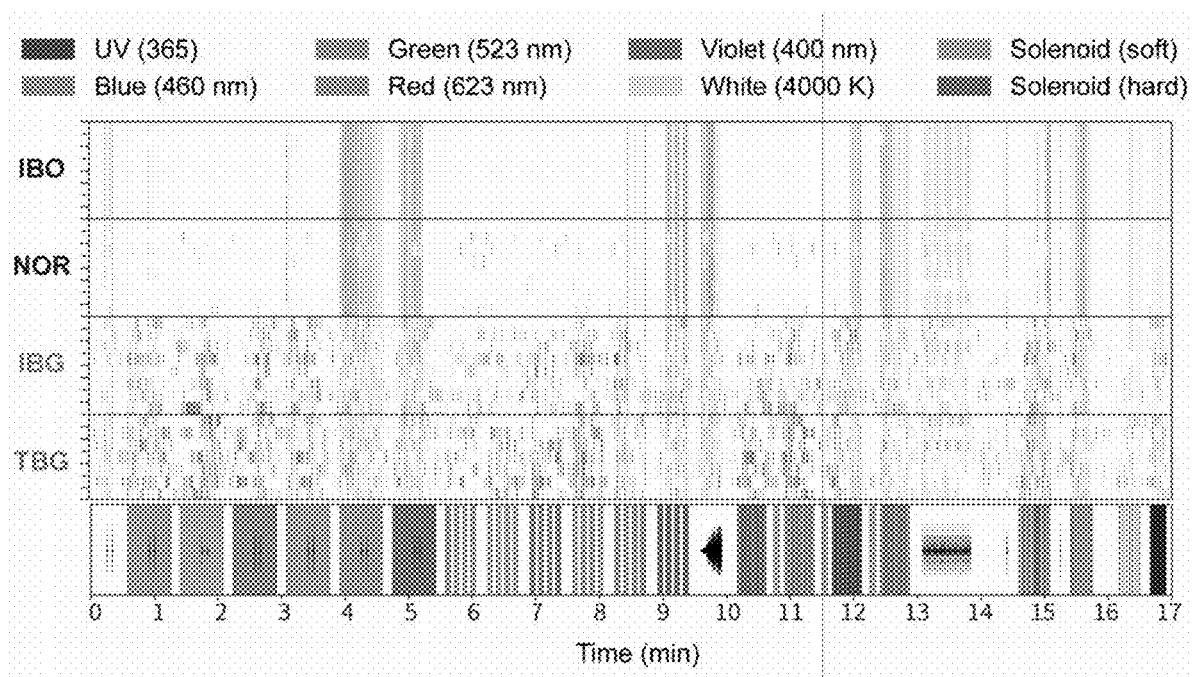
FIG. 8 shows heatmaps representing aggregate larval zebrafish locomotor activity per well compared to vehicle controls (pseudo-Z-score). Red and blue indicate higher and lower activity than the mean of vehicle controls, respectively, while white indicates activity within ±1 SD from control. Stimuli applied over time are indicated under the heatmaps. Colors indicate bright LED light of respective colors, black traces represent the waveforms of acoustic stimuli, and gray vertical lines indicate physical tapping as secondary acoustic stimuli.
Figure 9:
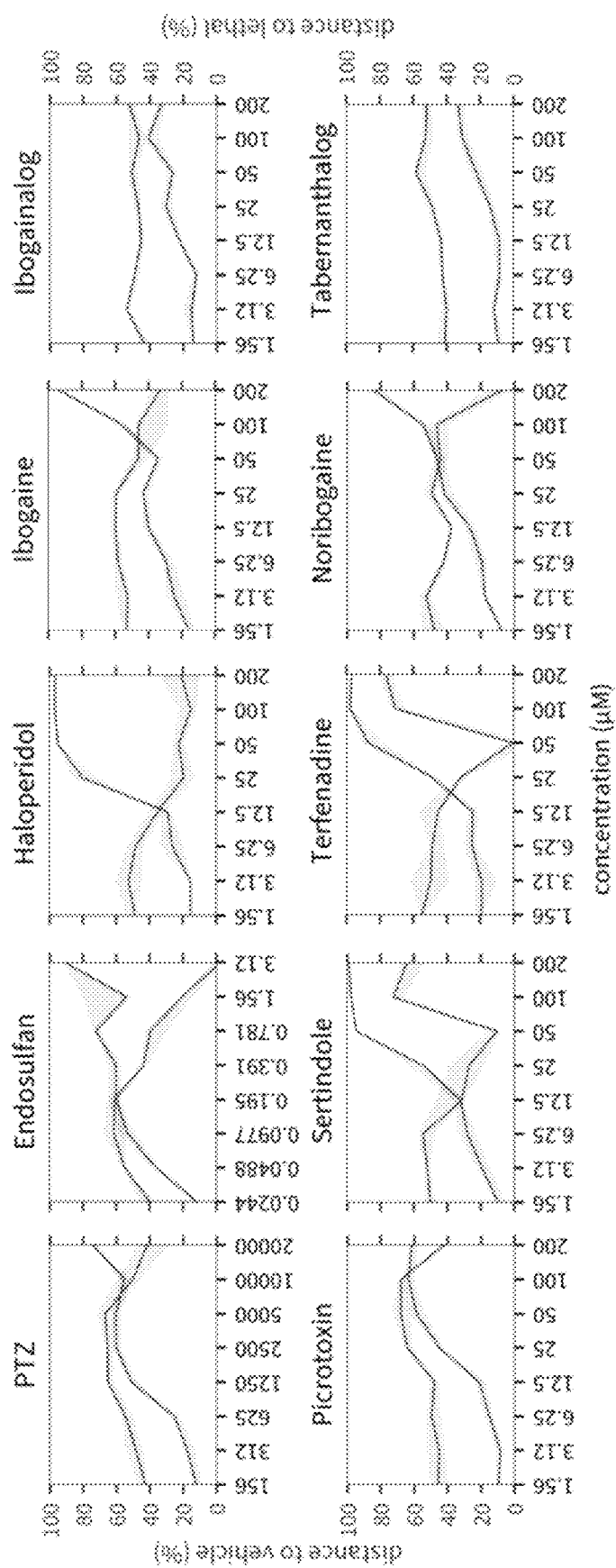
FIG. 9 shows increasing concentrations of MG and TBG do not produce movement responses in larval zebrafish similar to a lethal concentration of eugenol (100 µM). Concentration-response curves for compounds subjected to the battery of stimuli shown in FIG. 8. Response is inversely proportional to classification accuracy; 0-20% indicates no ability and 100% indicates perfect classification. Lower percentages indicate treatments that were more often classified as vehicle (blue) or lethal (red). The solid line denotes the median and the shading denotes a 95th percentile confidence interval calculated by bootstrap. N=8 wells/condition (64 animals/condition).

To compare the acute behavioral effects of ibogaine, IBG, and TBG, larval zebrafish for 1 h were treated and then quantified their movement activity during a battery of light and acoustic stimuli as described previously (FIG. 8). With increasing concentration, ibogaine, noribogaine, and the hERG inhibitors haloperidol, sertindole, and terfenadine become more phenotypically distinct from the vehicle control, while more closely resembling the lethal control (eugenol, 100 µM) (FIG. 9). At the highest concentrations tested (200 µM), noribogaine and a toxic pesticide (endosulfan) were phenotypically consistent with the lethal control. In contrast, IBG and TBG did not produce this phenotype. A machine learning approach showed that, at the highest concentrations, IBG and TBG caused movement responses that were more similar to vehicle controls than to ibogaine, noribogaine, or lethal controls (FIG. 2G). This suggests that the novel compounds have superior acute safety profiles.

Figure 10:
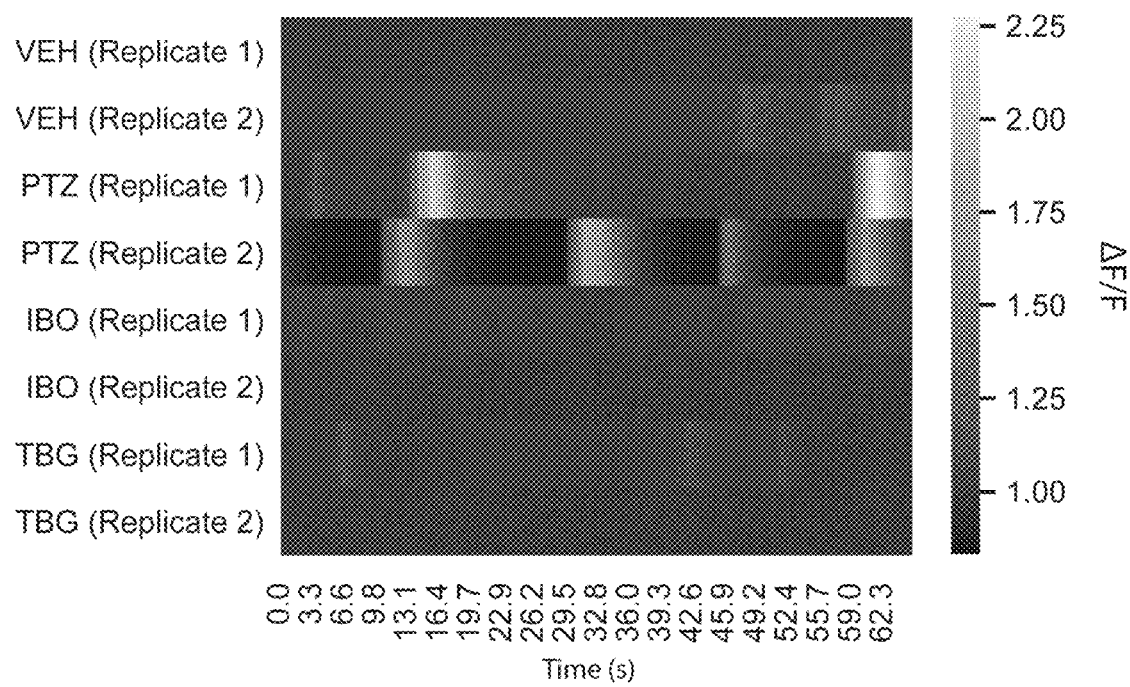
FIG. 10 shows TBG does not induce seizures in larval zebrafish. Transgenic larval zebrafish expressing GCaMP5G were immobilized in agarose, treated with compounds, and imaged over time. The known seizure-inducing compound PTZ was used as a positive control. All compounds were treated at 200 µM (n=2 per condition).

As ibogaine is known to cause seizures at very high doses, seizurogenic potential using larval zebrafish expressing GCaMP5 was assessed. Neither ibogaine nor TBG produced excessive neural activity as was observed following treatment with the known seizure-inducing compound pentylenetetrazole (PTZ) (FIG. 10).

Figure 11A:
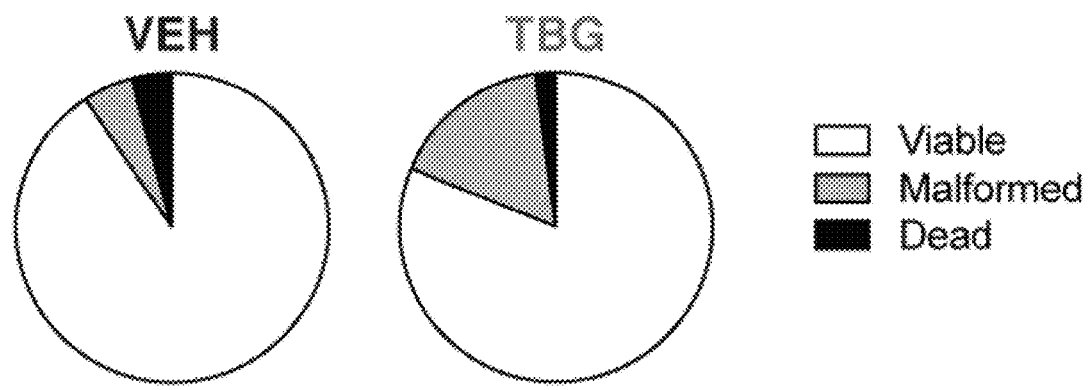
FIG. 11A and FIG. 11B show TBG (66 µM) does not cause developmental toxicity in zebrafish.
Figure 11B:
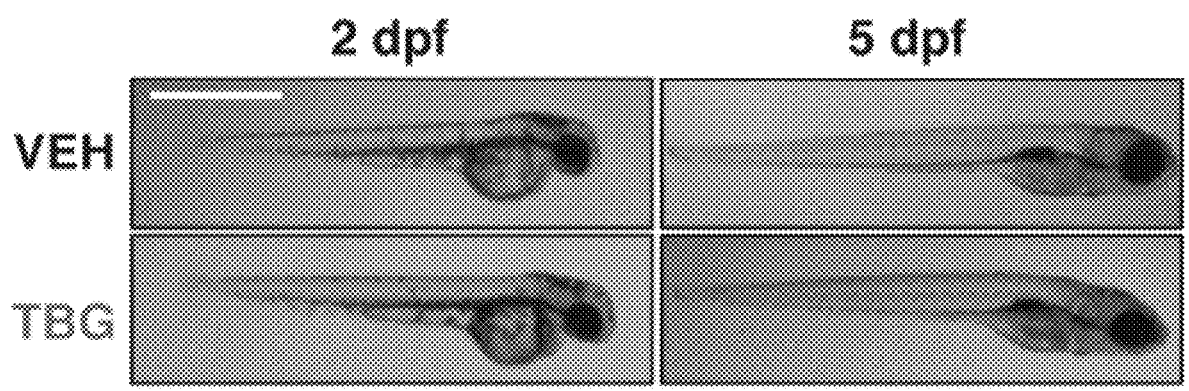

Finally, in a well-established zebrafish developmental toxicity assay, Ibogaine (100 µM) significantly increased malformations and mortality at 2 and 5 days post-fertilization (dpf), respectively (FIG. 2H and FIG. 2I). At both timepoints, the proportion of viable to non-viable fish was significantly different from vehicle control (Fisher's exact test, p<0.0001). Ibogaine-treated animals suffered from numerous malformations. Noribogaine treatment resulted in greater survival, but the majority of the animals exhibited yolk sac and/or pericardial edemas. In sharp contrast, both IBG and TBG treatments (100 µM) resulted in significantly fewer non-viable fish than ibogaine or noribogaine treatments at both 2 and 5 dpf (Fisher's exact test, p<0.0001 for ibogaine vs. IBG and ibogaine vs. TBG at both 2 and 5 dpf; p<0.0001 for noribogaine vs. IBG at both 2 and 5 dpf and noribogaine vs. TBG at 2 dpf; p=0.0083 for NOR vs. TBG at 5 dpf). Moreover, the effects of compound-induced malformations and/or death were both time- (FIG. 2J) and concentration-dependent (FIG. 11). Importantly, reducing the concentration of TBG from 100 to 66 µM resulted in a proportion of viable to non-viable fish that was statistically indistinguishable from vehicle control after 5 dpf (Fisher's exact test, p=0.3864).

Figure 12:
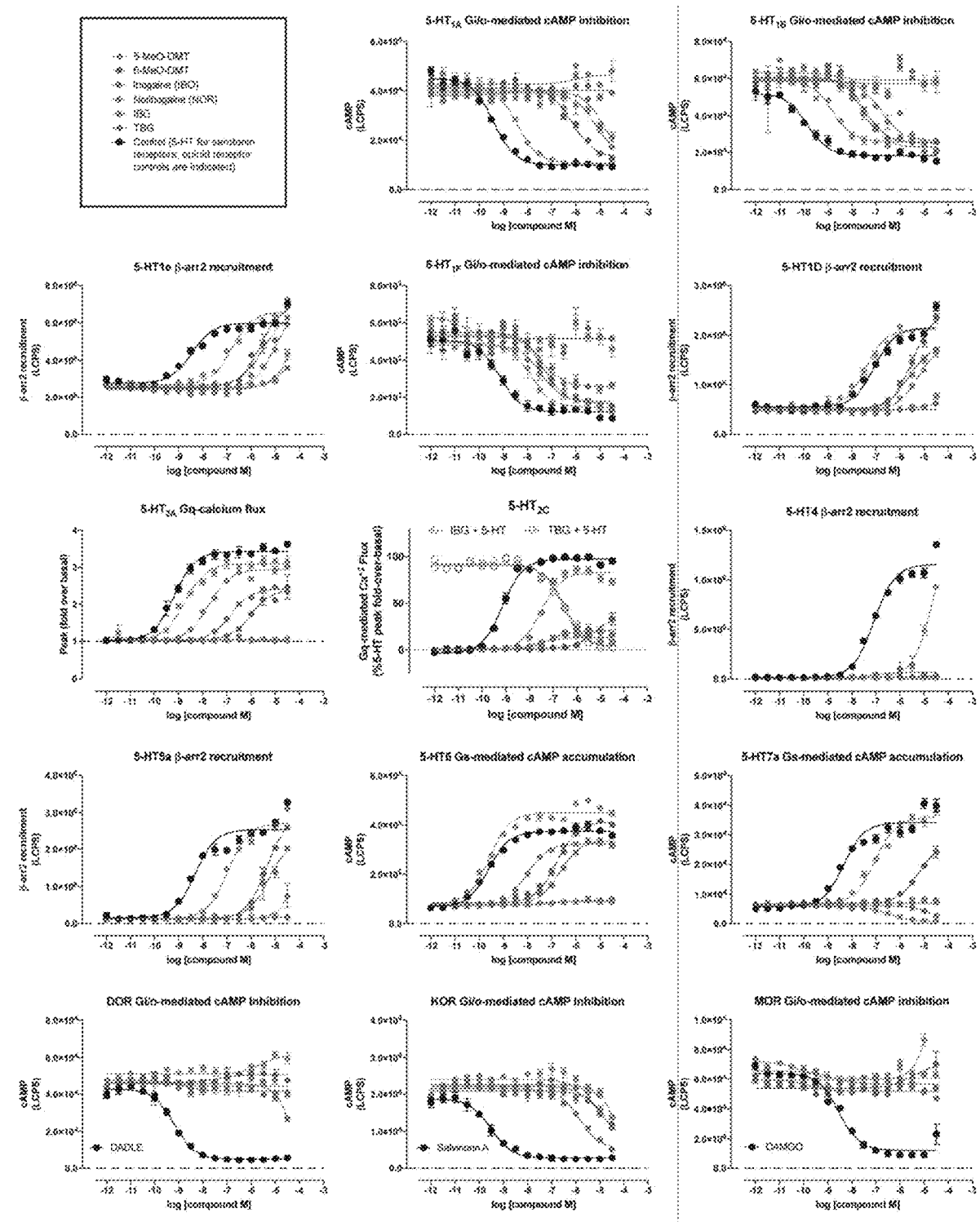
FIG. 12 shows concentration-response curves demonstrating the abilities of ibogalogs and related compounds to activate 5-HT and opioid receptors. All compounds were assayed in parallel using the same drug dilutions. Graphs reflect representative concentration-response curves plotting mean and S.E.M of data points performed in duplicate or triplicate. Assay details are described in the methods.
Figure 14:
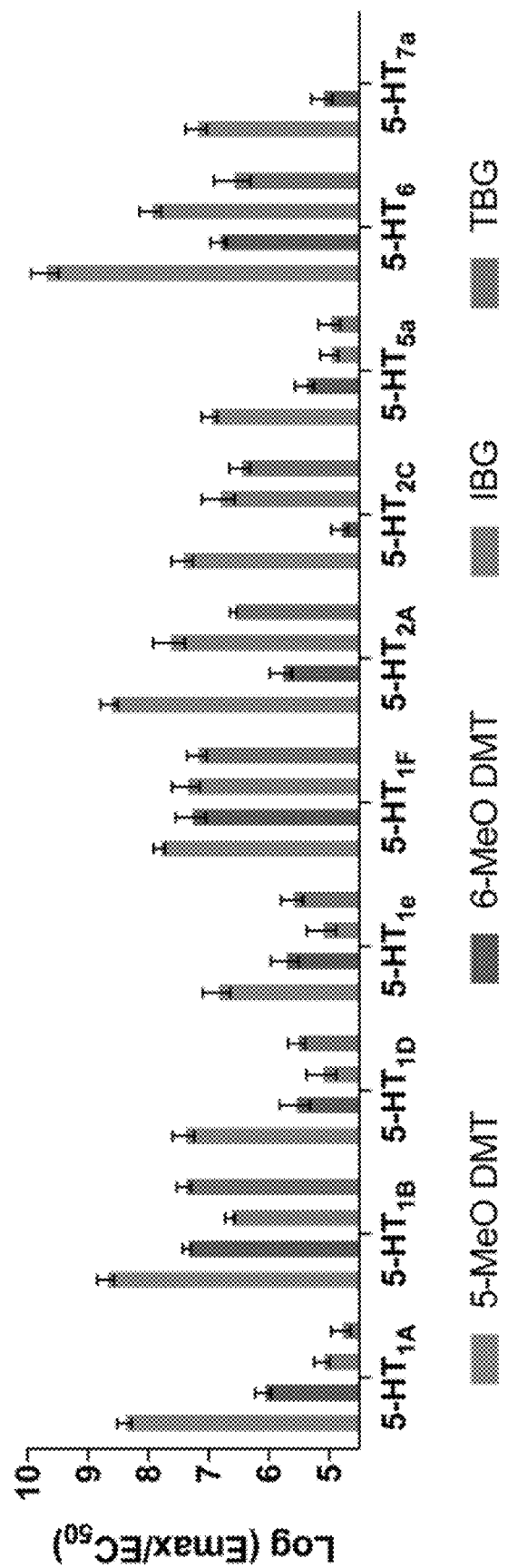
FIG. 14 shows screening of DMT derivatives and ibogalogs reveals differences in 5-HT receptorome profiles. Ibogalogs are more selective $5\text{-}HT_{2A}$ agonists than 5-MeO-DMT.

To validate the targets of IBG and TBG, a panel of serotonin (5-HT) and opioid receptor functional assays assessing canonical GPCR signaling was performed. Unlike noribogaine, IBG and TBG showed weak or no opioid agonist activity (FIG. 12 and FIG. 13). However, IBG and TBG demonstrated potent agonist activity at human (FIG. 2K) and mouse 5-HT2A receptors (FIG. 12). Many 5-HT2A agonists, such as 5-MeO-DMT, are also agonists of 5-HT2B receptors, which can lead to cardiac valvulopathy. Fortunately, IBG and TBG act as antagonists at 5-HT2B receptors (FIG. 2K). When profiled across the 5-HT receptorome, both compounds displayed distinct profiles as compared to 5-MeO-DMT (FIG. 12, FIG. 13, and FIG. 14), including weaker 5-HT1A and 5-HT2C agonist activity. In fact, IBG and TBG exhibit more selective, and potentially safer profiles than the less conformationally restricted 5-MeO-DMT with a strong preference for activating $5\text{-HT}_{2A}$ receptors over similar 5-HT receptors or opioid receptors.

Example 2. Compounds 4a and 4b

To a solution of pyridine (10.0 g, 126.4 mmol, 1.0 equiv) and sodium borohydride (4.8 g, 126.4 mmol, 1.0 equiv) in MeOH (56 mL, 2.3 M) at −78° C. was added benzylchloroformate (18.0 mL, 21.6 g, 126.4 mmol, 1.0 equiv) via slow dropwise addition. Gas evolution was observed. The mixture was stirred for 3 h at −78° C., diluted with Et$_2$O (100 mL) and H$_2$O (50 mL), and warmed to room temperature. The aqueous layer was extracted with Et$_2$O (3×50 mL). The combined organic extracts were washed with brine (3×50 mL), dried over Na$_2$SO$_4$, and concentrated under reduced pressure to yield a clear oil. The produce was passed through a short plug of silica gel using hexanes:EtOAc (95:5) as the eluent. The resulting filtrate was concentrated under reduced pressure. After purging with nitrogen, methyl vinyl ketone (10.5 mL, 126.4 mmol, 1.0 equiv) was added to the flask and the neat solution was heated to 80° C. for 24 h. After cooling the mixture to room temperature, MeOH (250 mL) was added followed by 25% w/w aqueous NaOMe (2.4 mL, 8.9 mmol, 0.07 equiv). The resulting mixture was stirred for 15 min, quenched with H$_2$O (5 mL), then concentrated under reduced pressure. The residue was dissolved in DCM (250 mL) and then washed with H$_2$O (100 mL) followed by brine (50 mL). The organic layer was dried over Na$_2$SO$_4$ and concentrated under reduced pressure. The produce was purified by chromatography on silica gel (3:1 hexanes: EtOAc) to give a clear oil containing a mixture of 4a and 4b (26.5 g, 73% over 3 steps, ~1:1 exo:endo as a mixture of rotamers).

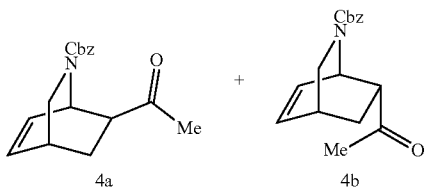 [SMILES: CC(=O)C1CC2C=CC1N(C(=O)OCc1ccccc1)C2 ; CC(=O)C1CC2C=CC1N(C(=O)OCc1ccccc1)C2]

$^1$H NMR (CDCl$_3$, 400 MHz) δ 7.4-7.2 (m, 5H), 6.57-6.23 (m, 2H), 5.22-4.94 (m, 3H), 3.33 (t, $^1$H, J=10.3 Hz), 3.18-2.58 (m, 3H), 2.35-2.05 (m, 3H), 1.91-1.66 (m, 1H), 1.64-1.23 (m, 1H) ppm; IR (Smart iTX Diamond) ν 3060, 2957, 2878, 1699, 1417, 1366, 1337, 1300, 1279, 1113, 764, 699 cm$^{-1}$; LC-MS (ES$^+$) calcd for C$_{17}$H$_{20}$NO$_3$ [M+H] 286.14 found 286.22.

Example 3. Compounds 5a and 5b

To a mixture of 4a and 4b (4.8 g, 17.0 mmol, 1.0 equiv) in anhydrous THF (13 mL, 1.3 M) was added p-toluenesulfonyl hydrazide (3.16 g, 17.0 mmol, 1 equiv). The mixture was refluxed for 15-20 hour until starting material was consumed as determined by TLC. The reaction mixture was concentrated under reduced pressure, siluted with Et$_2$O (20 mL), and sonicated for 15 min. The white precipitate was filtered and washed with Et$_2$O (4×5 mL) to yield 5b. The filtrate was concentrated under reduced pressure and purified by chromatography on silica gel (gradient elution: 5:1→1:1 hexanes:EtOAc) to give 5a (75%; exo=5.88 g, endo=7.33 g, mixture of exo and endo=2.62 g).

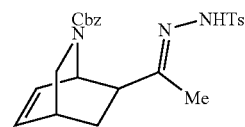

Isolated as a white solid (5.88 g, mixture of rotamers); $^1$H NMR (CDCl$_3$, 400 MHz) δ 7.80 (dd, 2H, J=20.1, 8.3 Hz), 7.43-7.26 (m, 4H), 7.25-7.11 (m, 3H), 6.49-6.36 (m, 2H), 5.10 (dd, 1H, J=36.0, 12.3 Hz), 4.80-4.57 (m, 2H), 3.02 (dd, 1H, J=10.0, 2.1 Hz), 2.92-2.84 (m, 1H), 2.75-2.67 (m, 1H), 2.48-2.13 (m, 5H), 1.89 (s, 2H), 1.59 (s, 1H), 1.47 (s, 1H), 1.39-1.27 (m, 1H) ppm; IR (Smart iTX Diamond) ν 3207, 2952, 2876, 1675, 1418, 1368, 1337, 1303, 1258, 1165, 1117, 1030, 917, 813, 763, 705, 667, 552 cm$^{-1}$; LC-MS (ES+) calcd for C$_{24}$H$_{28}$N$_2$O$_4$S [M+H] 454.18 found 454.33.

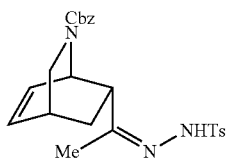

5b

Isolated as a white solid (7.33 g, mixture of rotamers); ¹H NMR (CDCl₃, 400 MHz) δ 7.79 (t, 2H, J=8.9 Hz), 7.42-7.27 (m, 6H), 7.09 (d, 1H, J=8.0 Hz), 6.21 (t, 1H, J=7.3 Hz), 6.08-6.00 (m, 1H), 5.23-5.05 (m, 2H), 4.93-4.82 (m, 1H), 3.33-3.23 (m, 1H), 3.06-2.96 (m, 1H), 2.96-2.86 (m, 1H), 2.81-2.71 (m, 1H), 2.41 (s, 3H), 1.93-1.46 (m, 6H) ppm; IR (Smart iTX Diamond) ν 3105, 2939, 2878, 1671, 1446, 1420, 1372, 1338, 1322, 1298, 1280, 1262, 1241, 1167, 976, 932, 818, 804, 766, 724, 670, 550 cm⁻¹; LC-MS (ES+) calcd for $C_{24}H_{28}N_2O_4S$ [M+H] 454.18 found 454.33.

Example 4. Compounds 6a and 6b

To a solution of 5a or 5b (3.78 g, 8.35 mmol, 1.0 equiv) in THF (16.7 mL, 2 M) was added sodium cyanoborohydride (2.1 g, 33.4 mmol, 4 equiv) and p-toluenesulfonic acid (159 mg, 0.835 mmol, 0.1 equiv). The mixture was refluxed for 18 h, diluted with H₂O (30 mL), and extracted with cyclohexane (5×25 mL). The combined organic extracts were washed with H₂O (20 mL), saturated aqueous NaHCO₃ (20 mL), and brine (20 mL) before being dried over Na₂SO₄ and concentrated under reduced pressure to yield either 6a or 6b.

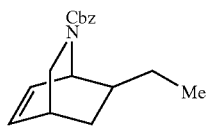

6a

Isolated as a clear oil (2.01 g, 57%, mixture of rotamers); ¹H NMR (CDCl₃, 400 MHz) δ 7.41-7.27 (m, 5H), 6.55-6.38 (m, 1H), 6.33 (q, 1H, J=7.7 Hz), 5.22-5.02 (m, 2H), 4.58 (d, 1H, J=6.1 Hz), 3.30-3.20 (m, 1H), 3.08-2.96 (m, 1H), 2.75-2.58 (m, 1H), 1.69-1.59 (m, 1H), 1.53-1.30 (m, 3H), 1.05-0.98 (m, 1H), 0.98-0.84 (m, 3H) ppm; IR (Smart iTX Diamond) ν 3052, 2957, 2873, 1699, 1417, 1335, 1295, 1106, 986, 764, 699 cm⁻¹; LC-MS (ES+) calcd for $C_{17}H_{21}NO_2$ [M+H] 272.17 found 272.29.

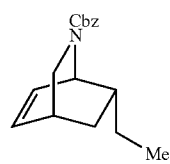

6b

Isolated as a clear oil (2.66 g, 62%, mixture of rotamers); ¹H NMR (CDCl₃, 400 MHz) δ 7.39-7.26 (m, 5H), 6.42-6.22 (m, 2H), 5.18-5.08 (m, 2H), 4.73-4.55 (m, 1H), 3.32-3.20 (m, 1H), 3.04-2.95 (m, 1H), 2.77-2.62 (m, 1H), 2.05-1.91 (m, 1H), 1.87-1.77 (m, 1H), 1.28-1.11 (m, 1H), 1.05-0.82 (m, 5H) ppm; IR (Smart iTX Diamond) ν 3052, 2958, 2931, 2874, 1699, 1416, 1333, 1301, 1276, 1111, 977, 766, 698 cm⁻¹. LC-MS (ES+) calcd for $C_{17}H_{21}NO_2$ [M+H] 272.17 found 272.29.

Example 5. Compounds 8a and 8b

A solution of either 6a or 6b (132 mg, 0.95 mmol, 1.0 equiv) in acetic acid (0.5 mL, 1.9 M) was heated to 55° C. prior to the addition of sodium borohydride (165 mg, 4.37 mmol, 4.6 equiv). Gas evolution was observed. The mixture was stirred at 55° C. for 10 h, diluted with H₂O (2 mL), cooled to 0° C. and basified with solid NaOH (until pH=14). The aqueous layer was extracted with Et₂O (4×10 mL), dried over Na₂SO₄, and concentrated under reduced pressure. The residue was purified by chromatography on silica gel (100:1 DCM:MeOH with 0.5% NH₄OH) to afford product.

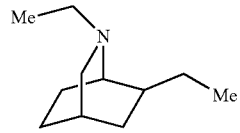

8a

Isolated as a yellow oil (12 mg, 7%); ¹H NMR (CDCl₃, 400 MHz) δ 3.05-2.96 (m, 1H), 2.47 (q, 2H, J=7.2 Hz), 2.37 (t, 1H, J=2.4 Hz), 2.20 (dt, 1H, J=9.3, 1.5 Hz), 2.00-1.89 (m, 1H), 1.73-1.64 (m, 1H), 1.64-1.58 (m, 1H), 1.56-1.36 (m, 5H), 1.32-1.23 (m, 1H), 1.19-1.11 (m, 1H), 1.00 (t, 3H, J=7.2 Hz), 0.86 (t, 3H, J=7.1 Hz) ppm; ¹³C NMR (CDCl₃, 100 MHz) δ 56.67, 51.92, 49.18, 40.36, 32.76, 27.15, 26.89, 25.34, 21.52, 13.64, 11.98 ppm; IR (Smart iTX Diamond) ν 2955, 2926, 2857, 2793, 1458, 1372, 1259, 1100, 1048, 799 cm⁻¹; LC-MS (ES+) calcd for $C_{11}H_{21}N$ [M+H] 168.18 found 168.33.

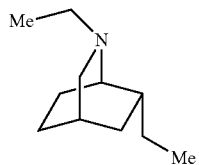

8b

Isolated as a yellow oil (71.5 mg, 47%); ¹H NMR (CDCl₃, 400 MHz) δ 2.76 (dt, 1H, J=9.8, 2.7 Hz), 2.65-2.46 (m, 3H), 2.45-2.39 (m, 1H), 1.91-1.70 (m, 3H), 1.66-1.55 (m, 3H), 1.47-1.37 (m, 1H), 1.35-1.20 (m, 2H), 1.07 (d, 3H, J=14.4 Hz), 0.99 (dt, 1H, J=6.3, 2.2 Hz), 0.88 (t, 3H, J=7.4 Hz) ppm; ¹³C NMR (CDCl₃, 100 MHz) δ 55.71, 52.90, 49.55, 35.32, 32.94, 27.67, 26.63, 25.30, 20.02, 13.47, 12.19 ppm; IR (Smart iTX Diamond) ν 2958, 2931, 2872, 2860, 2792, 1464, 1371, 1217, 1161, 1094, 819, 756 cm⁻¹; LC-MS (ES+) calcd for $C_{11}H_{21}N$ [M+H] 168.17 found 168.25.

Example 6. Preparation of 5-Substituted Tryptophols

General Procedure for Preparing Hydrazines. Most hydrazines were commercially available, however the 4-10 do and 4-benzyloxy hydrazines were synthesized in house according to the following procedure. A 0.5 M solution of 4-substituted aniline (3.99 mmol, 1 equiv) in aqueous concentrated HCl was cooled to 0° C. before the addition of 2.0 M aqueous NaNO₂ (3.91 mmol, 0.98 equiv). The solution was stirred for 20 min at 0° C. Next, a solution of SnCl₂.2H₂O (10.4 mmol, 2.6 equiv) dissolved in concentrated aqueous HCl (2.4 mL) was added. The mixture was stirred for 2 h, warmed to room temperature, filtered, and rinsed with H₂O and Et₂O. The solids were dried under reduced pressure and used immediately without further purification.

All 5-substituted tryptophols were prepared from the corresponding 4-substituted hydrazines as outlined here. General Scheme:

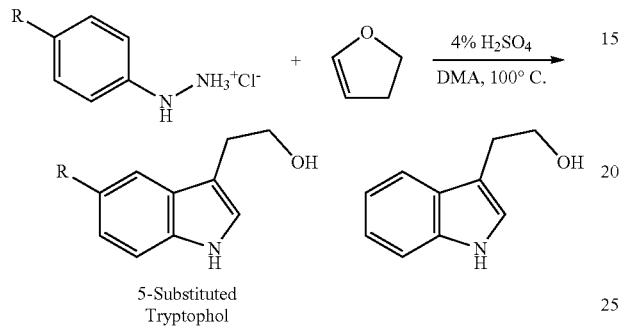

5-Substituted Tryptophol

A solution of phenyl hydrazine (0.5 g, 3.46 mmol, 1 equiv) in 10 mL of a 1:1 mixture of DMA and 4% aqueous H₂SO₄ was heated to 100° C. To this solution was added 1,2-dihydrofuran (0.29 mL, 266 mg, 3.8 mmol, 1.1 equiv) via dropwise addition. The resulting mixture was stirred at 100° C. until starting material was consumed as determined by TLC (~3 h). The reaction was then cooled to room temperature and diluted with EtOAc (10 mL). The aqueous layer was extracted with EtOAc (5×10 mL). The combined organic extracts were washed with 5% aqueous LiCl (15 mL), saturated aqueous NaHCO₃ (15 mL), and H₂O (15 mL) before being dried over Na₂SO₄. The resulting product was purified by chromatography on silica gel (3:1 hexanes:EtOAc) to yield the desired tryptophol as a brown solid (258 mg, 92%); ¹H NMR (CDCl₃, 400 MHz) δ 8.23 (s, 1H), 7.70-7.59 (m, 1H), 7.36 (d, 1H, J=8.1 Hz), 7.25-7.19 (m, 1H), 7.15 (td, 1H, J=7.6, 7.1, 1.0 Hz), 7.09-7.00 (m, 1H), 3.91 (t, 2H, J=6.4 Hz), 3.04 (t, 2H, J=6.4 Hz), 1.86 (s, 1H) ppm; ¹³C NMR (CDCl₃, 100 MHz) δ 136.47, 127.44, 122.54, 122.23, 119.49, 118.86, 112.27, 111.26, 62.64, 28.77 ppm; IR (Smart iTX Diamond) v 3390, 3322, 3059, 2933, 2905, 2863, 1456, 1424, 1352, 1338, 1229, 1094, 1045, 1005, 738, 591 cm⁻¹; LC-MS (ES+) calcd for C₁₀H₁₁NO [M+H] 162.09 found 162.21.

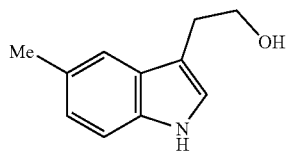 [SMILES: Cc1ccc2[nH]cc(CCO)c2c1]

A solution of p-MeO-phenylhydrazine (2 g, 11.45 mmol, 1 equiv) in 32.6 mL of a 1:1 mixture of DMA and 4% aqueous H₂SO₄ was heated to 100° C. To this solution was added 1,2-dihydrofuran (0.95 mL, 0.883 g, 12.6 mmol, 1.1 equiv) via dropwise addition. The resulting mixture was stirred at 100° C. until starting material was consumed as determined by TLC. The reaction was then cooled to room temperature and diluted with EtOAc (20 mL). The aqueous layer was extracted with EtOAc (4×25 mL). The combined organic extracts were washed with 5% aqueous LiCl (20 mL), saturated aqueous NaHCO₃ (20 mL), and H₂O (20 mL) before being dried over Na₂SO₄. The resulting product was purified by chromatography on silica gel (gradient elution: 3:1→1:1 hexanes:EtOAc) to yield the desired product as a yellow oil (1.71 g, 78%); ¹H NMR (CDCl₃, 400 MHz) δ 8.01 (s, 1H), 7.25 (s, 1H), 7.06 (d, 2H, J=2.5 Hz), 6.88 (dd, 1H, J=8.8, 2.4 Hz), 3.90 (t, 2H, J=6.4 Hz), 3.87 (s, 3H), 3.01 (t, 2H, J=6.4 Hz), 1.70 (s, 1H) ppm; 13C NMR (CDCl₃, 100 MHz) δ 154.09, 131.70, 127.91, 123.46, 112.45, 112.09, 111.97, 100.76, 62.67, 56.06, 28.82 ppm; IR (Smart iTX Diamond) v 3409, 2938, 2831, 1624, 1584, 1486, 1456, 1440, 1214, 1067, 1043, 922, 798 cm⁻¹; LC-MS (ES+) calcd for C₁₁H₁₃NO₂ [M+H] 192.10 found 192.27.

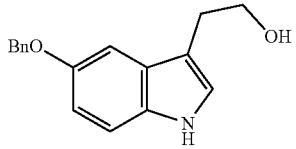 [SMILES: OCCc1c[nH]c2ccc(OCc3ccccc3)cc12]

A solution of p-BnO-phenylhydrazine (398 mg, 1.59 mmol, 1 equiv) in 4.54 mL of a 1:1 mixture of DMA and 4% aqueous H₂SO₄ was heated to 100° C. To this solution was added 1,2-dihydrofuran (0.13 mL, 123 mg, 1.75 mmol, 1.1 equiv) via dropwise addition. The resulting mixture was stirred at 100° C. until starting material was consumed as determined by TLC (~3 h). The reaction was then cooled to room temperature and diluted with EtOAc (10 mL). The aqueous layer was extracted with EtOAc (4×10 mL). The combined organic extracts were washed with 5% aqueous LiCl (10 mL), saturated aqueous NaHCO₃ (10 mL), and H₂O (2×10 mL) before being dried over Na₂SO₄. The resulting product was purified by chromatography on silica gel (gradient elution: 3:1→1:1 hexanes:EtOAc) to yield the desired product as a brown oil (160 mg, 38%); ¹H NMR (CDCl₃, 400 MHz) δ 7.95 (s, 1H), 7.49 (d, 2H, J=7.4 Hz), 7.43-7.30 (m, 3H), 7.26 (s, 1H), 7.15 (d, 1H, J=2.3 Hz), 7.06 (d, 1H, J=2.2 Hz), 6.96 (dd, 1H, J=8.8, 2.4 Hz), 5.12 (s, 2H), 3.89 (t, 2H, J=6.3 Hz), 3.00 (t, 2H, J=6.3 Hz), 1.59 (s, 1H) ppm; ¹³C NMR (CDCl₃, 100 MHz) δ 153.25, 137.61, 131.79, 128.53, 127.85, 127.82, 127.63, 123.34, 113.13, 112.07, 111.93, 102.44, 71.04, 62.59, 28.77 ppm; IR (Smart iTX Diamond) v 3419, 3062, 3032, 2929, 2878, 1624, 1582, 1483, 1454, 1381, 1293, 1219, 1194, 1064, 1043, 1025, 797, 740, 698 cm⁻¹; LC-MS (ES+) calcd for C₁₇H₁₈NO₂[M+H] 268.13 found 268.24.

Example 7. Compounds 9a and 9b

First, the hydroxyl groups of the tryptophols shown above were converted to the iodides. To accomplish this transformation, a solution of iodine (251 mg, 0.99 mmol, 1.4 equiv) and triphenyl phosphine (260 mg, 0.99 mmol, 1.4 equiv) in DCM (2.75 mL, 0.25 M) was cooled to 0° C. Next, a tryptophol (0.71 mmol, 1.0 equiv) was added dropwise. The solution was stirred until starting material had been consumed as determined by TLC (~5 h). The reaction mixture was concentrated under reduced pressure to afford the alkyl iodide, which was used immediately without further purification.

In a separate flask, a mixture of 6a or 6b (271 mg, 1.0 mmol, 1.0 equiv) and 10% Pd/C (85 mg, 0.08 mmol, 0.08 equiv) was stirred in MeOH (5 mL, 0.2 M) under an atmosphere of $N_2$. The flask was then purged with $H_2$ gas and stirred vigorously under an atmosphere of $H_2$ until the starting material had been consumed as determined by TLC (~3 h). The mixture was filtered over a pad of celite, which was washed with 50 mL of MeOH containing 1% aqueous $NH_4OH$. The filtrate was then dried over $Na_2SO_4$ and concentrated under reduced pressure to yield a clear oil. The oil was immediately dissolved in DMF (2.5 mL, 0.4 M) and added to a flask containing the unpurified alkyl iodide (271 mg, 1.0 mmol, 1.0 equiv, generated as described above) and solid $NaHCO_3$ (168 mg, 2 mmol, 2 equiv.). The mixture was heated at 80° C. for 20 h before being cooled to room temperature and diluted with 1M aqueous $Na_2CO_3$ (15 mL) and EtOAc (15 mL). The aqueous layer was extracted with EtOAc (3×10 mL). The combined organic extracts were washed with $H_2O$ (10 mL), 5% aqueous LiCl (10 mL), and brine (10 mL) before being dried over $Na_2SO_4$ and concentrated under reduced pressure. The product was purified by chromatography on silica gel (100:1 DCM:MeOH with 0.5% $NH_4OH$).

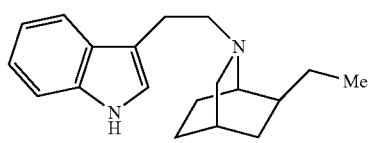

9a

Isolated as a tan solid (30 mg, 24%, 2 steps); $^1$H NMR (CDCl$_3$, 400 MHz) δ 7.95 (s, 1H), 7.64 (d, 1H, J=7.8 Hz), 7.35 (d, 1H, J=8.0 Hz), 7.24-7.16 (m, 1H), 7.16-7.10 (m, 1H), 7.05 (d, 1H, J=1.8 Hz), 3.19-3.12 (m, 1H), 2.96-2.72 (m, 4H), 2.49 (s, 1H), 2.36 (d, 1H, J=9.2 Hz), 2.09-1.99 (m, 1H), 1.79-1.71 (m, 1H), 1.71-1.65 (m, 1H), 1.63-1.42 (m, 5H), 1.40-1.31 (m, 1H), 1.24-1.16 (m, 1H), 0.90 (t, 3H, J=7.1 Hz) ppm; 13C NMR (CDCl3, 100 MHz) δ 136.29, 127.83, 121.84, 121.65, 119.13, 119.04, 115.21, 111.15, 56.89, 56.82, 53.30, 40.62, 32.87, 27.44, 26.95, 25.35, 24.40, 21.97, 12.04 ppm; IR (Smart iTX Diamond) v 3418, 3170, 3055, 2930, 2860, 2798, 1456, 1357, 1228, 1147, 1092, 740 cm$^{-1}$; LC-MS (ES+) calcd for $C_{19}H_{26}N_2$ [M+H] 283.22 found 283.35.

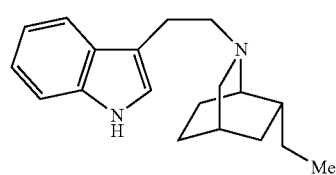

9b

Isolated as a tan solid (66 mg, 23%, 2 steps); $^1$H NMR (CDCl$_3$, 400 MHz) δ 8.07 (s, 1H), 7.65 (d, 1H, J=7.8 Hz), 7.35 (d, 1H, J=8.0 Hz), 7.19 (t, 1H, J=7.4 Hz), 7.12 (t, 1H, J=7.4 Hz), 7.07-7.03 (m, 1H), 3.01-2.91 (m, 3H), 2.91-2.83 (m, 2H), 2.77-2.70 (m, 1H), 2.55-2.50 (m, 1H), 1.97-1.78 (m, 3H), 1.73-1.56 (m, 3H), 1.52-1.41 (m, 1H), 1.36-1.26 (m, 2H), 1.08-1.00 (m, 1H), 0.89 (t, 3H, J=7.4 Hz) ppm; $^{13}$C NMR (CDCl$_3$, 100 MHz) δ 136.37, 127.73, 122.03, 121.65, 119.30, 119.10, 114.97, 111.21, 57.30, 56.20, 53.91, 35.48, 32.92, 27.68, 26.67, 25.26, 24.39, 20.15, 12.19 ppm; IR (Smart iTX Diamond) v 3416, 3139, 3055, 2926, 2858, 2823, 1456, 1354, 1231, 1112, 1088, 738 cm$^{-1}$; LC-MS (ES+) calcd for $C_{19}H_{26}N_2$ [M+H] 283.22 found 283.35.

Example 8. Compounds 10a, and 10b

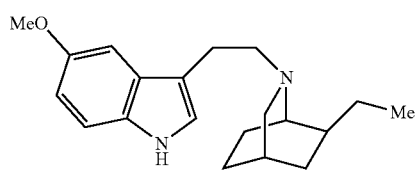

10a

Isolated as an amorphous brown solid (71.2 mg, 44%, 2 steps); $^1$H NMR (CDCl$_3$, 400 MHz) δ 8.05 (s, 1H), 7.23 (d, 1H, J=8.7 Hz), 7.09 (d, 1H, J=2.0 Hz), 7.04-6.98 (m, 1H), 6.86 (dd, 1H, J=8.8, 2.3 Hz), 3.88 (s, 3H), 3.27-3.12 (m, 1H), 2.96-2.76 (m, 4H), 2.54 (s, 1H), 2.37 (d, 1H, J=9.3 Hz), 2.11-1.98 (m, 1H), 1.81-1.72 (m, 1H), 1.72-1.65 (m, 1H), 1.65-1.43 (m, 5H), 1.42-1.33 (m, 1H), 1.28-1.16 (m, 1H), 0.91 (t, 3H, J=7.1 Hz) ppm; $^{13}$C NMR (CDCl$_3$, 100 MHz) δ 153.91, 131.50, 128.16, 122.60, 114.58, 111.97, 111.87, 101.05, 56.85, 56.57, 56.13, 53.35, 40.43, 32.66, 27.38, 26.78, 25.15, 24.20, 21.90, 12.03 ppm; IR (Smart iTX Diamond) v 3415, 3045, 2931, 2860, 2828, 1624, 1585, 1485, 1456, 1215, 1172, 1064, 1032, 796 cm$^{-1}$; LC-MS (ES+) calcd for C20H29N2O [M+H] 313.23 found 313.34.

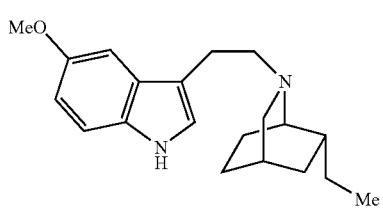

10b

Isolated as an amorphous brown solid (56 mg, 18%, 2 steps); $^1$H NMR (CDCl$_3$, 400 MHz) δ 8.67 (s, 1H), 7.23 (d, 1H, J=8.8 Hz), 7.08 (d, 1H, J=2.3 Hz), 7.00 (d, 1H, J=1.9 Hz), 6.86 (dd, 1H, J=8.8, 2.4 Hz), 3.85 (s, 3H), 3.02-2.93 (m, 3H), 2.93-2.86 (m, 2H), 2.80-2.73 (m, 1H), 2.63-2.56 (m, 1H), 2.02-1.83 (m, 3H), 1.75-1.59 (m, 3H), 1.55-1.44 (m, 1H), 1.40-1.29 (m, 2H), 1.07 (m, 1H), 0.92 (t, 3H, J=7.4 Hz) ppm; $^{13}$C NMR (CDCl$_3$, 100 MHz) δ 153.77, 131.57, 127.99, 122.66, 114.24, 114.21, 111.94, 100.83, 57.10, 56.10, 55.99, 53.63, 35.34, 32.87, 27.58, 26.60, 25.23, 24.32, 20.10, 12.14 ppm; IR (Smart iTX Diamond) v 3412, 3041, 2930, 2871, 2827, 1625, 1586, 1486, 1456, 1216, 1173, 1064, 1032, 795 cm$^{-1}$; LC-MS (ES+) calcd for $C_{20}H_{29}N_2O$ [M+H] 313.23 found 313.34.

Example 9. Compound 11a and 11b

First, the 5-benzyloxy-isoquinuclidine was synthesized as described above. Next, this starting material (100 mg, 0.26 mmol, 1.0 equiv) was dissolved MeOH (1.3 mL, 0.2 M) containing 10% Pd/C (22 mg, 0.02 mmol, 0.08 equiv) under a $N_2$ atmosphere. The flask was then purged with $H_2$ gas and stirred vigorously under an atmosphere of $H_2$ until the starting material had been consumed as determined by TLC (~24 h). The mixture was filtered over a pad of celite, which was washed with 50 mL of MeOH containing 1% aqueous NH$_4$OH. The filtrate was then dried over Na$_2$SO$_4$ and concentrated under reduced pressure to yield a brown oil. The product was purified by chromatography on silica gel (30:1 DCM:MeOH with 1% NH$_4$OH)

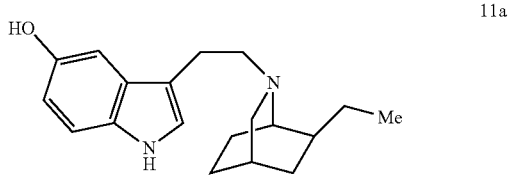 [SMILES: CCC1CC2CCC1N(CCc1c[nH]c3ccc(O)cc13)C2]

11a

Isolated as a tan foam (32 mg, 41%, 3 steps); $^1$H NMR (CDCl$_3$, 400 MHz) δ 7.96 (s, 1H), 7.14 (d, 1H, J=8.6 Hz), 6.94 (s, 1H), 6.83 (d, 1H, J=1.8 Hz), 6.80-6.72 (dd, 1H, J=8.6, 1.8 Hz), 5.74 (bs, 1H), 3.13 (dt, 1H, J=9.2, 2.9 Hz), 2.93-2.71 (m, 4H), 2.56-2.49 (m, 1H), 2.35 (d, 1H, J=9.5 Hz), 2.08-1.95 (m, 1H), 1.80-1.71 (m, 1H), 1.70-1.64 (m, 1H), 1.63-1.40 (m, 5H), 1.39-1.17 (m, 2H), 0.88 (t, 3H, J=7.1 Hz) ppm; $^{13}$C NMR (CDCl$_3$, 100 MHz) δ 149.82, 131.40, 128.36, 122.85, 114.05, 112.26, 111.91, 103.71, 56.99, 56.59, 53.67, 40.64, 32.59, 27.43, 26.66, 25.01, 23.95, 22.08, 12.17 ppm; IR (Smart iTX Diamond) ν 3400, 3278, 2929, 2860, 1625, 1581, 1456, 1362, 1186, 1092, 936, 796, 754 cm$^{-1}$; LC-MS (ES+) calcd for C$_{19}$H$_{27}$N$_2$O [M+H] 299.21 found 299.34.

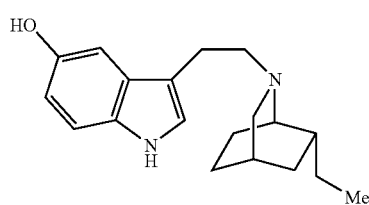

11b

Isolated as a tan foam (20 mg, 15%, 3 steps); $^1$H NMR (CDCl$_3$, 600 MHz) δ 7.98 (s, 1H), 7.16 (d, 1H, J=8.6 Hz), 6.94 (s, 1H), 6.88 (d, 1H, J=2.0 Hz), 6.78 (dd, 1H, J=8.6, 2.2 Hz), 3.03-2.92 (m, 4H), 2.76-2.71 (m, 1H), 2.62-2.57 (m, 1H), 2.01-1.82 (m, 3H), 1.69 (s, 1H), 1.67-1.57 (m, 2H), 1.48-1.41 (m, 1H), 1.35-1.19 (m, 3H), 1.05-0.99 (m, 1H), 0.83 (t, 3H, J=7.4 Hz) ppm; $^{13}$C NMR (CDCl$_3$, 150 MHz) δ 150.66, 131.34, 128.18, 122.68, 113.51, 113.03, 112.03, 103.77, 57.33, 55.57, 54.52, 34.85, 32.65, 27.52, 26.35, 24.90, 24.01, 19.49, 12.09 ppm; IR (Smart iTX Diamond) ν 3402, 3286, 2924, 2857, 1625, 1581, 1456, 1377, 1208, 1080, 936, 795, 751 cm$^{-1}$; LC-MS (ES+) calcd for C$_{19}$H$_{27}$N$_2$O [M+H] 299.21 found 299.34.

Example 10. Compound 12

To a solution of 4-substituted phenyl hydrazine hydrochloride (1.0 mmol) in EtOH (0.1 M) was added 1-methyl-azepan-4-one hydrochloride (164 mg, 1.0 mmol, 1.0 equiv) followed by concentrated aqueous HCl (0.5 mL, 6.0 mmol, 6.0 equiv). The mixture was refluxed for 24 h and then concentrated under reduced pressure. The oily residue was dissolved in DCM (~25 mL) and basified with 1M aqueous NaOH (~20 mL). The aqueous layer was extracted with DCM (3×20 mL). The combined organic extracts were dried over Na$_2$SO$_4$ and concentrated under reduced pressure to yield an oil that was purified by chromatography on silica gel (20:1 DCM:MeOH with 0.5% NH$_4$OH).

General Scheme:

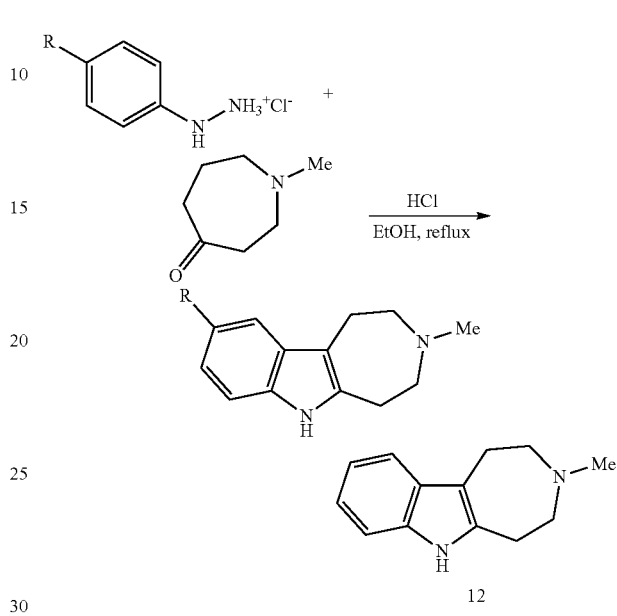

Isolated as a brown solid (127 mg, 64%); $^1$H NMR (CDCl$_3$, 400 MHz) δ 7.78 (s, 1H), 7.50-7.43 (m, 1H), 7.28 (d, 1H, J=1.6 Hz), 7.15-7.05 (m, 2H), 3.01-2.92 (m, 4H), 2.92-2.82 (m, 4H), 2.53 (s, 3H) ppm; $^{13}$C NMR (CDCl$_3$, 100 MHz) δ 136.10, 134.68, 129.05, 121.12, 119.36, 117.74, 112.89, 110.44, 58.05, 56.30, 46.16, 28.59, 23.95 ppm; IR (Smart iTX Diamond) ν 3140, 3055, 3032, 2904, 2829, 2756, 1451, 1337, 739 cm$^{-1}$; LC-MS (ES$^+$) calcd for C$_{13}$H$_{17}$N$_2$ [M+H] 201.14 found 201.33.

Example 11. Compound 13

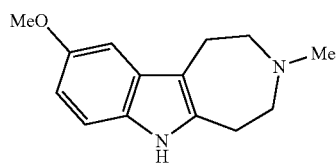

13

Isolated as a light brown solid (146 mg, 63%; $^1$H NMR (CDCl$_3$, 400 MHz) δ 7.74 (s, 1H), 7.15 (d, 1H, J=8.7 Hz), 6.92 (d, 1H, J=2.4 Hz), 6.77 (dd, 1H, J=8.7, 2.4 Hz), 3.85 (s, 3H), 2.98-2.82 (m, 8H), 2.53 (s, 3H) ppm; $^{13}$C NMR (100 MHz, CDCl$_3$) δ 154.13, 137.12, 129.79, 129.40, 112.70, 111.15, 110.91, 100.13, 58.04, 56.29, 56.11, 46.15, 28.61, 24.00 ppm. IR (Smart iTX Diamond) ν 3136, 3035, 2924, 2882, 2822, 1594, 1451, 1215, 1107, 1035, 837, 791 cm$^{-1}$; LC-MS (ES$^+$) calcd for C$_{14}$H$_{19}$N$_2$O [M+H] 231.15 found 231.32.

Example 12. Compound 14

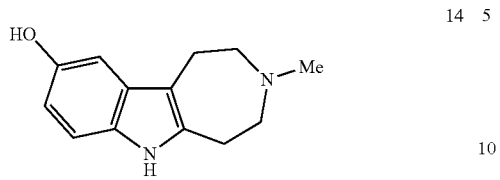

Synthesized from the p-benzyloxyhydrazine followed by hydrogenolysis of the benzyl group. Following Fisher indole cyclization, the benzyloxy indole was added to a mixture of 10% Pd/C (0.08 equiv) in MeOH (4.6 mL) under an atmosphere of $N_2$. The slurry was stirred at room temperature for 12 hours, filtered over a small pad of Celite, and rinsed with 50 mL of methanol and 1% ammonium hydroxide. The filtrates were concentrated under reduced pressure to a brown oil. The desired product was purified by chromatography on silica gel (30:1 DCM:MeOH with 0.5% $NH_4OH$) to yield a white crystalline solid (80 mg, 40%, two steps). $^1H$ NMR (DMSO-$d_6$, 400 MHz) δ 10.32 (s, 1H), 8.46 (s, 1H), 6.99 (d, 1H, J=8.5 Hz), 6.65 (d, 1H, J=2.2 Hz), 6.47 (dd, 1H, J=8.5, 2.2 Hz), 2.87-2.79 (m, 2H), 2.70-2.68 (m, 6H), 2.39 (s, 3H) ppm; $^{13}C$ NMR (DMSO-$d_6$, 100 MHz) δ 150.18, 137.63, 129.39, 129.05, 111.02, 110.58, 110.00, 101.62, 57.95, 56.14, 45.80, 27.76, 23.70 ppm; IR (Smart iTX Diamond) ν 3391, 3273, 3047, 2927, 1590, 1455, 1200, 1111, 928, 840, 797, 735 $cm^{-1}$. LC-MS ($ES^+$) calcd for $C_{13}H_{17}N_2O$ [M+H] 217.13 found 217.32.

Example 13. Compound 15

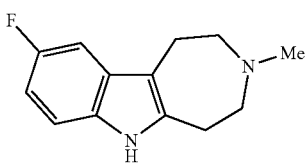

Isolated as a yellow solid (97 mg, 88%); $^1H$ NMR (CDCl$_3$, 400 MHz) δ 7.79 (s, 1H), 7.16 (dd, 1H, J=8.8, 4.4 Hz), 7.09 (dd, 1H, J=9.77, 2.37 Hz), 6.84 (td, 1H, J=9.0, 2.4 Hz), 3.01-2.92 (m, 2H), 2.91-2.80 (m, 6H), 2.52 (s, 3H) ppm. $^{13}C$ NMR (CDCl$_3$, 100 MHz) δ 158.01 (d, J=233.9 Hz), 138.24, 131.12, 129.50 (d, J=9.5 Hz), 113.23 (d, J=4.6 Hz), 110.90 (d, J=9.7 Hz), 109.11 (d, J=26.3 Hz), 102.86 (d, J=23.4 Hz), 57.95, 56.19, 46.21, 28.77, 24.09 ppm. IR (Smart iTX Diamond) ν 3146, 3103, 3040, 2929, 2880, 2809, 2753, 1584, 1453, 1169, 1103, 932, 855, 794, 767, 749 $cm^{-1}$. LC-MS ($ES^+$) calcd for $C_{13}H_{16}FN_2$ [M+H] 219.13 found 219.31.

Example 14. Compound 16

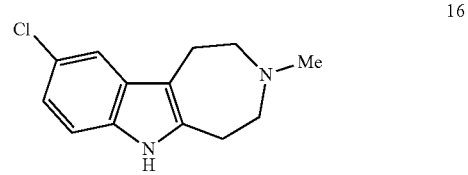 [SMILES: CN1CCc2[nH]c3ccc(Cl)cc3c2CC1]

Isolated as a yellow solid (89 mg, 62%); $^1H$ NMR (CDCl$_3$, 400 MHz) δ 7.99 (s, 1H), 7.41 (d, 1H, J=1.7 Hz), 7.14 (d, 1H, J=8.5 Hz), 7.04 (dd, 1H, J=8.5, 1.9 Hz), 2.98-2.79 (m, 8H), 2.52 (s, 3H) ppm; $^{13}C$ NMR (CDCl$_3$, 100 MHz) δ 137.82, 133.01, 130.16, 125.00, 121.13, 117.33, 112.68, 111.37, 57.84, 56.08, 46.04, 28.55, 23.85 ppm; IR (Smart iTX Diamond) ν 3128, 3085, 3020, 2922, 2849, 2736, 2694, 1446, 1361, 1316, 1052, 917, 851, 783, 718, 601 $cm^{-1}$. LC-MS ($ES^+$) calcd for $C_{13}H_{16}ClN_2$ [M+H] 235.10 found 235.30.

Example 15. Compound 17

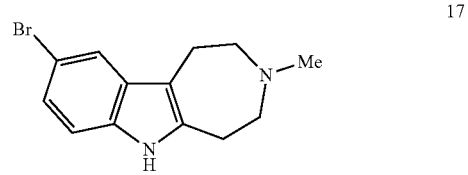 [SMILES: CN1CCc2[nH]c3ccc(Br)cc3c2CC1]

Isolated as a brown solid (161 mg, 65%); $^1H$ NMR (CDCl$_3$, 400 MHz) δ 7.93 (s, 1H), 7.57 (d, 1H, J=1.24 Hz), 7.17 (dd, 1H, J=8.5, 1.5 Hz), 7.10 (d, 1H, J=8.5 Hz), 2.99-2.77 (m, 8H), 2.52 (s, 3H) ppm; $^{13}C$ NMR (CDCl$_3$, 100 MHz) δ 137.66, 133.27, 130.84, 123.71, 120.45, 112.66, 112.58, 111.82, 57.86, 56.11, 46.12, 28.62, 23.91 ppm; IR (Smart iTX Diamond) ν 3126, 3082, 3020, 2922, 2848, 2733, 1575, 1450, 1316, 1113, 1046, 914, 852, 781, 739, 594 $cm^{-1}$. LC-MS ($ES^+$) calcd for $C_{13}H_{16}BrN_2$ [M+H] 279.05 found 279.22.

Example 16. Compound 18

Compound 18 (TBG), was prepared analogously to compounds 12-17 with slight modifications.

General Scheme:

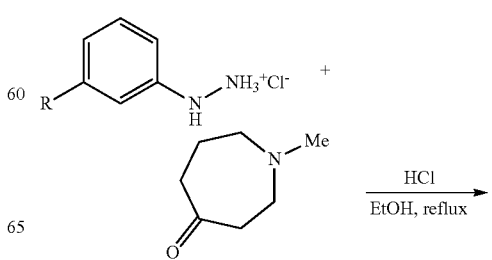

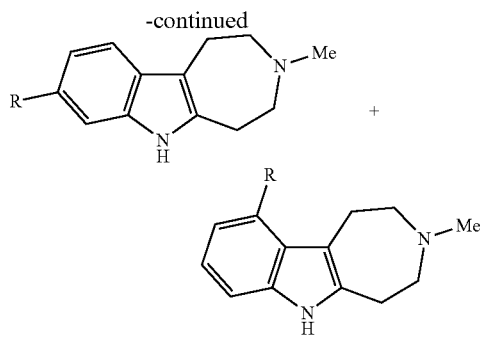

To an ice-cold solution of aqueous 6 M HCl (15 mL) was added 3-methoxyaniline (2.2 ml, 20.0 mmol, 1.0 equiv) dropwise. Next, NaNO$_2$ (1.520 g, 22.0 mmol, 1.1 equiv) was dissolved in H$_2$O (15 mL) and added to the solution slowly. After stirring at 0° C. for 15 minutes, SnCl$_2$ (11.4 g, 60.0 mmol, 3.0 equiv) dissolved in concentrated aqueous HCl (15 mL) was added to the solution dropwise. After stirring at 0° C. for 2.5 h, the reaction mixture was filtered, washed with hexanes, and dried under reduced pressure to yield the product as a light yellow solid that was used without further purification.

To a solution of 3-methoxyphenylhydrazine hydrochloride (1.566 g, 9.0 mmol, 3.0 equiv) in 0.1 M EtOH (30 mL) was added 1-methylazepan-4-one hydrochloride (489 mg, 3.0 mmol, 1.0 equiv) followed by concentrated aqueous HCl (1.0 mL, 12.0 mmol, 4.0 equiv). The mixture was refluxed for 12 h and then concentrated under reduced pressure. The oily residue was dissolved in DCM (~25 mL) and basified with 1M aqueous NaOH (~20 mL). The aqueous layer was extracted with DCM (3×20 mL). The combined organic extracts were dried over Na$_2$SO$_4$ and concentrated under reduced pressure to yield a mixture of the 6- and 4-substituted indoles. The 6-substituted indole was purified by chromatography on silica gel (10:1 DCM:MeOH with 0.5% NH$_4$OH).

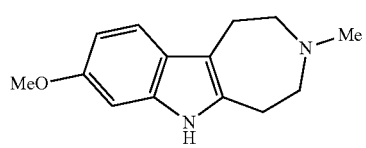

Isolated as light yellow solid (379 mg, 55%); $^1$H NMR (CDCl$_3$, 400 MHz) δ 7.67 (br s, 1H), 7.32 (d, 1H, J=8.5 Hz), 6.80-6.73 (m, 2H), 3.83 (s, 3H), 2.98-2.83 (m, 8H), 2.53 (s, 3H) ppm; $^{13}$C NMR (CDCl$_3$, 100 MHz) δ 155.93, 135.33, 134.68, 123.59, 118.29, 112.53, 108.80, 94.66, 57.98, 56.34, 55.95, 45.93, 28.36, 23.91 ppm; IR (Smart iTX Diamond) ν 3153, 3121, 3073, 2940, 2879, 1628, 1458, 1197, 1033, 910, 834, 799 cm$^{-1}$; LC-MS (ES$^+$) calcd for C$_{14}$H$_{19}$N$_2$O [M+H] 231.15 found 231.36.

Example 17. Procedure for Preparing Compound 13•½ Fumarate

Fumaric acid (116 mg, 1.0 mmol, 0.8 equiv) was added to a sealed tube containing acetone (12 mL). The solution was carefully heated until all of the fumaric acid dissolved. After cooling the solution to room temperature, a solution of 13 free base (288 mg, 1.25 mmol, 1.0 equiv) in acetone (1 mL) was added, and the mixture was cooled in the freezer overnight. The solid was filtered, washed with acetone, and dried under reduced pressure to yield 13•fumarate as the 2:1 salt (220 mg, 61%); $^1$H NMR (CD$_3$OD, 400 MHz) δ 7.15 (d, 1H, J=8.7 Hz), 6.92 (s, 1H), 6.72 (d, 1H, J=8.7 Hz), 6.68 (s, 1H), 3.80 (s, 3H), 3.42-3.34 (m, 4H), 3.18 (t, 2H, J=5.5 Hz), 3.10 (t, 2H, J=5.5 Hz), 2.91 (s, 3H) ppm; $^{13}$C NMR (CD$_3$OD, 100 MHz) δ 171.76, 155.37, 136.32, 135.55, 131.75, 129.59, 112.49, 112.31, 110.58, 100.58, 58.77, 56.70, 56.27, 44.77, 25.09, 21.55 ppm. IR (Smart iTX Diamond) ν 3384, 2979, 2924, 2297, 2822, 1695, 1551, 1353 1167, 982, 912, 802 cm$^{-1}$; LC-MS (ES$^+$) calcd for C$_{14}$H$_{19}$N$_2$O [M+H] 231.15 found 231.36.

Example 18. Procedure for Preparing Compound 18 •Fumarate

Fumaric acid (77 mg, 0.66 mmol, 0.8 equiv) was added to a sealed tube containing acetone (8 mL). The solution was carefully heated until all of the fumaric acid dissolved. After cooling the solution to room temperature, a solution of 18 free base (193 mg, 0.84 mmol, 1.0 equiv) in acetone (1 mL) was added, and the mixture was cooled in the freezer overnight. The solid was filtered, washed with acetone, and dried under reduced pressure to yield 18 •fumarate as the 1:1 salt (187 mg, 64%). $^1$H NMR (CD$_3$OD, 400 MHz) δ 7.28 (d, 1H, J=8.7 Hz), 6.82 (s, 1H), 6.71 (s, 2H), 6.68 (d, 1H, J=8.7 Hz), 3.79 (s, 3H), 3.54-3.45 (m, 4H), 3.22 (t, 2H, J=5.3 Hz), 3.13 (t, 2H, J=5.3 Hz), 3.00 (s, 3H) ppm; $^{13}$C NMR (CD$_3$OD, 100 MHz) δ 170.71, 157.57, 137.23, 135.99, 133.23, 123.71, 118.86, 110.47, 110.10, 95.31, 58.62, 56.68, 55.99, 44.48, 24.77, 21.35 ppm; IR (Smart iTX Diamond) ν 3375, 3008, 2899, 2505, 1694, 1556, 1337, 1162, 1034, 967, 814, 775 cm$^{-1}$; LC-MS (ES$^+$) calcd for C$_{14}$H$_{19}$N$_2$O [M+H] 231.15 found 231.36.

Example 19. Procedure for the Large Scale Preparation of Compound 18 •Fumarate

To an ice-cold solution of aqueous 6 M HCl (30 mL) was added 3-methoxyaniline (4.4 ml, 40.0 mmol, 1.0 equiv) dropwise. Next, NaNO$_2$ (3.040 g, 44.0 mmol, 1.1 equiv) was dissolved in H$_2$O (30 mL) and added to the solution slowly. After stirring at 0° C. for 15 minutes, SnCl$_2$ (22.8 g, 120.0 mmol, 3.0 equiv) dissolved in concentrated aqueous HCl (30 mL) was added to the solution dropwise. After stirring at 0° C. for 2.5 h, the reaction mixture was filtered, washed with hexanes, and dried under reduced pressure to yield 3-methoxyphenylhydrazine hydrochloride as a light yellow solid (5.4 g, 78%) that was used without further purification.

To a solution of 3-methoxyphenylhydrazine hydrochloride (4.802 g, 27.6 mmol, 3.0 equiv) in 0.15 M EtOH (60 mL) was added 1-methylazepan-4-one hydrochloride (1.5 g, 9.2 mmol, 1.0 equiv) followed by concentrated aqueous HCl (3.1 mL, 36.8 mmol, 4.0 equiv). The mixture was refluxed for 12 h and then concentrated under reduced pressure. The oily residue was dissolved in DCM (~50 mL) and basified with 1M aqueous NaOH (~50 mL). The aqueous layer was extracted with DCM (3×30 mL). The combined organic extracts were dried over Na$_2$SO$_4$ and concentrated under reduced pressure to yield a mixture of the 6- and 4-substituted indoles. Addition of EtOAc to the unpurified product mixture resulted in precipitation of the 6-substituted isomer, which was isolated via filtration. The mother liquor was concentrated, and this procedure was repeated six times until a total of 1.028 g of tabernanthalog free base (49%) was collected.

Next, fumaric acid (408 mg, 3.5 mmol, 0.8 equiv) was added to a sealed tube containing acetone (20 mL). The solution was carefully heated until all of the fumaric acid dissolved. After cooling the solution to room temperature, a solution of 18 free base (1.028 mg, 4.4 mmol, 1.0 equiv) in acetone (5 mL) was added dropwise, and the mixture was cooled in the freezer overnight. The solid was filtered, washed with acetone, and dried under reduced pressure to yield 18 •fumarate as the 1:1 salt (1.055 g, 69%).

Example 20. General Procedure for Examples 21 to 24

General Synthetic Scheme:

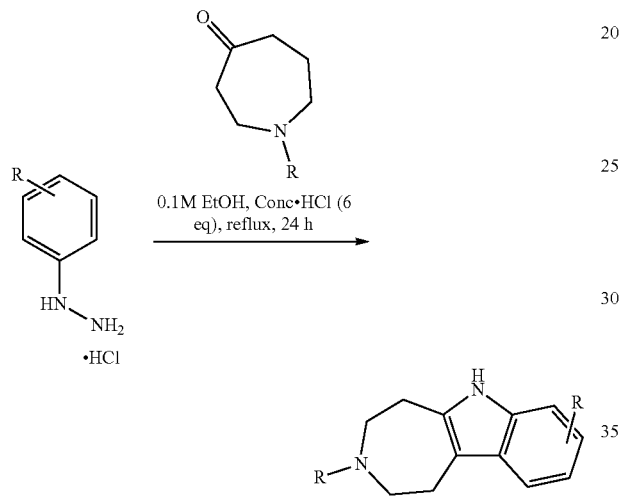

General Procedure:

To a solution of substituted phenyl hydrazine hydrochloride (1.0 mmol) in EtOH (0.1 M) was added 1-methylazepan-4-one hydrochloride (1.0 equiv) followed by concentrated aqueous HCl (6.0 equiv). The mixture was refluxed for 24 h and the progress of the reaction is monitored by TLC.

Work up and purification Procedure: after completion of the reaction, the reaction mixture was concentrated under reduced pressure. The oily residue was dissolved in DCM (~25 mL) and basified with 1M aqueous NaOH (~20 mL). The aqueous layer was extracted with DCM (3×20 mL). The combined organic extracts were dried over $Na_2SO_4$ and concentrated under reduced pressure to yield an oil that was purified by combi-flash using 0.5% $NH_4OH$ with varying % of MeOH in $CH_2Cl_2$. The cleaner fractions by TLC were evaporated and then the obtained residue was diluted with EtOAc and washed with water for couple of times. The organic layer was separated and then evaporated and dried to get pure product.

A few compounds are purified by prep-HPLC purification and the purification methods are captured at respective target compounds.

Example 21. Compound 19

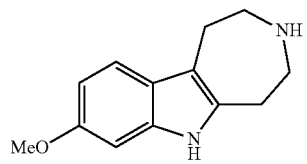

Yield: 150 mg (8%, Off white solid). LCMS: 99%, m/z=217.1 [M+H]$^{+1}$H NMR (DMSO-$d_6$, 400 MHz): δ 10.42 (s, 1H), 7.20 (d, J=8.56 Hz, 1H), 6.72 (d, J=2.20 Hz, 1H), 6.57 (dd, J=2.20, 8.56 Hz, 1H), 3.72 (s, 3H), 2.87-2.91 (m, 4H), 2.79-2.82 (m, 2H), 2.68-2.72 (m, 2H).

Example 22. Compound 20 & Compound 21

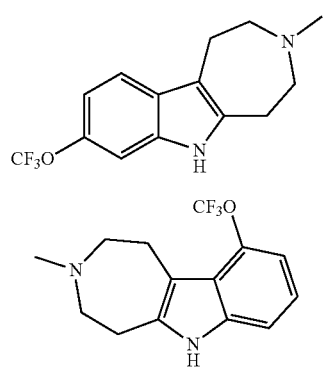

The crude was purified by prep-HPLC to get fraction-1 and fraction-2. Fraction-2 is the above left compound by $^1$H NMR whereas fraction-1 is the above right compound.

Prep-HPLC Purification Method:
Preparative HPLC Column: Viridis BEH-2 EP OBD (250*19 mm, 5µ)
Mobile Phase A: 0.1% DEA in n-Hexane
Mobile Phase B: EtOH: MeOH (50:50)
Flow rate: 16.0 mL/min
Isocratic Table

| Time | % A | % B |
| --- | --- | --- |
| 0 | 90 | 10 |
| 25 | 90 | 10 |

Solvents used for dilution: Methanol/Ethanol

Compound 20: Yield: 12.8% (80 mg, pale brown solid). LCMS: 99.2%, m/z=285.2 [M+H]$^+$ $^1$H NMR (DMSO-$d_6$, 400 MHz): δ 10.97 (s, 1H), 7.43 (d, J=8.56 Hz, 1H), 7.18 (d, J=0.86 Hz, 1H), 6.87-6.92 (m, 1H), 2.88-2.93 (m, 2H), 2.72-2.83 (m, 6H), 2.41 (s, 3H).

Compound 21: Yield: 1.6% (10 mg, Off white solid). LC-MS: 99.6%, m/z=285.2 [M+H]$^+$ $^1$H NMR (DMSO-$d_6$, 400 MHz): δ 11.20 (br s, 1H), 7.27 (d, J=8.07 Hz, 1H), 7.02

(t, J=7.95 Hz, 1H), 6.87 (br d, J=7.09 Hz, 1H), 2.97-3.00 (m, 2H), 2.91-2.94 (m, 2H), 2.69-2.73 (m, 4H), 2.40 (s, 3H).

Example 23. Compound 22

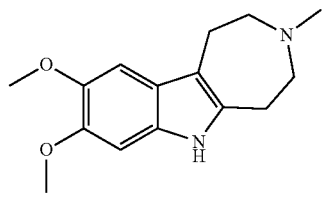

Prep-HPLC Purification Method:
Preparative HPLC Column: X-select CSH C18 (250*19 mm), 5 um
Mobile Phase A: Acetonitrile
Mobile Phase B: 0.05% Ammonia in H20
Flow rate: 15.0 mL/min
Gradient Table

| Time | % A | % B |
| --- | --- | --- |
| 0.01 | 20 | 80 |
| 3.00 | 20 | 80 |
| 20.00 | 30 | 70 |
| 24.00 | 30 | 70 |
| 24.10 | 100 | 0 |
| 30.00 | 100 | 0 |
| 30.10 | 20 | 80 |
| 35.00 | 20 | 80 |

Solvents used for dilution: Acetonitrile/MeOH

Yield: 15.6% (30 mg, Off white solid). LCMS: 99.6%, m/z=261.1 [M+H]$^+$ $^1$H NMR (DMSO-d$_6$, 400 MHz): δ 10.32 (s, 1H), 6.87 (s, 1H), 6.76 (s, 1H), 3.73 (d, J=1.59 Hz, 6H), 2.81-2.85 (m, 2H), 2.68-2.74 (m, 6H), 2.39 (s, 3H).

Example 24. Compound 23

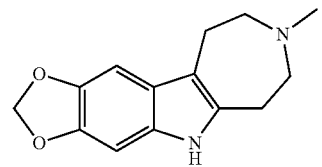

Yield: 220 mg (34%, Pale brown solid). LCMS: 100%, m/z=245.1 [M+H]$^+$ $^1$H NMR (DMSO-d$_6$, 400 MHz): δ 10.45 (br s, 1H), 6.84 (s, 1H), 6.75 (s, 1H), 5.86 (s, 2H), 2.79-2.82 (m, 2H), 2.68 (br s, 6H), 2.37 (s, 3H).

Example 25. Compound 24 & Compound 25

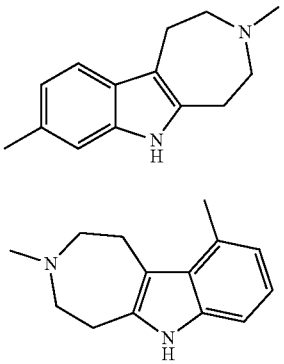

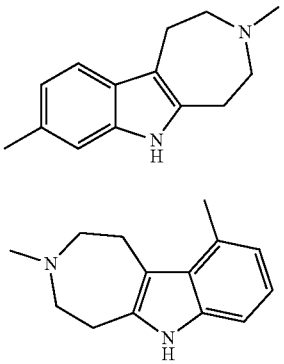

The crude was purified by prep-HPLC to get fraction-1 and fraction-2. The fraction-1 is # (left) by $^1$H NMR whereas fraction-2 is # (right).

Prep-HPLC Purification Method:
Preparative HPLC Column: Viridis BEH-2 EP OBD (250*19 mm, 5μ)
Mobile Phase A: 0.1% DEA in n-Hexane
Mobile Phase B: EtOH: MeOH (50:50)
Flow rate: 16.0 mL/min
Isocratic Table

| Time | % A | % B |
| --- | --- | --- |
| 0 | 97.2 | 2.8 |
| 25 | 97.2 | 2.8 |

Solvents used for dilution: Methanol/Ethanol

Compound 24: Yield: 9.1% (80 mg, off white solid). LCMS: 98.7%, m/z=215.2 [M+H]$^+$ $^1$H NMR (DMSO-d$_6$, 400 MHz): δ 10.47 (s, 1H), 7.22 (d, J=7.95 Hz, 1H), 7.00 (s, 1H), 6.74 (dd, J=0.98, 7.95 Hz, 1H), 2.84-2.88 (m, 2H), 2.70-2.76 (m, 6H), 2.40 (s, 3H), 2.35 (s, 3H).

Compound 25: Yield: 3.4% (30 mg, Off white solid). LC-MS: 95.8%, m/z=215.2 [M+H]$^+$ $^1$H NMR (DMSO-d$_6$, 400 MHz): δ 10.68 (br s, 1H), 7.05 (d, J=7.95 Hz, 1H), 6.82 (t, J=7.52 Hz, 1H), 6.62 (d, J=7.09 Hz, 1H), 3.10-3.14 (m, 2H), 2.89-2.92 (m, 2H), 2.81 (br s, 4H), 2.56 (s, 3H), 2.46 (br s, 3H).

Example 26. Compound 26 & Compound 27

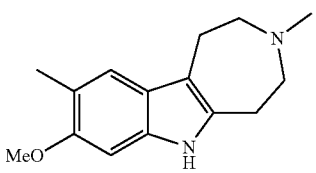

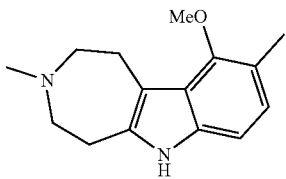

27

The crude was purified by prep-HPLC to get fraction-1 and fraction-2. The fraction-1 is # (right) by $^1$H NMR whereas fraction-2 is # (left).

Prep-HPLC Purification Method:
Preparative HPLC Column: Chiralpak IC (250*30 mm, 5μ)
Mobile Phase A: 0.1% DEA in n-Hexane
Mobile Phase B: EtOH: MeOH (80:20)
Flow rate: 35.0 mL/min
Isocratic Table

| Time | % A | % B |
|------|-----|-----|
| 0    | 90  | 10  |
| 20   | 90  | 10  |

Solvents used for dilution: Methanol/Ethanol

Compound 26: Yield: 24.6% (160 mg, off white solid). LCMS: 100%, m/z=245.1 [M+H]$^+$ $^1$H NMR (DMSO-$d_6$, 400 MHz): δ 10.33 (s, 1H), 7.07 (s, 1H), 6.71 (s, 1H), 3.75 (s, 3H), 2.81-2.85 (m, 2H), 2.69-2.73 (m, 6H), 2.39 (s, 3H), 2.18 (s, 3H).

Compound 27: Yield: 3.1% (20 mg, Off white solid). LC-MS: 100%, m/z=245.1 [M+H]$^+$ $^1$H NMR (DMSO-$d_6$, 400 MHz): δ 10.63 (s, 1H), 6.89 (d, J=8.07 Hz, 1H), 6.75 (d, J=8.07 Hz, 1H), 3.65 (s, 3H), 3.03-3.06 (m, 2H), 2.82-2.85 (m, 2H), 2.64-2.67 (m, 4H), 2.37 (s, 3H), 2.23 (s, 3H).

Example 27. Compound 28

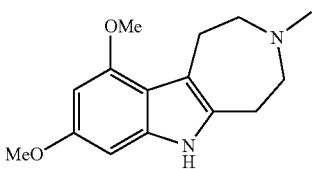

28

Compound 28: Yield: 4.7% (30 mg, pale brown solid). LC-MS: 96.2%, m/z=261.2 [M+H]$^+$ $^1$H NMR (DMSO-$d_6$, 400 MHz): δ 10.44 (s, 1H), 6.32 (d, J=1.96 Hz, 1H), 6.05 (d, J=1.96 Hz, 1H), 3.76 (s, 3H), 3.71 (s, 3H), 3.02-3.04 (m, 2H), 2.77-2.80 (m, 2H), 2.64 (br dd, J=3.24, 6.17 Hz, 4H), 2.35 (s, 3H).

Plasticity Effects.

Treatment of rat embryonic cortical neurons with TBG led to increased dendritic arbor complexity at 6 days in vitro (DIV6) as measured by Sholl analysis (FIG. 3A-C). The effect of TBG on dendritic growth appears to be 5-HT2A-dependent, as pretreatment with ketanserin—a 5-HT2A antagonist—completely abrogated its effects (FIG. 3D), which further validates in vitro receptor profiling.

Figure 3G:
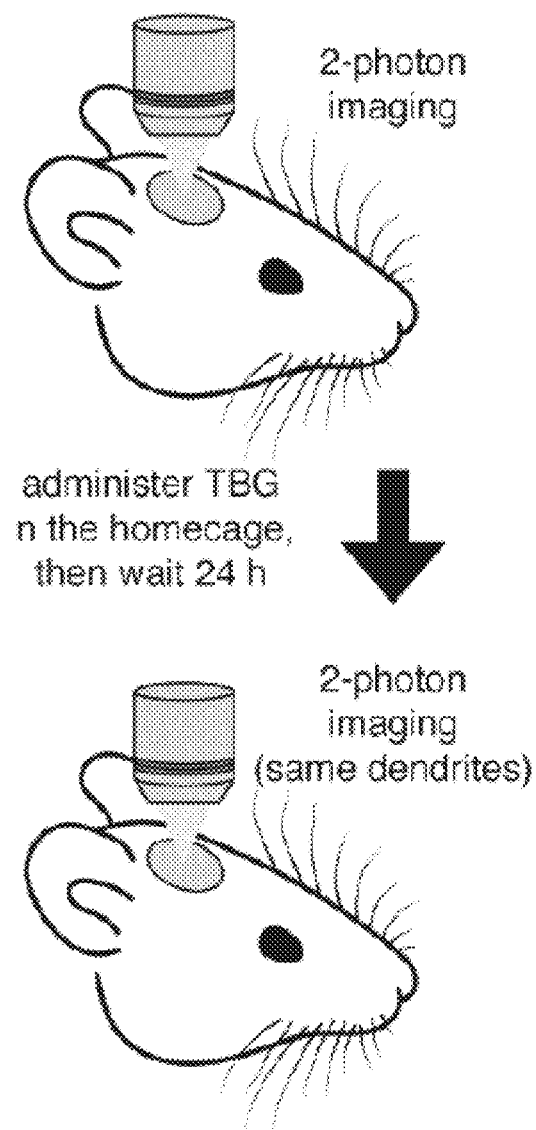
Figure 3H:
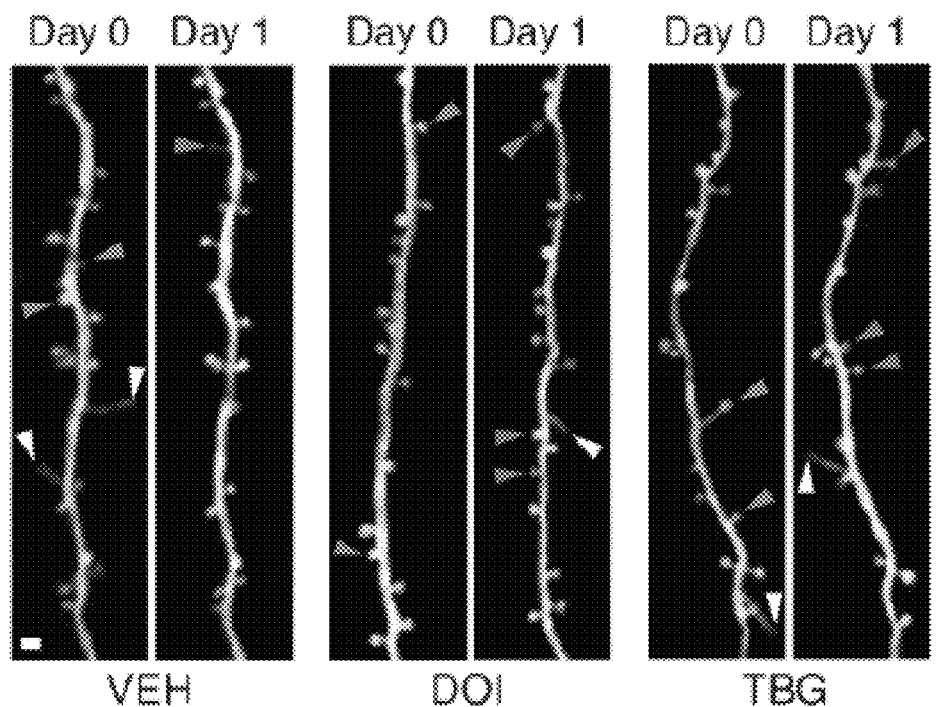
Figure 3I:
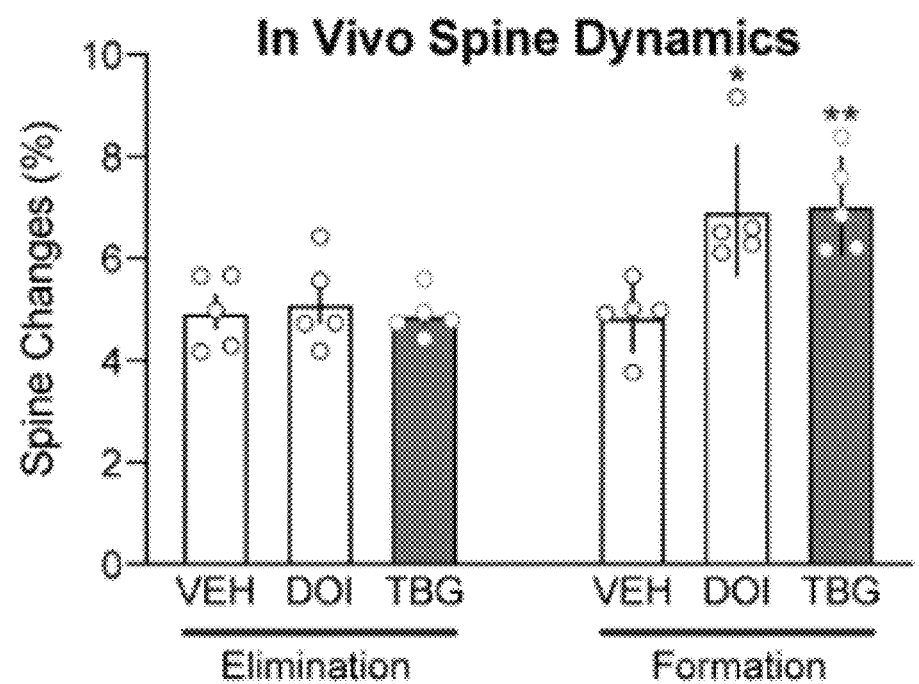

In addition to promoting dendritic growth, TBG also increases dendritic spine density to a comparable extent as ibogaine in mature cortical cultures (DIV20) (FIG. 3E and FIG. 3F). The effects of TBG on cortical dendritic spine dynamics in vivo using transcranial 2-photon imaging (FIG. 3G) was assessed. First, spines were imaged on specific dendritic loci defined by their relation to blood vessel and dendritic architectures. Next, the animals were systemically administered vehicle, TBG, or the hallucinogenic 5-HT2A agonist 2,5-dimethoxy-4-iodoamphetamine (DOI). After 24 h, the same dendritic segments were re-imaged, and the number of spines gained or lost was quantified. Neither TBG nor DOI affected spine elimination. Both compounds increased spine formation in mouse primary sensory cortex (FIG. 3H and FIG. 3I).

As increased cortical structural plasticity in the anterior parts of the brain mediates the sustained (>24 h) antidepressant-like effects of ketamine and play a role in the therapeutic effects of 5-HT2A agonists, the impact of TBG on forced swim test (FST) behavior (FIG. 4A and FIG. 4B) was evaluated. First, a pretest was used to induce a depressive phenotype. Drugs were administered 24 h after the pre-test, and the FST was performed 24 h and 7 d post drug administration. Both ketamine and TBG significantly reduced immobility 24 h after drug administration.

To assess the anti-addictive potential of TBG, an alcohol drinking paradigm that models heavy alcohol use and binge drinking behavior in humans was employed. Using a 2-bottle choice setup (20% ethanol (v/v), EtOH vs. water, $H_2O$), mice were subjected to repeated cycles of binge drinking and withdrawal over the course of 7 weeks (FIG. 4C). This schedule results in heavy EtOH consumption (11.44±0.76 g/kg/24 h), binge drinking-like behavior (3.89±0.33 g/kg/4 h), and generates blood alcohol content equivalent to that of human subjects suffering from alcohol use disorder (AUD). Next, TBG or vehicle were administered via intraperitoneal injection 3 h prior to a drinking session, and EtOH and $H_2O$ consumption was monitored (FIG. 4C). As shown in FIG. 4D, TBG robustly reduces binge drinking during the first 4 h with every animal (19 total) decreasing EtOH consumption. Water intake was not affected (FIG. 4D). Consumption of ethanol was lower for at least two days following TBG administration with no effect on water intake (FIG. 4E). Similar effects have been observed previously for ibogaine suggesting that TBG may be a highly efficacious agent for the treatment of AUD.

Biological Protocols.

Data Analysis and Statistics. Treatments were randomized, and data were analyzed by experimenters blinded to treatment conditions. Statistical analyses were performed using GraphPad Prism (version 8.1.2) unless noted otherwise. All comparisons were planned prior to performing each experiment. Data are represented as mean±SEM, unless otherwise noted, with asterisks indicating *p<0.05, p<0.01, *p<0.001, and ****p<0.0001. Boxplots depict the three quartile values of the distribution with whiskers extending to points that lie within 1.5 IQRs (interquartile range) of the lower and upper quartile. Observations falling outside this range are displayed independently. For FIGS. 2B, 3C, 3D, 3F, 3I, 4B and 5B, compound treatments were compared to the VEH control using a one-way ANOVA with Dunnett's post hoc test. For FIGS. 2E and F, time 0 h and time 1 h (before and after drug administration, respectively) were compared using a paired t-test. For FIGS. 2I and 11, compound treatments were compared using Fisher's exact test and p-values are indicated in the text. For FIG. 4D, data were analyzed using a paired t-test. FIG. 4E, data were analyzed using a two-way ANOVA with Sidak's post hoc test.

Drugs. The NIH Drug Supply Program provided ibogaine hydrochloride (IBO) and noribogaine (NOR). Other chemicals were purchased from commercial sources such as ketamine hydrochloride (KET, Fagron), ketanserin (KETSN, ApexBio), eugenol (Tokyo Chemical Industries), and 5-hydroxytryptamine (Sigma-Aldrich). The fumarate salt of 5-methoxy-N,N-dimethyltryptamine (2:1, 5-MeO-DMT:fumaric acid) was synthesized in house as described previously and judged to be analytically pure based on NMR and LC-MS data. For cell culture experiments, VEH=0.1% (agonist studies) or 0.2% (antagonist studies) molecular biology grade dimethyl sulfoxide (Sigma-Aldrich). For in vivo experiments, VEH=USP grade saline (0.9%). Free bases were used for all cellular experiments while the fumarate salts of ibogainalog and tabernanthalog were used for the in vivo studies.

Animals. All experimental procedures involving animals were approved by either the UCD, UCSF, or UCSC Institutional Animal Care and Use Committee (IACUC) and adhered to principles described in the National Institutes of Health Guide for the Care and Use of Laboratory Animals. The University of California, Davis (UCD), the University of California, San Francisco (UCSF), and the University of California, Santa Cruz (UCSC) are accredited by the Association for Assessment and Accreditation of Laboratory Animal Care International (AAALAC).

Calculation of CNS MPO Score. CNS MPO scores were calculated using a previously published method. Predicted PKA values were determined using Marvin Sketch (19.25.0). Log P and total polar surface area were predicted using Molinspiration. Log D was calculated using the following equation Log D=Log P$-LOG_{10}(1+10^{(pka-7.4)})$.

Dendritogenesis Experiments. For the dendritogenesis experiments conducted using cultured cortical neurons, timed pregnant Sprague Dawley rats were obtained from Charles River Laboratories (Wilmington, Mass.). Full culturing, staining, and analysis details were performed as previously described. (Dunlap, L. et al., 2019)

Head-Twitch Response (HTR). The head-twitch response assay was performed as described previously using both male and female C57BL/6J mice (2 per treatment). The mice were obtained from Jackson Laboratory (Sacramento, Calif.) and were approximately 8 weeks old at the time of the experiments. Compounds were administered via intraperitoneal injection (5 mL/kg) using 0.9% saline as the vehicle. As a positive control, 5-MeO-DMT fumarate (2:1 amine/acid) was utilized, which was synthesized as described previously. Behavior was videotaped, later scored by two blinded observers, and the results were averaged (Pearson correlation coefficient=0.93).

hERG Inhibition Studies. All experiments were conducted manually using an EPC-10 amplifier (HEKA, Lambrecht/Pfalz, Germany) at room temperature in the whole-cell mode of the patch-clamp technique. HEK-293 cells stably expressing hKv11.1 (hERG) under G418 selection were a generous gift from Craig January (University of Wisconsin, Madison). Cells were cultured in DMEM containing 10% fetal bovine serum, 2 mM glutamine, 1 mM sodium pyruvate, 100 U/mL penicillin, 100 µg/mL streptomycin, and 500 mg/ml G418. Before experiments, cells were cultured to 60-80% confluency and lifted using TrypLE and plated onto poly-L-lysine-coated coverslips. Patch pipettes were pulled from soda lime glass (micro-hematocrit tubes) and had resistances of 2-4 MΩ. For the external solution, normal sodium Ringer was used (160 mM NaCl, 4.5 mM KCl, 2 mM $CaCl_2$, 1 mM $MgCl_2$, 10 mM HEPES, pH 7.4 and 290-310 mOsm). The internal solution used was potassium fluoride with ATP (160 mM KF, 2 mM $MgCl_2$, 10 mM EGTA, 10 mM HEPES, 4 mM NaATP, pH=7.2 and 300-320 mOsm). A 2-step pulse (applied every 10 sec) from −80 mV first to 40 mV for 2 sec and then to −60 mV for 4 sec, was used to elicit hERG currents. The percent reduction of tail current amplitude by the drugs was determined and data are shown as mean+/−SD. For all experiments, solutions of the drugs were prepared fresh from 10 mM stock solutions in DMSO. The final DMSO concentration never exceeded 1%.

Serotonin and Opioid Receptor Functional Assays. Functional assay screens at 5-HT and opioid receptors were performed in parallel using the same compound dilutions and 384-well format high-throughput assay platforms. Assays assessed activity at all human isoforms of the receptors, except where noted for the mouse 5-HT2A receptor. Receptor constructs in pcDNA vectors were generated from the Presto-Tango GPCR library with minor modifications. All compounds were serially diluted in drug buffer (HBSS, 20 mM HEPES, pH 7.4 supplemented with 0.1% bovine serum albumin and 0.01% ascorbic acid) and dispensed into 384-well assay plates using a FLIPR$^{TETRA}$ (Molecular Devices). Every plate included a positive control such as 5-HT (for all 5-HT receptors), DADLE (DOR), salvinorin A (KOR), and DAMGO (MOR). For measurements of 5-HT2A, 5-HT2B, and 5-HT2C Gq-mediated calcium flux function, HEK Flp-In 293 T-Rex stable cell lines (Invitrogen) were loaded with Fluo-4 dye for one hour, stimulated with compounds and read for baseline (0-10 seconds) and peak fold-over-basal fluorescence (5 minutes) at 25° C. on the FLIPR$^{TETRA}$. For measurement of 5-HT6 and 5-HT7a functional assays, Gs-mediated cAMP accumulation was detected using the split-luciferase GloSensor assay in HEKT cells measuring luminescence on a Microbeta Trilux (Perkin Elmer) with a 15 min drug incubation at 25° C. For 5-HT1A, 5-HT1B, 5-HT1F, MOR, KOR, and DOR functional assays, Gi/o-mediated cAMP inhibition was measured using the split-luciferase GloSensor assay in HEKT cells, conducted similarly as above, but in combination with either 0.3 µM isoproterenol (5-HT1A, 5-HT1B, 5-HT1F) or 1 µM forskolin (MOR, KOR, and DOR) to stimulate endogenous cAMP accumulation. For measurement of 5-HT1D, 5-HT1E, 5-HT4, and 5-HT5A functional assays, β-arrestin2 recruitment was measured by the Tango assay utilizing HTLA cells expressing TEV fused-β-arrestin2, as described previously with minor modifications. Data for all assays were plotted and non-linear regression was performed using "log(agonist) vs. response" in Graphpad Prism to yield E max and $EC_{50}$ parameter estimates.

$5HT_{2A}$ Sensor Assays. HEK293T (ATCC) 5HT2A sensor stable line (sLight1.3s) was generated via lentiviral transduction of HIV-EF1α-sLight1.3 and propagated from a single colony. Lentivirus was produced using $2^{nd}$ generation lentiviral plasmids pHIV-EF1α-sLight1.3, pHCMV-G, and pCMV-deltaR8.2.

For the screening of the 41 compounds, sLight1.3s cells were plated in 96-well plates at a density of 40000 24-hours prior to imaging. On the day of imaging, compounds solubilized in DMSO were diluted from the 100 mM stock solution to working concentrations of 1 mM, 100 µM and 1 µM with a DMSO concentration of 1%. Immediately prior to imaging, cells growing in DMEM (Gibco) were washed 2× with HBSS (Gibco) and in agonist mode 180 µL of HBSS or in antagonist mode 160 µL of HBSS was added to each well after the final wash. For agonist mode, images were taken before and after the addition of the 20 µL compound working solution into the wells containing 180 µL HBSS. This produced final compound concentrations of 100 µM, 10

µM and 100 nM with a DMSO concentration of 0.1%. For antagonist mode, images were taken before and after addition of 20 µL of 900 nM 5-HT and again after 20 µL of the compound working solutions to produce final concentrations of 100 nM for 5HT and 100 µM, 10 µM and 100 nM for the compounds with a DMSO concentration of 0.1%. Each compound was tested in triplicates (3 wells) for each concentration (100 µM, 10 µM and 100 nM). Additionally, within each plate, 100 nM 5HT and 0.1% DMSO controls were also imaged.

Imaging was performed using the Leica DMi8 inverted microscope with a 40× objective using the FITC preset with an excitation of 460 nm and emission of 512-542 nm. For each well, the cellular membrane where the 5HT2A sensor is targeted was autofocused using the adaptive focus controls and 5 images from different regions within the well were taken with each image processed from a 2×2 binning.

For data processing, the membranes from each image was segmented and analyzed using a custom algorithm written in MATLAB producing a single raw fluorescence intensity value. For each well the 5 raw fluorescence intensity values generated from the 5 images were averaged and the change in fluorescence intensity (dFF) was calculated as:

$$dFF = (F_{sat} - F_{apo})/F_{apo}$$

For both agonist and antagonist modes, the fluorescence intensity values before compound addition in HBSS only were used as the $F_{apo}$ values while the fluorescence intensity values after compound addition were used as the $F_{sat}$ values.

For agonist mode, data are as percent activation relative to 5HT, where 0 is the average of the DMSO wells and 100 is the average of the 100 µM 5HT wells. For antagonist mode, the inactivation score was calculated as:

$$\text{Inactivation score} = (dFFF(\text{Compound}+5HT) - dFF(5HT))/dFF(5HT)$$

Spinogenesis Experiments. Spinogenesis experiments were performed as previously described with the exception that cells were treated on DIV19 and fixed 24 h after treatment on DIV20. (Ly, C. et al., 2018) The images were taken on a Nikon HCA Confocal microscope a with a 100×/NA 1.45 oil objective. DMSO and ketamine (10 µM) were used as vehicle and positive controls, respectively.

In Vivo Spine Dynamics. Male and female Thy1-GFP-M line mice (n=5 per condition) were purchased from The Jackson Laboratory (JAX #007788) and maintained in UCSC animal facilities according to an IACUC approved protocol. In vivo transcranial two-photon imaging and data analysis were performed as previously described. Briefly, mice were anesthetized with an intraperitoneal (i.p.) injection of a mixture of ketamine (87 mg/kg) and xylazine (8.7 mg/kg). A small region of the exposed skull was manually thinned down to 20-30 µm for optical access. Spines on apical dendrites in mouse primary sensory cortices were imaged using a Bruker Ultima IV two-photon microscope equipped with an Olympus water-immersion objective (40×, NA=0.8) and a Ti:Sapphire laser (Spectra-Physics Mai-Tai, excitation wavelength 920 nm). Images were taken at a zoom of 4.0 (pixel size 0.143×0.143 µm) and Z-step size of 0.7 µm. The mice received an i.p. injection (injection volume=5 mL/kg) of DOI (10 mg/kg) or TBG (50 mg/kg) immediately after they recovered from anesthesia given prior to the first imaging session. The animals were re-imaged 24 h after drug administration. Dendritic spine dynamics were analyzed using ImageJ. Spine formation and elimination were quantified as percentages of spine number on day 0.

Forced Swim Test (FST). Male C57/BL6J mice (9-10 weeks old at time of experiment, n=10 per condition) were obtained from the Jackson Lab and housed 4-5 mice/cage in a UCD vivarium following an IACUC approved protocol. After 1 week in the vivarium each mouse was handled for approximately 1 minute by a male experimenter for 3 consecutive days leading up to the first FST. All experiments were carried out by the same male experimenter who performed handling. During the FST, mice underwent a 6 min swim session in a clear Plexiglas cylinder 40 cm tall, 20 cm in diameter, and filled with 30 cm of 24±1° C. water. Fresh water was used for every mouse. After handling and habituation to the experimenter, drug-naïve mice first underwent a pretest swim to more reliably induce a depressive phenotype in the subsequent FST sessions. Immobility scores for all mice were determined after the pre-test and mice were randomly assigned to treatment groups to generate groups with similar average immobility scores to be used for the following two FST sessions. The next day, the animals received intraperitoneal injections of TBG (50 mg/kg), a positive control (ketamine, 3 mg/kg), or vehicle (saline). The following day, the animals were subjected to the FST and then returned to their home cages. One week later, the FST was performed again to assess the sustained effects of the drugs. All FSTs were performed between the hours of 8 am and 1 pm. Experiments were video-recorded and manually scored offline. Immobility time—defined as passive floating or remaining motionless with no activity other than that needed to keep the mouse's head above water—was scored for the last 4 min of the 6 min trial.

Alcohol Consumption. Male C57/BL6J mice (6-8 weeks old) were obtained from The Jackson Laboratory (Bar Harbor, Me.) and were individually housed in a reverse light/dark cycle room (lights on 10:00 pm-10:00 am). Temperature was kept constant at 22±2° C., and relative humidity was maintained at 50±5%. Mice were given access to food and tap water ad libitum. After one week of habituation to the vivarium, the two-bottle choice alcohol-drinking paradigm was conducted as described previously. For 7 weeks, mice were given intermittent access in their home cage to alcohol. On Mondays, Wednesdays, and Fridays, two bottles were made available for 24 h—one containing 20% ethanol and another containing only water. On Tuesdays, Thursdays, Saturdays, and Sundays, the animals were only given access to water. After 7 weeks, mice were administered TBG (50 mg/kg) or vehicle (saline) via intraperitoneal injection 3 h before the beginning of a drinking session. Ethanol (g/kg) and water (ml/kg) intake were monitored during the first 4 h (initial binge), the first 24 h, and the second 24 h. Next, the animals were only given water for 48 h before the start of another drinking session when ethanol and water consumption was monitored. The placement (right or left) of the bottles was altered in each session to control for side preference. Spillage was monitored using an additional bottle in a nearby unused cage. Alcohol preference was calculated as the ratio between alcohol/(water+alcohol). Mice were tested using a counterbalanced, within subject design with one week of drug-free alcohol drinking regimen between treatments. One mouse was excluded because the bottle was leaking.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound selected from the group consisting of:

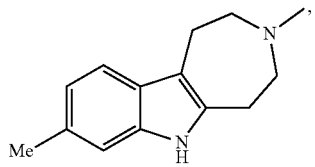

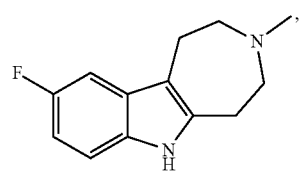

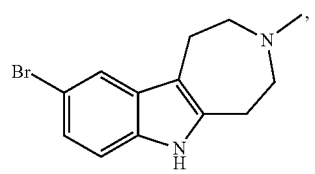

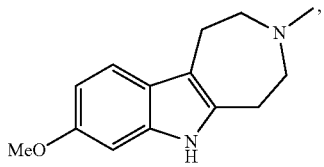

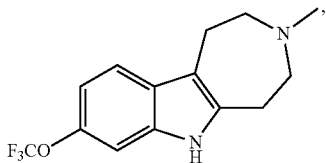

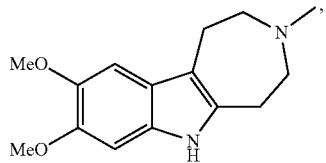

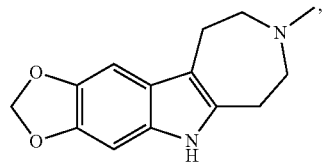

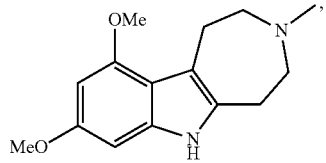

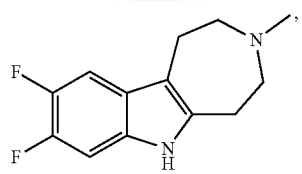

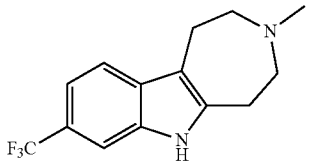

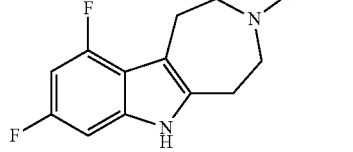 and

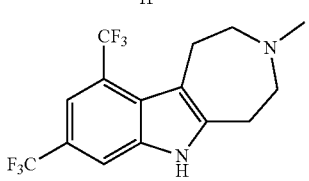

or a pharmaceutically acceptable salt thereof.

2. The compound of claim 1, wherein the compound is

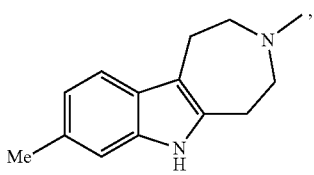 [SMILES: Cc1ccc2c3c([nH]c2c1)CCN(C)CC3]

or a pharmaceutically acceptable salt thereof.

3. The compound of claim 1, wherein the compound is

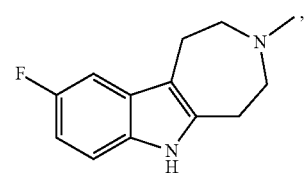 [SMILES: CN1CCc2[nH]c3ccc(F)cc3c2CC1]

or a pharmaceutically acceptable salt thereof.

4. The compound of claim 1, wherein the compound is

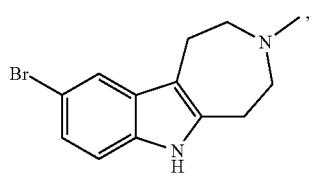 [SMILES: CN1CCc2[nH]c3ccc(Br)cc3c2CC1]

or a pharmaceutically acceptable salt thereof.

5. The compound of claim 1, wherein the compound is

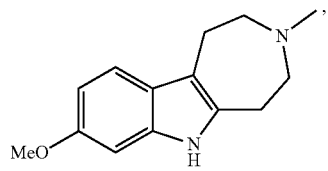 [SMILES: COc1ccc2c3c([nH]c2c1)CCN(C)CC3]

or a pharmaceutically acceptable salt thereof.

6. The compound of claim 1, wherein the compound is

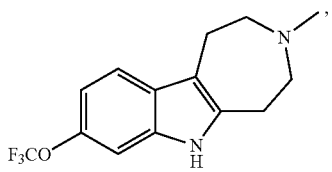 [SMILES: CN1CCc2[nH]c3cc(OC(F)(F)F)ccc3c2CC1]

or a pharmaceutically acceptable salt thereof.

7. The compound of claim 1, wherein the compound is

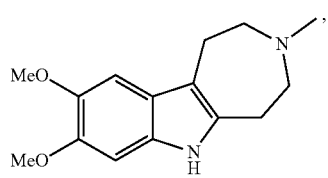 [SMILES: COc1cc2[nH]c3c(c2cc1OC)CCN(C)CC3]

or a pharmaceutically acceptable salt thereof.

8. The compound of claim 1, wherein the compound is

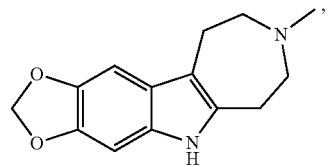

or a pharmaceutically acceptable salt thereof.

9. The compound of claim 1, wherein the compound is

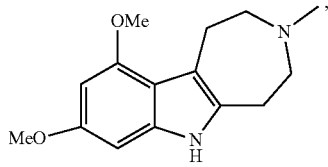 [SMILES: COc1cc(OC)c2c3c([nH]c2c1)CCN(C)CC3]

or a pharmaceutically acceptable salt thereof.

10. The compound of claim 1, wherein the compound is

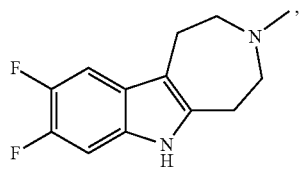 [SMILES: CN1CCc2[nH]c3cc(F)c(F)cc3c2CC1]

or a pharmaceutically acceptable salt thereof.

11. The compound of claim 1, wherein the compound is

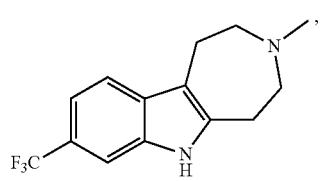

or a pharmaceutically acceptable salt thereof.

12. The compound of claim 1, wherein the compound is

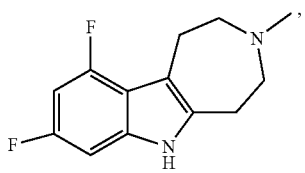 [SMILES: CN1CCc2[nH]c3cc(F)cc(F)c3c2CC1]

or a pharmaceutically acceptable salt thereof.

13. The compound of claim 1, wherein the compound is

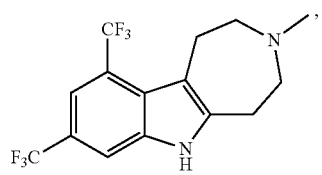 [SMILES: CN1CCc2[nH]c3cc(C(F)(F)F)cc(C(F)(F)F)c3c2CC1]

or a pharmaceutically acceptable salt thereof.

14. A pharmaceutical composition, comprising a therapeutically effective amount of a compound selected from the group consisting of:

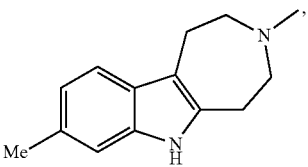

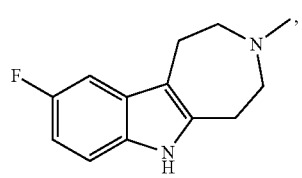

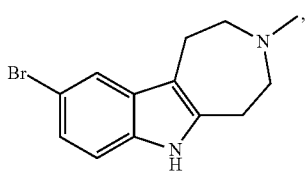

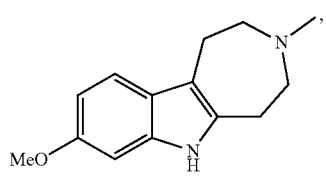

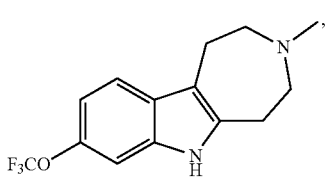

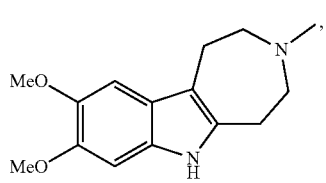

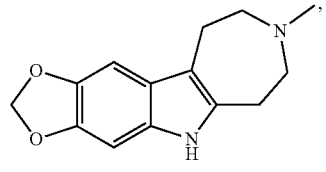

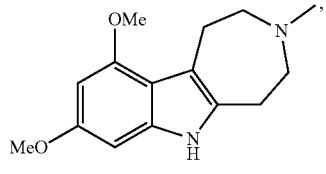

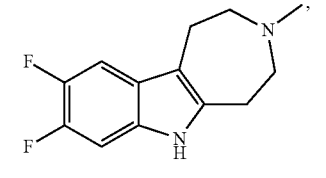

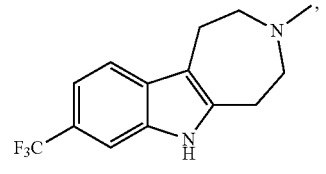

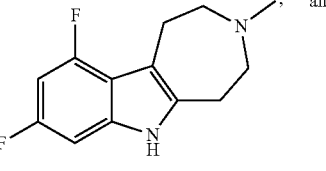

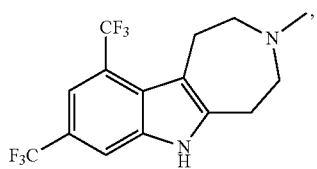

or a pharmaceutically acceptable salt thereof, and a pharmaceutically acceptable excipient.

15. The pharmaceutical composition of claim 14, wherein the compound is

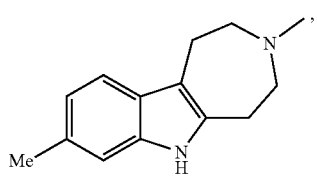 [SMILES: Cc1ccc2c3c([nH]c2c1)CCN(C)CC3]

or a pharmaceutically acceptable salt thereof.

16. The pharmaceutical composition of claim 14, wherein the compound is

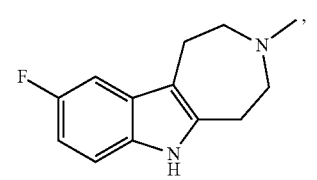 [SMILES: CN1CCc2[nH]c3ccc(F)cc3c2CC1]

or a pharmaceutically acceptable salt thereof.

17. The pharmaceutical composition of claim 14, wherein the compound is

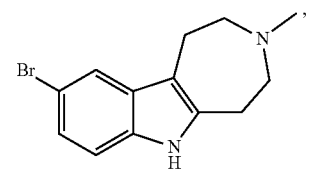

or a pharmaceutically acceptable salt thereof.

18. The pharmaceutical composition of claim 14, wherein the compound is

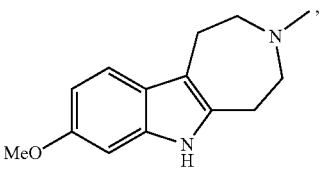

or a pharmaceutically acceptable salt thereof.

19. The pharmaceutical composition of claim 14, wherein the compound is

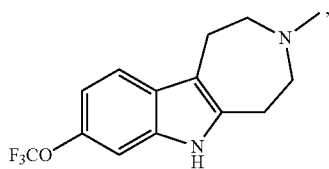 [SMILES: CN1CCc2[nH]c3cc(OC(F)(F)F)ccc3c2CC1]

or a pharmaceutically acceptable salt thereof.

20. The pharmaceutical composition of claim 14, wherein the compound is

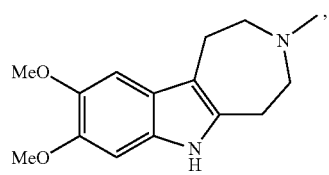

or a pharmaceutically acceptable salt thereof.

21. The pharmaceutical composition of claim 14, wherein the compound is

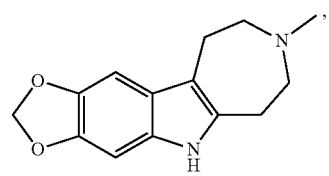

or a pharmaceutically acceptable salt thereof.

22. The pharmaceutical composition of claim 14, wherein the compound is

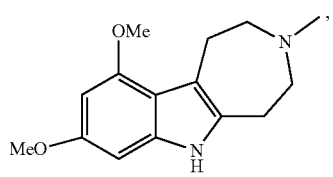 [SMILES: COc1cc(OC)c2c3c([nH]c2c1)CCN(C)CC3]

or a pharmaceutically acceptable salt thereof.

23. The pharmaceutical composition of claim 14, wherein the compound is

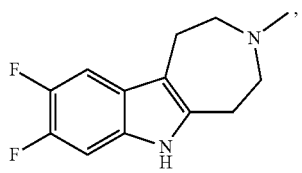 [SMILES: CN1CCc2[nH]c3cc(F)c(F)cc3c2CC1]

or a pharmaceutically acceptable salt thereof.

24. The pharmaceutical composition of claim 14, wherein the compound is

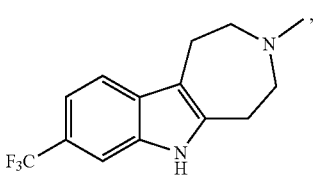 [SMILES: CN1CCc2[nH]c3cc(C(F)(F)F)ccc3c2CC1]

or a pharmaceutically acceptable salt thereof.

25. A method for treating a brain disorder in a subject, wherein the method comprises administering to the subject in need thereof a therapeutically effective amount of a compound of claim 1, or a pharmaceutically acceptable salt thereof.

26. The method of claim 25, wherein the brain disorder is selected from the group consisting of a psychological disorder, depression, addiction, anxiety, and post-traumatic stress disorder.

27. The method of claim 26, wherein the brain disorder is selected from the group consisting of depression and addiction.

28. The method of claim 25, wherein the brain disorder is selected from the group consisting of treatment resistant depression, suicidal ideation, major depressive disorder, bipolar disorder, schizophrenia, and substance use disorder.

* * * * *